(12) United States Patent
Burgard et al.

(10) Patent No.: US 11,293,026 B2
(45) Date of Patent: *Apr. 5, 2022

(54) MICROORGANISMS FOR THE PRODUCTION OF ADIPIC ACID AND OTHER COMPOUNDS

(71) Applicant: Genomatica, Inc., San Diego, CA (US)

(72) Inventors: Anthony P. Burgard, Elizabeth, PA (US); Priti Pharkya, San Diego, CA (US); Robin E. Osterhout, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/550,010

(22) Filed: Aug. 23, 2019

(65) Prior Publication Data

US 2020/0248189 A1    Aug. 6, 2020

Related U.S. Application Data

(63) Continuation of application No. 15/184,940, filed on Jun. 16, 2016, now Pat. No. 10,415,042, which is a continuation of application No. 14/450,150, filed on Aug. 1, 2014, now Pat. No. 9,382,556, which is a continuation of application No. 13/452,642, filed on Apr. 20, 2012, now abandoned, which is a continuation of application No. 13/288,699, filed on Nov. 3, 2011, now Pat. No. 8,216,814, which is a continuation of application No. 13/088,256, filed on Apr. 15, 2011, now Pat. No. 8,062,871, which is a continuation of application No. 12/875,084, filed on Sep. 2, 2010, now Pat. No. 8,088,607, which is a continuation of application No. 12/413,355, filed on Mar. 27, 2009, now Pat. No. 7,799,545.

(60) Provisional application No. 61/040,059, filed on Mar. 27, 2008.

(51) Int. Cl.
| | |
|---|---|
| C12N 1/21 | (2006.01) |
| C12P 7/44 | (2006.01) |
| C12N 9/04 | (2006.01) |
| C12N 9/12 | (2006.01) |
| C12N 9/10 | (2006.01) |
| C12N 9/88 | (2006.01) |
| C12N 9/02 | (2006.01) |
| C12N 9/16 | (2006.01) |
| C12N 15/52 | (2006.01) |
| C12P 13/00 | (2006.01) |
| C12P 13/02 | (2006.01) |
| C12P 17/10 | (2006.01) |
| C12N 9/80 | (2006.01) |
| C12P 7/46 | (2006.01) |
| C12P 7/62 | (2022.01) |

(52) U.S. Cl.
CPC ............ *C12N 15/52* (2013.01); *C12N 9/001* (2013.01); *C12N 9/0006* (2013.01); *C12N 9/0008* (2013.01); *C12N 9/1029* (2013.01); *C12N 9/1096* (2013.01); *C12N 9/80* (2013.01); *C12N 9/88* (2013.01); *C12P 7/44* (2013.01); *C12P 7/46* (2013.01); *C12P 7/62* (2013.01); *C12P 13/001* (2013.01); *C12P 13/005* (2013.01); *C12P 13/02* (2013.01); *C12P 17/10* (2013.01); *C12Y 101/01035* (2013.01); *C12Y 102/0101* (2013.01); *C12Y 103/01031* (2013.01); *C12Y 206/01* (2013.01); *C12Y 402/01* (2013.01)

(58) Field of Classification Search
None
See application file for complete search history.

(56) References Cited

U.S. PATENT DOCUMENTS

| | | | |
|---|---|---|---|
| 3,912,586 | A | 10/1975 | Kaneyuki et al. |
| 4,871,667 | A | 10/1989 | Imada et al. |
| 4,950,429 | A | 8/1990 | Vagt et al. |
| 5,143,833 | A | 9/1992 | Datta |

(Continued)

FOREIGN PATENT DOCUMENTS

| | | |
|---|---|---|
| EP | 0111683 A1 | 6/1984 |
| EP | 1 473 368 | 11/2004 |

(Continued)

OTHER PUBLICATIONS

U.S. Appl. No. 12/413,355, 2009/0305364, filed Mar. 27, 2009, Nashaat T. Nashed, Microorganisms for the Production of Adipic Acid and Other Compounds, Issued.

(Continued)

*Primary Examiner* — Robert B Mondesi
*Assistant Examiner* — Todd M Epstein
(74) *Attorney, Agent, or Firm* — Greenberg Traurig, LLP

(57) ABSTRACT

The invention provides a non-naturally occurring microbial organism having an adipate, 6-aminocaproic acid or caprolactam pathway. The microbial organism contains at least one exogenous nucleic acid encoding an enzyme in the respective adipate, 6-aminocaproic acid or caprolactam pathway. The invention additionally provides a method for producing adipate, 6-aminocaproic acid or caprolactam. The method can include culturing an adipate, 6-aminocaproic acid or caprolactam producing microbial organism, where the microbial organism expresses at least one exogenous nucleic acid encoding an adipate, 6-aminocaproic acid or caprolactam pathway enzyme in a sufficient amount to produce the respective product, under conditions and for a sufficient period of time to produce adipate, 6-aminocaproic acid or caprolactam.

16 Claims, 9 Drawing Sheets

(56) References Cited

U.S. PATENT DOCUMENTS

| | | |
|---|---|---|
| 5,143,834 A | 9/1992 | Glassner et al. |
| 5,168,055 A | 12/1992 | Datta et al. |
| 5,487,987 A | 1/1996 | Frost et al. |
| 5,504,004 A | 4/1996 | Guettler et al. |
| 5,521,075 A | 5/1996 | Guettler et al. |
| 5,573,931 A | 11/1996 | Guettler et al. |
| 5,616,496 A | 4/1997 | Frost et al. |
| 5,700,934 A | 12/1997 | Wolters et al. |
| 5,770,435 A | 6/1998 | Donnelly et al. |
| 5,869,301 A | 2/1999 | Nghiem et al. |
| 6,159,738 A | 12/2000 | Donnelly et al. |
| 6,194,572 B1 | 2/2001 | Buijs et al. |
| 6,214,592 B1 | 4/2001 | Crouzet et al. |
| 6,280,986 B1 | 8/2001 | Hespell et al. |
| RE37,393 E | 9/2001 | Donnelly et al. |
| 6,323,341 B1 | 11/2001 | Agterberg et al. |
| 6,353,100 B1 | 3/2002 | Guit et al. |
| 6,365,376 B1 | 4/2002 | Brzostowicz et al. |
| 6,448,061 B1 | 9/2002 | Pan et al. |
| 6,455,284 B1 | 9/2002 | Gokam et al. |
| 6,498,242 B1 | 12/2002 | Qiong et al. |
| 6,660,857 B2 | 12/2003 | Agterberg et al. |
| 6,743,610 B2 | 6/2004 | Donnelly et al. |
| 7,127,379 B2 | 10/2006 | Palsson et al. |
| 7,223,567 B2 | 5/2007 | Ka-Yiu et al. |
| 7,262,046 B2 | 8/2007 | Ka-Yiu et al. |
| 7,491,520 B2 | 2/2009 | Raemakers-Franken et al. |
| 7,799,545 B2 | 9/2010 | Burgard et al. |
| 7,947,483 B2 | 5/2011 | Burgard et al. |
| 8,062,871 B2 | 11/2011 | Burgard et al. |
| 8,216,814 B2 | 7/2012 | Burgard et al. |
| 2002/0012939 A1 | 1/2002 | Palsson |
| 2002/0062388 A1 | 5/2002 | Ogier et al. |
| 2002/0106358 A1 | 8/2002 | Hopwood et al. |
| 2002/0168654 A1 | 11/2002 | Maranas et al. |
| 2003/0028915 A1 | 2/2003 | Tilton et al. |
| 2003/0059792 A1 | 3/2003 | Palsson et al. |
| 2003/0087381 A1 | 5/2003 | Gokarn |
| 2003/0113886 A1 | 6/2003 | Brzostowicz et al. |
| 2003/0224363 A1 | 12/2003 | Park et al. |
| 2003/0233218 A1 | 12/2003 | Schilling |
| 2004/0009466 A1 | 1/2004 | Maranas et al. |
| 2004/0029149 A1 | 2/2004 | Palsson et al. |
| 2004/0072723 A1 | 4/2004 | Palsson et al. |
| 2005/0079482 A1 | 4/2005 | Maranas et al. |
| 2005/0250135 A1 | 11/2005 | Klaenhammer et al. |
| 2007/0111294 A1 | 5/2007 | Burgard et al. |
| 2007/0149777 A1 | 6/2007 | Frost |
| 2007/0184539 A1 | 8/2007 | San et al. |
| 2007/0239987 A1 | 10/2007 | Hoole et al. |
| 2007/0254341 A1 | 11/2007 | Raemakers-Franken et al. |
| 2007/0271453 A1 | 11/2007 | Pohja et al. |
| 2008/0182308 A1 | 7/2008 | Donaldson et al. |
| 2008/0261230 A1 | 10/2008 | Liao et al. |
| 2008/0274526 A1 | 11/2008 | Bramucci et al. |
| 2009/0047718 A1 | 2/2009 | Blaschek et al. |
| 2009/0047719 A1 | 2/2009 | Burgard et al. |
| 2009/0068207 A1 | 3/2009 | Breitbart et al. |
| 2009/0246842 A1 | 10/2009 | Hawkins et al. |
| 2009/0305364 A1 | 12/2009 | Burgard et al. |
| 2010/0168481 A1 | 7/2010 | Farmer et al. |
| 2011/0091944 A1* | 4/2011 | Wu .................. C12P 17/10 435/121 |
| 2011/0171699 A1 | 7/2011 | Raemakers-Franken et al. |
| 2012/0028320 A1* | 2/2012 | Raemakers-Franken .................. C12N 9/1025 435/135 |

FOREIGN PATENT DOCUMENTS

| | | |
|---|---|---|
| JP | 50 006776 | 1/1975 |
| WO | WO 2002/055995 | 7/2002 |
| WO | WO 2003/106998 | 12/2003 |
| WO | WO 2005/068643 | 7/2005 |
| WO | WO 2006/031424 | 3/2006 |
| WO | WO 2006/034156 | 3/2006 |
| WO | WO 2007/030830 | 3/2007 |
| WO | WO 2007/050671 | 5/2007 |
| WO | WO 2007/066430 A1 | 6/2007 |
| WO | WO 2008/080124 | 7/2008 |
| WO | WO 2009/113853 | 9/2009 |
| WO | WO 2009/113855 | 9/2009 |

OTHER PUBLICATIONS

U.S. Appl. No. 12/875,084, 2010/0330626, filed Sep. 2, 2010, Nashaat T. Nashed, Microorganisms for the Production of Adipic Acid and Other Compounds, Issued.

U.S. Appl. No. 13/088,256, 2011/0195466, filed Apr. 15, 2011, Nashaat T. Nashed, Microorganisms for the Production of Adipic Acid and Other Compounds, Issued.

U.S. Appl. No. 13/288,699, 2012/0115194, filed Nov. 3, 2011, Nashaat T. Nashed, Microorganisms for the Production of Adipic Acid and Other Compounds, Issued.

U.S. Appl. 13/452,642, 2012/0264179, filed Apr. 20, 2012, Nashaat T. Nashed, Microorganisms for the Production of Adipic Acid and Other Compounds, Abandoned.

U.S. Appl. No. 13/525,129, 2013/0095540, filed Jun. 15, 2012, Nashaat T. Nashed, Microorganisms for the Production of Adipic Acid and Other Compounds, Issued.

U.S. Appl. No. 14/450,150, 2015/0167028, filed Aug. 1, 2014, Nashaat T. Nashed, Microorganisms for the Production of Adipic Acid and Other Compounds, Issued.

U.S. Appl. No. 12/776,365, 2010/0317069, filed May 7, 2010, Iqbal Hossain Chowd Hury, Microorganisms and Methods for the Biosynthesis of Adipate, Hexamethylene Diamine and 6-Aminocaproic Acid, Issued.

U.S. Appl. No. 13/730,612, 2013/0303723, filed Dec. 28, 2012, Iqbal Hossain Chowd Hury, Microorganisms and Methods for the Biosynthesis of Adipate, Hexamethylene Diamine and 6-Aminocaproic Acid, Issued.

U.S. Appl. No. 15/263,149, 2017/0218414, filed Sep. 12, 2016, Iqbal Hossain Chowd Hury, Microogranisms and Methods for the Biosynthesis of Adipate, hexamethylene Diamine and 6-Aminocaproic Acid, Issued.

Alexson et al., "NADH-sensitive propionyl-CoA hydrolase in brown-adipose-tissue mitochondria of the rat," *Biochim, Biophys. Acta* 1005(1): 13-19 (1989).

Alhapel et al., "Molecular and functional analysis of nicotinate catabolism in Eubacterium barkeri," *Proc. Natl. Acad. Sci. U.S.A.* 103(33):12341-12346 (2006).

Alper et al., "Engineering yeast transcription machinery for improved ethanol tolerance and production," *Science* 314(5805): 1565-1568 (2006).

Andersson et al., "Effect of different carbon sources on the production of succinic acid using metabolically engineered *Escherichia coli*," *Biotechnol. Prog.* 23(2):381-388 (2007).

Aneja et al., "Poly-3-hydroxybutyrate degradation in Rhizobium (Sinorhizobium) meliloti: isolation and characterization of a gene encoding 3-hydroxybutryate dehydrogenase," *J. Bacteriol.* 181(3):849-857 (1999).

Aoshima et al., "A novel biotin protein required for reductive carboxylation of 2-oxoglutarate by isocitrate dehydrogenase in Hydrogenobacter thermophilus TK-6," Mol. Microbiol. 51(3):791-798 (2004).

Aoshima et al., "Nondecarboxylating and decarboxylating isocitrate dehydrogenases: oxalosuccinate reductase as an ancestral form of isocitrate dehydrogenase," *J. Bacteriol.* 190(6):2050-2055 (2008).

Aoshima et al., "A novel oxalosuccinate-forming enzyme involved in the reductive carboxylation of 2-oxoglutarate in Hydrogenobacter thermophilus TK-6," *Mol. Microbiol.* 62(3):748-759 (2006).

Aragon et al., "A survey of Enzymes Which Generate or Use Acetoacetyl Thioesters in Rat Liver," *J. Biol. Chem.* 258(8):4725-4733 (1983).

Arps et al., "Genetics of serine pathway enzymes in Methylobacterium extorquens AMI: phosphoenolpyruvate carboxylase and malyl Coenzyme A lyase," *J. Bacteriol.* 175:3776-3783 (1993).

(56) References Cited

OTHER PUBLICATIONS

Atsumi et al., "Metabolic engineering of *Escherichia coli* for 1-butanol production," *Metab. Eng.* 10(6):305-311 (2007).
Atteia et al., "Pyruvate formate-lyase and a novel route of eukaryotic ATP synthesis in Chlamydomonas mitochondria," *J. Biol. Chem.* 281:9909-9918 (2006).
Auerbach et al., "Lactate dehydrogenase from the hyperthermophilic bacterium thermotoga maritima: the crystal structure at 2.1 Å resolution reveals strategies for intrinsic protein stabilization," *Structure* 6:769-781 (1998).
Bachmann et al., "Kinetic Mechanism of the β-Lactam Synthetase of *Streptomyces clavuligerus*," *Biochemistry* 39:11187-11193 (2000).
Barbe et al., "Unique features revealed by the genome sequence of Acinetobacter sp. ADP1, a versatile and naturally transformation competent bacterium," *Nucleic Acids Res.* 32(19):5766-5779 (2004).
Barker et al., "Butyryl-CoA:Acetoacetate CoA-transferase from Lysine-fermenting Clostridium," *J. Biol. Chem.* 253(4):1219-1225 (1978).
Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J. Bacteriol.* 172(12):7035-7042 (1990).
Bauer et al., "Improved Expression of Human Interleukin-2 in High-Cell-Density Fermentor Cultures of *Escherichia coli* K-12 by a Phosphotransacetylase Mutant," *Appl. Environ. Microbiol.* 56:1296-1302 (1990).
Benning et al., "New reactions in the crotonase superfamily: Structure of methylmalonyl CoA decarboxylase from *Escherichia coli*," *Biochemistry* 39:4630-4639 (2000).
Biellmann et al., "Aspartate-β-semialdehyde dehydrogenase from *Escherichia coli*. Purification and general properties," *Eur. J. Biochem.* 104(1):53-58 (1980).
Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur. J. Biochem.* 123(3):563-569 (1982).
Blazquez et al., "Identification and analysis of a glutaryl-CoA dehydrogenase-encoding gene and its cognate transcriptional regulator from Azoarcus sp. CIB," *Environ. Microbiol.* 10(2):474-482 (2008).
Bock et al., "Purification and characterization of two extremely thermostable enzymes, phosphate acetyltransferase and acetate kinase, from the hyperthermophilic eubacterium Thermotoga maritima," *J. Bacteriol.* 181:1861-1867 (1999).
Bonner et al., "Purification and properties of fatty acyl thioesterase I from *Escherichia coli*," *J. Biol. Chem.* 247(10):3123-3133 (1972).
Boronin et al., "Plasmids specifying ε-caprolactam degradation in Pseudomonas strains," *FEMS Microbiol. Lett.* 22(3):167-170 (1984).
Bower et al., "Cloning, sequencing, and characterization of the Bacillus subtilis biotin biosynthetic operon," *J. Bacteriol.* 178(14):4122-4130 (1996).
Boynton et al., "Cloning, sequencing, and expression of clustered genes encoding β-hydroxybutyryl-Coenzyme A (CoA) dehydrogenase, crotonase, and butyryl-CoA dehydrogenase from Clostridium acetobulylicum ATCC 824," *J. Bacteriol.* 178(11):3015-3024 (1996).
Braune et al., "The sodium ion translocating glutaconyl-CoA decarboxylase from Acidaminococcus fermentans: cloning and function on the genes forming a second operon," *Mol. Microbiol.* 31(2):473-487 (1999).
Brown et al., "Comparative structural analysis and kinetic properties of lactate dehydrogenases from the four species of human malarial parasites," *Biochemistry* 43:6219-6229 (2004).
Bu et al., "Two human glutamate decarboxylases, 65-kDa GAD and 67-kDa GAD, are each encoded by a single gene," *Proc. Natl. Acad. Sci. U.S.A.* 89:2115-2119 (1992).
Buck et al., "Primary structure of the succinyl-CoA synthetase of *Escherichia coli*," *Biochem.* 24(22):6245-6252 (1985).

Buckel and Golding, "Radical species in the catalytic pathways of enzymes from anaerobes," *FEMS Microbiol. Rev.* 22(5):523-541 (1999).
Buckel et al., "Glutaconate CoA-Transferase from Acidaminococcus fermentans," *Eur. J. Biochem.* 118:315-321 (1981).
Bühler et al., "On the kinetics and mechanism of enoate reductase," *Hoppe Seylers Z. Physiol. Chem.* 363(6):609-625 (1982).
Bunch et al., "The IdhA gene encoding the fermentative lactate dehydrogenase of *Escherichia coli*," *Microbiol.* 143:187-195 (1997).
Burgard et al., "Minimal Reaction Sets for *Escherichia coli* Metabolism under Different Growth Requirements and Uptake Environments," *Biotechnol. Prog.* 17:791-797 (2001).
Burgard et al., "Optknock: a bilevel programming framework for identifying gene knockout strategies for microbial strain optimization," *Biotechnol. Bioeng.* 84(6):647-657 (2003).
Buzenet et al., "Purification and properties of 4-Aminobutyrate 2-Ketoglutarate Aminotransferase From Pig Liver," *Biochimica. Biophysica. Acta.* 522:400-411 (1978).
Campbell et al., "The enigmatic *Escherichia coli* fadE gene is yafH," *J. Bacteriol.* 184(13):3759-3764 (2002).
Campbell et al., "A new *Escherichia coli* metabolic competency: growth on fatty acids by a novel anaerobic β-oxidation pathway," *Mol. Microbiol.* 47(3):793-805 (2003).
Carpenter et al., "Structure of dehydroquinate synthase reveals an active site capable of multistep catalysis," *Nature* 394:299-302 (1998).
Cary et al., "Cloning and expression of Clostridium acetobutylicum phosphotransbutyrylase and butyrate kinase genes in *Escherichia coli*," *J. Bacteriol.* 170(10):4613-4618 (1988).
Cha et al., "Stereo- and regiospecific cis,cis-muconate cycloisomerization by Rhodococcus rhodochrous N75," *FEMS Microbiol. Lett.* 224:29-34 (2003).
Chang et al., "Effects of deletions at the carboxyl terminus of Zymomonas mobilis pyruvate decarboxylase on the kinetic properties and substrate specificity," *Biochemistry* 39(31):9430-9437 (2000).
Chaparro-Riggers et al., "Comparison of Three Enoate Reductases and their Potential Use for Biotransformations," *Adv. Synth. Catal.* 349:1521-1531 (2007).
Chatterjee et al., "Mutation of the ptsG Gene Results in Increased Production of Succinate in Fermentation of Glucose by *Escherichia coli*," *Appl. Env. Microbiol.* 67:148-154 (2001).
Chen et al., "Cloning, Sequencing, Heterologous Expression, Purification, and Characterization of Adenosylcobalamin-dependent D-Ornithine Aminomutase from Clostridium sticklandii," *J. Biol. Chem.* 276:44744-44750 (2001).
Choi et al., "Enhanced production of cis,cis-muconate in a cell-recycle bioreactor," *J. Ferment. Bioeng.* 84:70-76 (1997).
Colby et al., "Purification and properties of 3-hydroxybutyryl-Coenzyme A dehydrogenase from Clostridium beijerinckii ("Clostridium butylicum") NRRL B593," *Appl. Environ. Microbiol.* 58:3297-3302 (1992).
Coleman, "Expression of a glutamate decarboxylase homologue is required for normal oxidative stress tolerance in Saccharomyces cerevisiae," *J. Biol. Chem.* 276:244-250. (2001).
Cooper, "Glutamate-γ-aminobutyrate transaminase," *Methods Enzymol*, 113:80-82 (1985).
Cox et al., "Development of a metabolic network design and optimization framework incorporating implementation constraints: A succinate production case study," *Metab. Eng.* 8(1):46-57 (2006).
Cunningham et al., "Transcriptional regulation of the aconitase genes (acnA and acnB) of *Escherichia coli*," *Microbiology* 143(Pt 12):3795-3805 (1997).
De Biase et al., "Isolation, overexpression, and biochemical characterization of the two isoforms of glutamic acid decarboxylase from Escherichia coli," *Protein Expr, Purif,* 8:430-438 (1996).
De Mendonca et al., "Functional characterization by genetic complementation of aroB-encoded dehydroquinate synthase from Mycobacterium tuberculosis H37Rv and its heterologous expression and purification," *J. Bacteriol.* 189:6246-6252 (2007).
De Smidt et al., "The alcohol dehydrogenases of Saccharomyces cerevisiae: a comprehensive review," *FEMS Yeast Rev.* 7:967-978 (2008).

(56) References Cited

OTHER PUBLICATIONS

Deana, "Substrate specificity of a dicarboxy 1-CoA: dicarboxylic acid Coenzyme A transferase from rat liver mitochondria," Biochem. Int. 26(4):767-773 (1992).
Di Gennaro, "Styrene lower catabolic pathway in Pseudomonas fluorescens ST: identification and characterization of genes for phenylacetic acid degradation," Arch. Microbiol. 188(2): 117-125 (2007).
Diaz et al., "Gene cloning, heterologous overexpression and optimized refolding of the NAD-glutamate dehydrogenase from Haloferax mediterranei," Extremophiles 10:105-115 (2006).
Dittrich et al., "Redistribution of Metabolic Fluxes in the Central Aerobic Metabolic Pathway of E.coli Mutant Strains with Deletion of the ackA-pta and poxB Pathways for the Synthesis of Isoamyl Acetate." Biotechnol, Prog, 21(21:627-631 (2005).
Donnelly et al., "Succinic semialdehyde dehydrogenases of Escherichia coli: Their role in the degradation of p-hydroxyphenylacetate and y-aminobutyrate," Eur. J. Biochem. 113:555-561 (1981).
Donnelly et al., "Two succinic semialdehyde dehydrogenases are induced when Escherichia coli K-12 Is grown on y-aminobutyrate," J. Bacteriol. 145:1425-1427 (1981).
Drake, "Acetogenesis, acetogenic bacteria, and the acetyl-CoA "Wood/Ljungdahl" pathway: past and current perspectives," in Aceto genesis. H. L. Drake, (ed.), Chapman & Hall, New York, p. 3-60 (1994).
Draths et al., "Environmentally compatible synthesis of adipic acid from D-glucose," J. Am. Chem. Soc. 116:399-400 (1994).
Dutscho et al., "Cloning and sequencing of the genes of 2-hydoxyglutaryl-CoA dehydratase from Acidaminococcus fermentans," Eur. J. Biochem. 181(3):741-746 (1989).
Eden et al., "Involvement of branched-chain amino acid aminotransferases in the production of fusel alcohols during fermentation in yeast," Appl, Microbiol. Biotechnol, 55:296-300 (2001).
Eikmanns et al., "The phosphoenolpyruvate carboxylase gene of Corynebacterium glutamicum: Molecular cloning, nucleotide sequence, and expression." Mol. Gen. Genet. 218:330-339 (1989).
Fi Tzgerald and Flanagan, "Characterization and sequence analysis of the human ornithine decarboxylase gene," DNA 8:(9):623-634 (1989).
Fong et al., "Metabolic gene-deletion strains of Escherichia coli evolve to computationally predicted growth phenotypes," Nat. Genet. 36(10): 1056-1058 (2004).
Fontaine et al., "Molecular charcterization and transcriptional analysis of adhE2, the gene encoding the NADH-dependent aldehyde/alcohol dehydrogenase responsible for butanol production in alcohologenic cultures of Clostridium acetobutylicum ATCC 824," J. Bacteriol. 184:821-830 (2002).
Frost et al., "Synthesis of adipic acid from biomass-derived carbon sources," Biotechnol. Adv. 15(1):294 (1997).
Frost, "Redefining chemical manufacture. Replacing petroleum with plant-derived feedstocks," Ind. Biotechnol. l(1):23-24 (2005).
Fu et al., "Crystal structures of human glutaryl-CoA dehydrogenase with and without an alternate substrate: structural bases of dehydrogenation and decarboxylation reactions," Biochemistry 43(30):9674-9684 (2004).
Fukao et al., "Succinyl-CoA:3-ketoacid CoA transferase (SCOT): cloning of the human SCOT gene, tertiary structural modeling of the human SCOT monomer, and characterization of three pathogenic mutations," Genomics 68:144-151 (2000).
Fukumura et al., "Hydrolysis of cyclic and linear oligomers of 6-aminocaproic acid by a bacterial cell extract," J. Biochem. 59(6):531-536 (1966).
Fukumura et al., "Purification and properties of a novel enzyme, L-α-amino-ε-caprolactamase from Cryptococcus laurentii," FEBS Lett. 89(2):298-300 (1978).
Garras et al., "Subcellular localisation and induction of NADH-sensitive acetyl-CoA hydrolase and propionyl-CoA hydrolase activities in rat liver under lipogenic conditions after treatment with sulfur-substituted fatty acids," Biochim. Biophys. Acta. 1255(21:154-160 (1995).

Garvie, "Bacterial lactate dehydrogenases," Microbiol. Rev. 44:106-139 (1980).
Gesher et al., "Genes Coding for a New Pathway of Aerobic Benzoate Metabolism in Azoarcus evansil," J. Bacteriol. 184(22):6301-6315 (2002).
Gibson et al., "Physical and genetic interactions of cytosolic malate dehydrogenase with other gluconeogenic enzymes," J. Biol. Chem. 278:25628-25636 (2003).
Giesel et al., "On the occurrence of enoate reductase and 2-oxo-carboxylate reductase in Clostridia and some observations on the amino acid fermentation by Peptostreptococcus anaerobius," Arch. Microbiol. 135(1):51-57 (1983).
Glasemacher et al., "Purification and properties of acetyl-CoA synthetase (ADP-forming), an archael enzyme of acetate formation and ATP synthesis, from the hyperthermophile Pyrococcus furiosus," Eur. J. Biochem. 244:561-567 (1997).
Göbel et al., "Degradation of Aromatics and Chloroaromatics by Pseudomonas sp. Strain B13: Cloning, Characterization, and analysis of Sequences Encoding 3-Oxoadipate:Succinyl-Coenzyme A (CoA) Transferase and 3-oxoaipyl-CoA Thiolase," J. Bacteriol. 184(1):216-223 (2002).
Gokarn et al., "Metabolic Analysis of Escherichia coli in the Presence and Absence of the Carboxylating Enzymes Phosphoenolpyruvate Carboxylase and Pyruvate Carboxylase," Appl. Environ. Microbiol. 66:1844-1850 (2000).
Gordon et al., "Purification, properties and immunological relationship of L(+)-lactate dehydrogenase from Lactobacillus casei," Eur. J. Biochem. 67:543-555 (1976).
Haller et al., "Discovering new enzymes and metabolic pathways: conversion of succinate to propionate by Escherichia coli," Biochem. 39(16):4622-4629 (2000).
Hartel et al., "Purification of glutaryl-CoA dehydrogenase from Pseudomonas sp., an enzyme involved in the anaerobic degradation of benzoate," Arch. Mirobiol. 159:174-181 (1993).
Harwood et al., "The β-ketoadipate pathway and the biology of self-identity," Annu. Rev. Microbiol. 50:553-590 (1996).
Hashimoto et al., "Activation of L-Lysine ε-Dehydrogenase from Agrobacterium tumefaciens by Several Amino Acids and Monocarboxylates," J. Biochem. 106:76-80 (1989).
Hayden et al., "Glutamate dehydrogenase of Halobacterium salinarum: evidence that the gene sequence currently assigned to the NADP+ -dependent enzyme is in fact that of the NAD+ -dependent glutamate dehydrogenase," FEMS Microbiol. Lett. 211:37-41 (2002).
Hemschemeier et al., "Biochemical and physiological characterization of the pyruvate formate-lyase Pfl1 of Chlamydomonas reinhardtii, a typically bacterial enzyme in eukaryotic alga," Eukarvot. Cell 7:518-526 (2008).
Heydari et al., "Highly Stable L-Lysine 6-Dehydrogenase from the thermophile Geobacillus stearothermophilus Isolated from a Japanese Hot Spring: characterization, Gene Cloning and sequencing, and Expression," Appl. Environ. Microbiol. 70(2):937-942 (2004).
Highbarger et al., "Mechanism of the reaction catalyzed by acetoacetate decarboxylase. Importance of lysine 116 in determining the pKa of active-site lysine 115," Biochemistry 35(1):41-46 (1996).
Ho et al., "Regulation of serine biosynthesis in Arabidopsis. Crucial role of plastidic 3-phosphoglycerate dehydrogenase in non-photosynthetic tissues," J. Biol. Chem. 274:397-402 (1999).
Hoffmann et al., "Sterochemistry of the methylmalonyl-CoA decarboxylation reaction," FEBS Lett. 220:121-125 (1987).
Hoffmeister et al., "Mitochondrial trans-2-enoyl-CoA reductase of wax ester fermentation from Euglena gracilis defines a new family of enzymes involved in lipid synthesis," J. Biol. Chem. 280(6):4329-4338 (2005).
Hofmeister et al., "(R)-lactyl-CoA dehydratase from Clostridium propionicum. Stereochemistry of the dehydration of (R)-2-hydroxybutyryl-CoA to crotonly-CoA," Eur. J. Biochem. 206(2):547-552 (1992).
Hofmeister et al., "Cloning and expression of the two genes coding for L-serine dehydratase from Peptostreptococcus asaccharolyticus: relationship of the iron-sulfur protein to both L-serine dehydratases from Escherichia coli," J. Bacteriol. 179(15):4937-4941 (1997).

(56) References Cited

OTHER PUBLICATIONS

Hong et al., "Importance of redox balance on the production of succinic acid by metabolically engineered *Escherichia coli*," *Appl. Microbiol. Biotechnol.* 58:286-290 (2002).
Huang et al., "Identification and characterization of a second butyrate kinase from Clostridium acetobutylicum ATCC 824," *J. Mol. Microbiol. Biotechnol.* 2(1):33-38 (2000).
Hübner et al., "The mechanism of substrate activation of pyruvate decarboxylase: A first approach," *Eur. J. Biochem.* 92:175-181 (1978).
Hughes et al., "Cloning and expression of pea genes from Pseudomonas putida in *Escherichia coli*," *J. Gen. Microbiol.* 134:2877-2887 (1988).
Husain et al., "Partial purification and characterization of glutaryl-Coenzyme A dehydrogenase, electron transfer flavoprotein, and electron transfer flavoprotein-Q oxidoreductase from Paracoccus denitrificans," *J. Bacteriol.* 163:709-715 (1985).
Inui et al., "Occurrence of Oxygen-Sensitive, NADP+-Dependent Pyruvate-Dehydrogenase in Mitochondria of Euglena-Gracilis," *J. Biochem.* 96:931-934 (1984).
Ishida et al., Efficient production of L-Lactic acid by metabolically engineered Saccharomyces cerevisiae with a genome-integrated L-lactate dehydrogenase gene. *Appl. Envirom. Microbiol.* 71:1964-1970 (2005).
Ishige et al., "Wax ester production from n-alkanes by *Acinetobacter* sp. strain M-1: ultrastructure of cellular inclusions and role of acyl Coenzyme A reductase," *Appl. Environ. Microbiol.* 68(3): 1192-1195 (2002).
Ismail et al., "Functional genomics by NMR spectroscopy. Phenylacetate catabolism in *Escherichia coli*," *Eur. J. Biochem.* 270(14):3047-3054 (2003).
Ito et al., "D-3-hydroxybutyrate dehydrogenase from Pseudomonas fragi: molecular cloning of the enzyme gene and crystal structure of the enzyme," *J. Mol. Biol.* 355(4):722-733 (2006).
Jantama et al., "Combining metabolic engineering and metabolic evolution to develop nonrecombinant strains of *Escherichia coli* C that produce succinate and malate," *Biotechnol. Bioeng.* 99(5): 1140-1153 (2008).
Jantama et al., "Eliminating Side Products and Increasing succinate Yields in Engineered Strains of *Escherichia coli* C," *Biotechnol. Bioeng.* 101(5) 881-893 (2008).
Kaclikova et al., "Fumaric acid overproduction in yeast mutants deficient in fumarase," *FEMS Microbiol. Lett.* 91(2):101-106 (1992).
Kai et al., "Phosphoenolpyruvate carboxylase: three-dimensional structure and molecular mechanisms," *Arch. Biochem. Biophys.* 414:170-179 (2003).
Kanagawa et al., "Characterization of the 6-aminohexanoate-dimer hydrolase from *Pseudomonas* sp. NK87," J. Gen. Microbiol. 139(4):787-795 (1993).
Kanehisa et al., "KEGG: Kyoto Encyclopedia of Genes and Genomes database," *Nucleic Acids Res.* 28(1):27-30 (2000).
Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase," *J. Bacteriol.* 184(1):207-215 (2002).
Kessler et al., "Pyruvate-formate-lyase-deactivase and acetyl-CoA reductase activities of *Escherichia coli* reside on a polymeric protein particle encoded by adhE," *FEBS Lett.* 281(1-2):59-63 (1991).
Khan et al., "Molecular Properties and Enhancement of Thermostability by Random Mutagenesis of Glutamate Dehydrogenase from Bacillus subtilis," *Biosci. Biotechnol. Biochem.* 69(10):1861-1870 (2005).
Kim et al., "Effect of Overexpression of Actinobacillus succinogenes Phosphoenolpyruvate Carboxykinase on Succinate Production in *Escherichia coli*," *Appl. Env. Microbiol.* 70(2) 1238-1241 (2004).
Kim et al., "Dehydration of (R)-2-hydroxyacyl-CoA to enoyl-CoA in the fermentation of a-amino acids by anaerobic bacteria," *FEMS Microbiol. Rev.* 28:455-468 (2004).

Kinghorn et al., "The cloning and analysis of the aroD gene of *E. coli* K-12," *Gene* 14(1-2):73-80 (1981).
Kinoshita et al., "Purification and characterization of 6-aminohexanoic-acid-oligomer hydrolase of *Flavobacterium* sp. KI72," *Eur. J. Biochem.* 116(3):547-551 (1981).
Klatt et al., "Comparative genomics provides evidence for the 3-hydroxypropionate autotrophic pathway in filamentous anoxygenic phototrophic bacteria and in hot spring microbial mats," *Environ. Microbiol.* 9:2067-2078 (2007).
Knappe et al., "A radical-chemical route to acetyl-CoA: the anaerobically induced pyruvate formate-lyase system of *Escherichia coli*," *FEMS. Microbiol. Rev.* 75:383-398 (1990).
Kuchta et al., "Lactate Reduction in Clostridium propionicum Purification and properties of lactyl-CoA dehydratase" *J. Biol Chem.* 260(24):13181-13189 (1985).
Kulkarni et al., "Bioremediation of 8-caprolactum from nylon-6 waste water by use of Pseudomonas aeruginosa MCMB B-407," *Curr. Microbiol.* 37(3):191-194 (1998).
Kuznetsova et al., "Enzyme genomics: Application of general enzymatic screens to discover new enzymes," *FEMS Microbiol. Rev.* 29(2):263-279 (2005).
Laivenieks et al., "Cloning sequencing, and overexpression of the Anaerobiospirillum succinicproducens phosphoenolpyruvate carboxykinase (pckA) gene," *Appl. Environ. Microbiol.* 63:2273-2280 (1997).
Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem. J.* 395(1): 147-155 (2006).
Leduc et al., "The hotdog thioesterase EntH (YbdB) plays a role in vivo in optimal enterobactin biosynthesis by interacting with the ArCP domain of EntB," *J. Bacteriol.* 189(19):7112-7126 (2007).
Lee et al., "Cloning and Characterization of Mannheimia succiniciproducens MBEL55E Phosphoenolpyruvate Carboxykinase (pckA) Gene," *Biotechnol. Bioprocess Eng.* 7:95-99 (2002).
Lee et al., "Fermentative production of chemicals that can be used for polymer synthesis," *Macromol. Biosci.* 4:157-164 (2004).
Lee et al., "Genome-based metabolic engineering of Mannheimia succiniciproducens for succinic acid productiion," *Appl. Environ. Microbiol.* 72(3):1939-1948 (2006).
Lee et al., "Isolation and characterization of a new succinic acid-producing bacterium, Mannheimia succiniciproducens MBEL55E, from bovine rumen," *Appl. Microbiol. Biotechnol.* 58(5):663-668 (2002).
Lee et al., "Metabolic engineering of *Escherichia coli* for enhanced production of succinic acid, based on genome comparison and in silico gene knockout simulation," *Appl Environ Microbiol.* 71(12):7880-7887 (2005).
Leonardo et al., "Anaerobic Regulation of the adhE gene, Encoding the Fermentative Alcohol Dehydrogenase of *Escherichia coli*," *J. Bacteriology* 175(3):870-878 (1993).
Lin et al., "Chemostat culture characterization of *Escherichia coli* mutant strains metabolically engineered for aerobic succinate production: A study of the modified metabolic network based on metabolite profile, enzyme activity, and gene expression profile," *Metab. Eng*, 7(5-6):337-352 (2005).
Lin et al., "Fed-batch culture of a metabolically engineered *Escherichia coli* strain designed for high-level succinate production and yield under aerobic conditions," *Biotechnol. Bioeng.* 90:775-779 (2005).
Lin et al., "Genetic Reconstruction of the Aerobic Central Metabolism in *Escherichia coli* for the Absolute Aerobic Production of Succinate," *Biotechnol. Bioeng.* 89(2):148-156 (2005).
Lin et al., "Increasing the Acetyl-CoA pool in the Presence of Overexpressed Phosphoenolpyruvate Carboxylase or Pyruvate Carboxylase Enhances Succinate Production in *Escherichia coli*," *Biotechnol Prog.* 20(5):1599-1604 (2004).
Lin et al., "Metabolic engineering of aerobic succinate production systems in *Escherichia coli* to improve process productivity and achieve the maximum theoretical succinate yield," *Metab Eng.* 7(2):116-127 (2005).
Lin, "Metabolic Network Design and Engineering in *Escherichia coli*" Ph.D. Thesis, Rice University, Dept. of Bioengineering (2005).

(56) References Cited

OTHER PUBLICATIONS

Liu et al., "Microbial production of R-3-hydroxybutyric acid by recombinant E. coli harboring genes of phbA, phbB, and tesB," *Appl. Microbiol. Biotechnol.* 76:811-818 (2007).
Locher et al., "Crystal structure of the Acidaminococcus fermentans 2-hydroxyglutaryl-CoA dehydratase component A" *J. Mol. Biol.* 307(1):297-308 (2001).
Lütke-Eversloh et al., "Biochemical and molecular characterization of a succinate semialdehyde dehydrogenase involved in the catabolism of 4-hydroxybutyric acid in Ralstonia eutropha," *FEMS Microbiol. Lett.* 181(1):63-71 (1999).
Mack et al., "Location of the two genes encoding glutaconate Coenzyme A-transferase at the beginning of the hydroxyglutarate operon in Acidaminococcus fermentans," *Eur. J. Biochem.* 226:41-51 (1994).
Mai et al., "Purification and characterization of two reversible and ADP-dependent acetyl Coenzyme A synthetases from the hyperthermophilic archaeon Pyrococcus furiosus," *J. Bacteriol.* 178:5897-5903 (1996.).
Marks et al., "Molecular cloning and characterization of (R)-3-hydroxybutyrate dehydrogenase from human heart," *J. Biol. Chem.* 267(22):15459-15463 (1992).
Martínez-Blanco et al., "Purification and biochemical characterization of phenylacetyl-CoA ligase from Pseudomonas putida. A specific enzyme for the catabolism of phenylacetic acid," *J. Biol. Chem.* 265(12):7084-7090 (1990).
Martins et al., "Crystal structure of 4-hydroxybutyryl-CoA dehydratase: radical catalysis involving a [4Fe—4S] cluster and flavin," *Proc. Natl. Acad. Sci. U.S.A.* 101(44):15645-15649 (2004).
Mat-Jan et al., "Mutants of Escherichia coli Deficient in the Fermentative Lactate Dehydrogenase," *J. Bacteriol.* 171(1):342-348 (1989).
McAlister-Henn et al., "Isolation and expression of the gene encoding yeast mitochondrial malate dehydrogenase," *J. Bacteriol.* 169:5157-5166 (1987).
Megraw et al., "Formation of lactyl-Coenzyme A and pyruvyl-Coenzyme A from lactic acid by Escherichia coli," *J. Bacteriol.* 90(4):984-988 (1965).
Meynial-Salles et al., "A new process for the continuous production of succinic acid from glucose at high yield, titer and productivity," *Biotechnol. Bioeng.* 99(1):129-135 (2008).
Millard et al., "Enhanced production of succinic acid by overexpression of phosphoenolpyruvate carboxylase in Escherichia coli," *Appl. Environ. Microbiol.* 62(5):1808-1810 (1996).
Minard et al., "Isolation, nucleotide sequence analysis, and disruption of the MDH2 gene from Saccharomyces cerevisiae: evidence for three isozymes of yeast malate dehydrogenase," *Mol. Cell. Biol.* 11:370-380 (1991).
Misono et al., "Properties of L-lysine epsilon-dehydrogenase from Agrobacterium tumefaciens," *J. Biochem.* 105(6):1002-1008 (1989).
Mizugaki et al. "Studies on the metabolism of unsaturated fatty acids. IX. Stereochemical studies of the reaction catalyzed by trans-2-enoyl-Coenzyme A reductase of Escherichia coli," *J. Biochem.* 92(5):1649-1654 (1982).
Monastiri et al., "β-Ketothiolase (2-methylacetoacetyl-CoA thiolase) deficiency: A frequent disease in Tunisia?" *J. Inher. Metab. Dis.* 22:932-933 (1999).
Morton et al., "Cloning, sequencing, and expressions of genes encoding enzymes of the autotrophic acetyl-CoA pathway in the acetogen Clostridium thermoaceticum," In M. Sebald (ed.), *Genetics and molecular biology of anaerobic bacteria*, Springer Verlag, New York, 389-406 (1992).
Müh et al., "4-Hydroxybutyryl-CoA dehydratase from Clostridium aminobutyricum: characterization of FAD and iron-sulfur clusters involved in an overall non-redox reaction," Biochemistry 35:11710-11718 (1996).
Muller et al., "Activation of (R)-2-hydroxyglutaryl-CoA dehydratase from Acidaminococcus fermentans" *Eur. J. Biochem.* 230(2):698-704 (1995).

Naggert et al., "Cloning, sequencing, and characterization of *Escherichia coli* thioesterase II," *J. Biol. Chem.* 266(17):11044-11050 (1991).
Nakahigashi et al., "Nucleotide sequence of the fadA and fadB genes from Escherichia coli," *Nucleic Acids Res.* 18(16):4937 (1990).
Nishimaki et al., "Studies on the Metabolism of Unsaturated Fatty Acids. XIV. Purification and Properties of NADPH-Dependent trans-2-Enoyl-CoA Reductase of *Escherichia coli* K-12," *J. Biochem.* 95(5): 1315-1321 (1984).
Nissen et al., "Expression of a cytoplasmic transhydrogenase in Saccharomyces cerevisiae results in formation of 2-oxoglutarate due to depletion of the NADPH pool." *Yeast* 18:19-32 (2001).
Niu et al., "Benzene-free synthesis of adipic acid," *Biotechnol, Prog.* 18:201-211 (2002).
Njau et al., "Novel β-hydroxyacid dehydrogenases in *Escherichia coli* and Haemophilus influenza," *J. Biol. Chem.* 275(49):38780-38786 (2000).
Nogales et al., "Characterization of the last step of the aerobic phenylacetic acid degradation pathway," *Microbiology* 153(Pt 2):357-365 (2007).
Okino et al., "An effeicient succinic acid production process in a metabolically engineered Corynebacterium glutamicum strain," *Appl. Microbiol. Biotechnol.* 81(3):459-464 (2008).
Olivera et al., "Molecular characterization of the phenylacetic acid catabolic pathway in Pseudomonas putida U: the phenylacetyl-CoA catabolon," *Proc. Natl. Acad. Sci. U.S.A.* 95(11):6419-6424 (1998).
Parales et al., "Characterization of the Genes Encoding β-Ketoadipate: Succinyl-Coenzyme A Transferase in Pseudomonas putida," *J. Bacteriol.* 174(14):4657-4666 (1992).
Park et al., "Biosynthesis of poly (3-hydroxybutyrate-co-3-hydroxyalkanoates) by metabolically engineered *Escherichia coli* strains," *Appl. Biochem. Biotechnol.* 113-116:335-346 (2004).
Park et al., "Identification and characterization of a new enoyl Coenzyme A hydratase involved in biosynthesis of medium-chain-length polyhydroxyalkanoates in recombinant *Escherichia coli*," *J. Bacteriol.* 185(18):5391-5397 (2003).
Park et al., "New FadB homologous enzymes and their use in enhanced biosynthesis of medium-chain-length polyhydroxyalkanoates in FadB mutant *Escherichia coli*," *Biotechnol. Bioeng.* 86(6):681-686 (2004).
Parke et al., "Cloning and Genetic Characterization of dca Genes Required for β-Oxidation of Straight-Chain Dicarboxylic Acids in Acinetobacter sp. Strain ADP1," *Appl. Environ. Microbiol.* 67(10):4817-4827 (2001).
Petersen et al., "Purification of acetoacetate decarboxylase from Clostridium acetobutylicum ATCC 824 and cloning of the acetoacetate decarboxylase gene in Escherichia coli," *Appl. Environ. Microbiol.* 56:3491-3498 (1990).
Pharkya et al., "OptiStrain: A computational Framework for redesign of microbial production systems," *Genome Res.* 14(11):2367-2376 (2004).
Ponamoreva et al., "Transformation of Low-Molecular Linear Caprolactam Oligomers by the Caprolactam-Degrading Bacterium *Pseudomonas putida* BS394(pBS268)," *Microbiol.* 79(3):321-326 (2010).
Postma et al., "Phosphoenolpyruvate Carbohydrate Phosphotransferase Systems of Bacteria," *Microbiol Rev.* 57(3):543-594 (1993).
Price et al., "Genome-scale microbial in silico models: the constraints-based approach," *Trends Biotechnol.* 21(4):162-169 (2003).
Pucci et al., "Staphylococcus haemolyticus contains two D-glutamic acid biosynthetic activities, a glutamate racemase and a D-amino acid transminase," *J. Bacteriol.* 177(2):336-342 (1995).
Rado et al., "Phosphotransacetylase from Bacillus subtilis: purification and physiological studies," *Biochim. Biophys. Acta* 321:114-125 (1973).
Rasmussen et al. "Carbon Metabolism Regulates Expression of the pf1 (Pyruvate-Formate-Lyase) Gene in *Escherichia coli*," *J. Bacteriol.* 173(20):6390-6397 (1991).
Reed et al., "An expanded genome-scale model of *Escherichia coli* K-12 (iJR904 GSM/GPR)," *Genome. Biol.* 4(9):R54 (2003).
Reiser et al., "Isolation of mutants of Acinetobacter calcoaceticus deficient in wax ester synthesis and complementation of one muta-

(56) References Cited

OTHER PUBLICATIONS tion with a gene encoding a fatty acyl Coenzyme A reductase," *J. Bacteriol.* 179(9):2969-2975 (1997).
Rohdich et al., "Enoate reductases of Clostridia. Cloning, sequencing, and expression," *J. Biol. Chem.* 276(8):5779-5787 (2001).
Rudman et al., "Transamination in *Escherichia coli*," *J. Biol. Chem.* 200(2):591-604 (1953).
Ruldeekulthamrong et al., "Molecular characterization of lysine 6-dehydrogenase from Achromobacter denitrificans," BMB Reports 790-795 (2008).
Sanchez et al., "Efficient succinic acid production from glucose through overexpression of pyruvate carboxylase in an *Escherichia coli* alcohol dehydrogenase and lactate dehydrogenase mutant," *Biotechnol. Prog.* 21(21):358-365 (2005).
Sanchez et al., "Novel pathway engineering design of the anaerobic central metabolic pathway in *Escherichia coli* to increase succinate yield and productivity," *Metab. Eng.* 7(3): 229-239 (2005).
Sanchez et al., "Batch culture characterization and metabolic flux analysis of succinate-producing *Escherichia coli* strains," *Metab Eng.* 8(3):209-226 (2006).
Sato et al., "Poly [(R)-3-hydroxybutyrate] formation in *Escherichia coli* from glucose through an enoyl-CoA hydratase-mediated pathway," *J. Biosci. Bioeng*103(1):38-44 (2007).
Schweiger et al., "Purification of 2-hydroxyglutaryl-CoA dehydratase from Acidaminococcus fermentans. An iron-sulfur protein," *Eur. J. Biochem.* 169(2):441-448 (1987).
Scott et al., "Soluble γ-aminobutyric-glutamic transaminase from Pseudomonas fluorescens," *J. Biol. Chem.* 234(4):932-936 (1959).
Seedorf et al., "The genome of Clostridium kluyveri, a strict anaerobe with unique metabolic features," *Proc. Natl. Acad. Sci. U.S.A.* 105(6):2128-2133 (2008).
Shibata et al., "Purification, characterization, and immunological properties of fumarase from *Euglena gracilis* var. bacillaris," *J. Bacteriol.* 164(2):762-768 (1985).
Shigeoka et al., "Effect of L-glutamate on 2-oxoglutarate decarboxylase in Euglena gracilis," *Biochem. J.* 282 (Pt 2):319-323 (1992).
Slater et al., "Multiple β-ketothiolases mediate poly(P-hydroxyalkanoate) copolymer synthesis in Ralstonia eutropha," *J. Bacteriol.* 180(8): 1979-1987 (1998).
Smith et al., "Purification, properties and kinetic mechanism of Coenzyme A-linked aldehyde dehydrogenase from Clostridium kluyveri," *Arch. Biochem. Biophys.* 203:663-675 (1980).
Söhling et al., "Molecular analysis of the anaerobic succinate degradation pathway in Clostridium kluyveri," *J. Bacteriol.* 178:871-880 (1996).
Song et al., "Structure, function, and mechanism of the phenylacetate pathway hot dog-fold thioesterase PaaI," *J. Biol. Chem.* 281(16):11028-11038 (2006).
Sovik, "Mitochondrial 2-methylacetoacetyl-CoA thiolase deficiency: an inborn error of isoleucine and ketone body metabolism," *J. Inherit. Metab. Dis.* 16:46-54 (1993).
Steffan et al., "Isolation and characterization of the yeast gene encoding the MDH3 isozyme of malate dehydrogenase," *J. Biol. Chem.* 267:24708-24715 (1992).
Steinbacher et al., "Enoate reductase family," in Flavins and Flavoproteins, Proceedings of the Fourteenth International Symposium, St. John's College, University of Cambridge, UK, Jul. 14-18, 2002, Chapman et al., pp. 941-949, Rudolf Weber, Agency for Scientific Publications Berlin.
Sieinbüchel et al., "NAD-linked L(+)-lactate dehydrogenase from the strict aerobe alcaligenes eutrophus. 2. Kinetic properties and inhibition by oxaloacetate," *Eur. J. Biochem.* 130(2):329-334 (1983).
Stim-Herndon et al., "Characterization of an acetyl-CoA C-acetyltransferase (thiolase) gene from Clostridium acetobutylicum ATCC 824," *Gene* 154(1):81-85 (1995).
Stols et al., "Production of succinic acid through overexpression of NAD(+)-dependent malic enzyme in an *Escherichia coli* mutant," *Appl. Environ. Microbiol.* 63(7):2695-2701 (1997).
Stols et al., "Expression of Ascaris suum malic enzyme in a mutant *Escherichia coli* allows production of succinic acid from glucose," *Appl. Biochem. Biotechnol.* 63-65: 153-158 (1997).
Suarez De Mata et al., "Propionyl-CoA condensing enzyme from Ascaris muscle mitochondria. I. Isolation and characterization of multiple forms," *Arch. Biochem. Biophys.* 285(1): 158-165 (1991).
Suarez De Mata et al., "Propionyl-CoA condensing enzyme from Ascaris muscle mitochondria. II. Coenzyme A modulation," *Arch. Biochem. Biophys.* 285:166-171 (1991).
Suda et al., "Purification and properties of α-ketoadipate reductase, a newly discovered enzyme from human placenta," *Arch. Biochem. Biophys.* 176(2):610-620 (1976).
Suda et al., "Subcellular localization and tissue distribution of aα-ketoadipate reduction and oxidation in the rat," *Biochem. Biophys. Res. Commun*77(2):586-591 (1977).
Suematsu et al., "Molecular cloning and functional expression of rat liver cytosolic acetyl-CoA hydrolase," *Eur. J. Biochem.* 268(9):2700-2709 (2001).
Svetlitchnyi et al., "A functional Ni—Ni-[4Fe—4S] cluster in the monomeric acetyl-CoA synthase from Carboxydothermus hydrogenoformans," *Proc. Natl. Acad. Sci. U.S.A.* 101(2):446-451 (2004).
Takahashi-Abbe et al., "Biochemical and functional properties of a pyruvate formate-lyase (PFL)-activating system in Streptococcus mutans," *Oral Microbiol. Immunol.* 18:293-297 (2003).
Tamaki et al., "Purification and properties of aldehyde dehydrogenase from *Saccharomyces cerevisiae*," *J. Biochem.* 82(1):73-79 (1977).
Tanous et al., "Glutamate dehydrogenase activity can be transmitted naturally to Lactococcus lactis strains to stimulate amino acid conversion to aroma compounds," *Appl. Environ. Microbiol.* 72(2):1402-1409 (2006).
Thykaer et al., "Metabolic network analysis of an adipoyl-7-ADCA-producing strain of Penicillium chrysogenum: elucidation of adipate degradation," *Metab. Eng.* 4(2):151-158 (2002).
Tucci et al., "A novel prokaryotic trans-2-enoyl-CoA reductase from the spirochete Treponema denticola," *FEBS Lett.* 581(8):1561-1566 (2007).
Urbance et al., "Evaluation of succinic acid continuous and repeat-batch biofilm fermentation by Actinobacillus succinogenes using plastic composite support bioreactors," *Appl. Microbiol. Biotechnol.* 65(6):664-670 (2004).
Vadali, et al., "Cofactor engineering of intercellular CoA/acetyl-CoA and its effect on metabolic flux redistribution in *Escherichia coli*," *Metab Eng*6(2): 13 3-139 (2004).
Valdes-Hevia et al., "Isolation and characterization of the gene encoding phosphoenolpyruvate carboxykinase from *Saccharomyces cerevisiae*," *FEBS Lett.* 258:313-316 (1989).
Vamecq et al., "The microsomal dicarboxylyl-CoA synthetase," *Biochem. J.* 230(3):683-693 (1985).
Vandecasteele et al., "Aldehyde dehydrogenases from Pseudomonas aeruginosa," *Methods Enzymol,* 89 Pt D:484-490 (1982).
Varma et al., "Stoichiometric Flux Balance Models Quantitatively Predice Growth and Metabolic By-Product Secretion in Wild-Type *Escherichia coli* W3110," *Appl. Env. Microbiol.* 60(10):3724-3731 (1994).
Varma et al., "Biochemical Production Capabilities of *Escherichia coli*," *Biotechnol. Bioeng.* 42:59-73 (1993).
Varma et al., "Stoichiometric Interpretation of *Escherichia coli* Glucose Catabolism under Various Oxygenation Rates," *Appl. Environ. Microbiol.* 59:2465-2473 (1993).
Vernal et al., "Cloning and heterologous expression of a broad specificity aminotransferase of Leishmania mexicana promastigotes," *FEMS Microbiol. Lett.* 229:217-222 (2003).
Vernal et al., "Isolation partial characterization of a broad specificity aminotransferase from leishmania mexicana promastigotes," *Mol. Biochem. Parasitol.* 96:83-92 (1998).
Voellmy et al., "Role of 4-Aminobutyrate Aminotransferase in the Arginine Metabolism of Pseudomonas aeruginosa," *J. Bacteriol.* 128(3):722-729 (1976).
Walter et al., "Sequence and arrangement of two genes of the butyrate-synthesis pathway of Clostridium acetobutylicum ATCC 824," *Gene* 134(1): 107-111 (1993).

(56) References Cited

OTHER PUBLICATIONS

Wang et al., "Molecular cloning and functional identification of a novel phenylacetyl-CoA ligase gene from Penicillium chrysogenum," *Biochem. Biopyhs. Res. Commun* 360(2):453-458 (2007).

Wang et al., "Genome-scale in silico aided metabolic analysis and flux comparisons of *Escherichia coli* to improve succinate production," *Appl. Microbiol. Biotechnol.* 73(4):887-894 (2006).

Watanabe et al., "A novel α-ketoglutaric semialdehyde dehydrogenase: evolutionary insight into an alternative pathway of bacterial 1-arabinose metabolism," *J. Biol. Chem.* 281(39):28876-28888 (2006).

Westin et al., "The identification of a succinyl-CoA thioesterase suggests a novel pathway for succinate production in peroxisomes," *J. Biol. Chem.* 280(46):38125-38132 (2005).

Wilks et al., "Designs for a Broad Substrate Specificity Keto Acid Dehydrogenase," *Biochemistry* 29:8587-8591 (1990).

Willke et al., "Industrial bioconversion of renewable resources as an alternative to conventional chemistry," *Appl. Microbiol. Biotechnol* 66(2):131-142 (2004).

Winzer et al., "Differential regulation of two thiolase genes from Clostridium acetobutylicum DSM 792," *J. Mol. Microbiol. Biotechnol.* 2(4):531-541 (2000).

Wu et al., "Microbial synthesis of cis-cis-muconic acid by *Sphingobacterium* sp. GcG generated from effluent of a styrene monomer (SM) production plant," *Enzyme Microbial Tech*. 35:598-604 (2004).

Yabutani et al., "Analysis of β-ketothiolase and acetoacetyl-CoA reductase genes of a methylotrophic bacterium, Paracoccus denitrificans, and their expression in *Escherichia coli*," *FEMS Microbiol. Lett.* 133:85-90 (1995).

Yan et al., "Coenzyme A-acylating aldehyde dehydrogenase from Clostridium beijerinckii NRRL B692," *Appl. Environ. Microbiol.* 56:2591-2599 (1990).

Yang et al., "Nucleotide sequence of the fadA gene. Primary structure of 3-ketoacyl-Coenzyme A thiolase from *Escherichia coli* and the structural organization of the fadAB operon," *J. Biol. Chem.* 265(18):10424-10429 (1990).

Yang et al., "Nucleotide sequence of the fadA gene. Primary structure of 3-ketoacyl-Coenzyme A thiolase from *Escherichia coli* and the structural organization of the fadAB operon," J. Biol. Chem. 266(24):16255 (1991).

Yang et al., "Nucleotide sequence of the promoter and fadB gene of the fadBA operon and primary structure of the multifunctional fatly acid oxidation protein from *Escherichia coli*," *Biochem*. 30(27):6788-6795 (1991).

Yang et al., "The effects of feed and intracellular pyruvate levels on the redistribution of metabolic fluxes in *Escherichia coli*," *Metab Eng* 3(2):115-123 (2001).

Yang, et al., "Effect of inactivation of nuo and ackA-pta on redistribution of metabolic fluxes in *Escherichia coli*," *Biotechnol Bioeng*, 65(3):291-297 (1999).

Yang, et al., "Redistribution of Metabolic Fluxes in *Escherichia coli* with Fermentative Lactate Dehydrogenase Overexpression and Deletion," *Metab. Eng.* 1:141-152 (1999).

Yeh et al., "Evolutionarily Homologous α2β2 Oligomeric Structures in β-Ketoadipate Succinyl-CoA Transferases from Acinetobacter calcoaceticus and Pseudomonas putida," *J. Biol. Chem*. 256(4):1565-1569 (1981).

Yun et al., "The genes for anabolic 2-oxoglutarate: ferredoxin oxidoreductse from hydrogenobacter thermophilus TK-6," *Biochem. Biophys. Res. Commun.* 282(2):589-594 (2001).

Yun et al., "Enhancement of lactate and succinate formation in adhE or pta-ackA mutants of NADH dehydrogenase-deficient *Escherichia coli*," *J. Appl. Microbiol*. 99(6):1404-1412 (2005).

Zeikus et al., "Biotechnology of succinic acid production and markets for derived industrial products," *Appl. Microbiol. Biotechnol.* 51: 545-552 (1999).

Zhang et al., "Genes encoding acyl-CoA dehydrogenase (AcdH) homologues from Streptomyces coelicolor and *Streptomyces avermitilis* provide insights into the metabolism of small branched-chain fayy acids and marcrolide antibiotic production," *Microbiol*. 145 (Pt 9):2323-2334 (1999).

Zhao et al., "A novel a-ketoglutarate reductase activity of the serA-encoded 3-phosphoglycerate dehydrogenase of *Escherichia coli* K-12 and its possible implications for human 2-hydroxyglutaric aciduria," *J. Bacteriol*. 178(1):232-239 (1996).

Zhuang et al., "The YbgC protein encoded by the ybgC gene of the tol-pal gene cluster of Haemophilus influenzae catalyzes acyl-Coenzyme A thioester hydrolysis," *FEBS Lett*. 516(1-3):161-163 (2002).

Kim et al., "Synthesis of medium-chain length (C6-C10) fuels and chemicals via β-oxidation reversal in *Escherichia coli*," *J. Ind. Microbiol. Biotechnol.*, 42(3):465-475 (2015).

Kruyer et al., "Metabolic engineering strategies to bio-adipic acid production," *Curr. Opin. Biotechnol.*, 45:136-143 (2017).

Yu et al., "Direct biosynthesis of adipic acid from a synthetic pathway in recombinant *Escherichia coli*," *Biotechnol, Bioeng*., 111(12):2580-2586 (2014).

U.S. Appl. No. 12/413,355, 2009/0305364, filed Mar. 27, 2009, Nashaat T. Nashed, Microorganisms for the Production of Adipic Acid and Other Compounds, Issued U.S. Pat. No. 7,799,545.

U.S. Appl. No. 12/875,084, 2010/0330626, filed Sep. 2, 2010, Nashaat T. Nashed, Microorganisms for the Production of Adipic Acid and Other Compounds, Issued U.S. Pat. No. 8,088,607.

U.S. Appl. No. 13/088,256, 2011/0195466, filed Apr. 15, 2011, Nashaat T. Nashed, Microorganisms for the Production of Adipic Acid and Other Compounds, Issued U.S. Pat. No. 8,062,871.

U.S. Appl. No. 13/288,699, 2012/0115194, filed Nov. 3, 2011, Nashaat T. Nashed, Microorganisms for the Production of Adipic Acid and Other Compounds, Issued U.S. Pat. No. 8,216,814.

U.S. Appl. No. 13/452,642, 2012/0264179, filed Apr. 20, 2012, Nashaat T. Nashed, Microorganisms for the Production of Adipic Acid and Other Compounds, Abandoned.

U.S. Appl. No. 13/525,129, 2013/0095540, filed Jun. 15, 2012, Nashaat T. Nashed, Microorganisms for the Production of Adipic Acid and Other Compounds, Issued U.S. Pat. No. 8,592,189.

U.S. Appl. No. 13/525,133, 2012/0309062, filed Jun. 15, 2012, Nashaat T. Nashed, Microorganisms for the Production of Adipic Acid and Other Compounds, Abandoned.

U.S. Appl. No. 14/450,150, 2015/0167028, filed Aug. 1, 2014, Nashaat T. Nashed, Microorganisms for the Production of Adipic Acid and Other Compounds, Issued U.S. Pat. No. 9,382,556.

U.S. Appl. No. 15/184,940, 2017-0130234, filed Jun. 16, 2016, Todd Matthew Epstein, Microorganisms for the Production of Adipic Acid and Other Compounds, Issued Patent No. 10,415,042.

U.S. Appl. No. 12/776,365, 2010/0317069, filed May 7, 2010, Iqbal Hossain Chowdhury, Microorganisms and Methods for the Biosynthesis of Adipate, Hexamethylenediamine and 6-Aminocaproic Acid, Issued U.S. Pat. No. 8,377,680.

U.S. Appl. No. 13/549,239, 2012/0282661, filed Jul. 13, 2012, Iqbal Hossain Chowdhury, Microorganisms and Methods for the Biosynthesis of Adipate, Hexamethylenediamine and 6-Aminocaproic Acid, Abandoned.

U.S. Appl. No. 13/730,612, 2013/0303723, filed Dec. 28, 2012, Iqbal Hossain Chowdhury, Microorganisms and Methods for the Biosynthesis of Adipate, Hexamethylenediamine and 6-Aminocaproic Acid, Issued U.S. Pat. No. 9,458,480.

U.S. Appl. No. 15/263,149, 2017/0218414, filed Sep. 12, 2016, Iqbal Hossain Chowdhury, Microorganisms and Methods for the Biosynthesis of Adipate, Hexamethylenediamine and 6-Aminocaproic Acid, Issued Patent No. 10,150,977.

2019-0330670 Dec. 7, 2018 Iqbal Hossain Chowdhury Microorganisms and Methods for the Biosynthesis of Adipate, Hexamethylenediamine and 6-Aminocaproic Acid Pending.

Cheng et al., "Biological conversion of cyclic alkanes and cyclic alcohols into dicarboxylic acids: biochemical and molecular basis," *Appl. Microbiol. Biotechnol.*,58:704-711 (2002).

Doble et al, "Industrial Examples," *Green Chemistry and Process*, Academic Press, Elsevier, Boston, Ma, pp. 245-296 (2007).

(56) References Cited

OTHER PUBLICATIONS

Hershberger, "Caprolactam Pathway Map," http://eawag-bbd.ethz.ch/cap/cap_map.html (1998).

* cited by examiner

MICROORGANISMS FOR THE PRODUCTION OF ADIPIC ACID AND OTHER COMPOUNDS

This application is a continuation of U.S. application Ser. No. 15/184,940, filed Jun. 16, 2016, which is a continuation of U.S. application Ser. No. 14/450,150, filed Aug. 1, 2014, now U.S. Pat. No. 9,382,556, issued Jul. 5, 2016, which is a continuation of U.S. application Ser. No. 13/452,642, filed Apr. 20, 2012, which is a continuation of U.S. application Ser. No. 13/288,699, filed Nov. 3, 2011, now U.S. Pat. No. 8,216,814, issued Jul. 10, 2012, which is a continuation of U.S. application Ser. No. 13/088,256, filed Apr. 15, 2011, now U.S. Pat. No. 8,062,871, issued Nov. 22, 2011, which is a continuation of U.S. application Ser. No. 12/875,084, filed Sep. 2, 2010, now U.S. Pat. No. 8,088,607, issued Jan. 3, 2012, which is a continuation of U.S. application Ser. No. 12/413,355, filed Mar. 27, 2009, now U.S. Pat. No. 7,799,545, issued Sep. 21, 2010, which claims the benefit of priority of U.S. Provisional Ser. No. 61/040,059, filed Mar. 27, 2008, each of which the entire contents are incorporated herein by reference.

BACKGROUND OF THE INVENTION

The present invention relates generally to biosynthetic processes, and more specifically to organisms having adipic acid, 6-aminocaproic acid and caprolactam biosynthetic capability.

Adipic acid, a dicarboxylic acid, with molecular weight of 146.14, is a compound of commercial significance. Its major use is to produce nylon 6,6, a linear polyamide made by condensing adipic acid with hexamethylene diamine that is primarily employed for manufacturing different kinds of fibers. Other uses of adipic acid include its use in plasticizers, unsaturated polyesters, and polyester polyols. Additional uses include for production of polyurethane, lubricant components, and as a food ingredient as a flavorant and gelling aid.

Historically, adipic acid was prepared from various fats using oxidation. The current commercial processes for adipic acid synthesis rely on the oxidation of KA oil, a mixture of cyclohexanone, the ketone or K component, and cyclohexanol, the alcohol or A component, or of pure cyclohexanol using an excess of strong nitric acid. There are several variations of this theme which differ in the routes for production of KA or cyclohexanol. For example, phenol is an alternative raw material in KA oil production, and the process for the synthesis of adipic acid from phenol has been described. The other versions of this process tend to use oxidizing agents other than nitric acid, such as hydrogen peroxide, air or oxygen.

Caprolactam is an organic compound which is a lactam of 6-aminohexanoic acid (ε-aminohexanoic acid, aminocaproic acid). It can alternatively be considered cyclic amide of caproic acid. The primary industrial use of caprolactam is as a monomer in the production of nylon-6. Most of the caprolactam is synthesised from cyclohexanone via an oximation process using hydroxylammonium sulfate followed by catalytic rearrangement using the Beckmann rearrangement process step.

Thus, there exists a need for alternative methods for effectively producing commercial quantities of compounds such as adipic acid and carpolactam. The present invention satisfies this need and provides related advantages as well.

SUMMARY OF INVENTION

The invention provides a non-naturally occurring microbial organism having an adipate, 6-aminocaproic acid or caprolactam pathway. The microbial organism contains at least one exogenous nucleic acid encoding an enzyme in the respective adipate, 6-aminocaproic acid or caprolactam pathway. The invention additionally provides a method for producing adipate, 6-aminocaproic acid or caprolactam. The method can include culturing an adipate, 6-aminocaproic acid or caprolactam producing microbial organism, where the microbial organism expresses at least one exogenous nucleic acid encoding an adipate, 6-aminocaproic acid or caprolactam pathway enzyme in a sufficient amount to produce the respective product, under conditions and for a sufficient period of time to produce adipate, 6-aminocaproic acid or caprolactam.

DETAILED DESCRIPTION OF THE INVENTION

Figure 1:
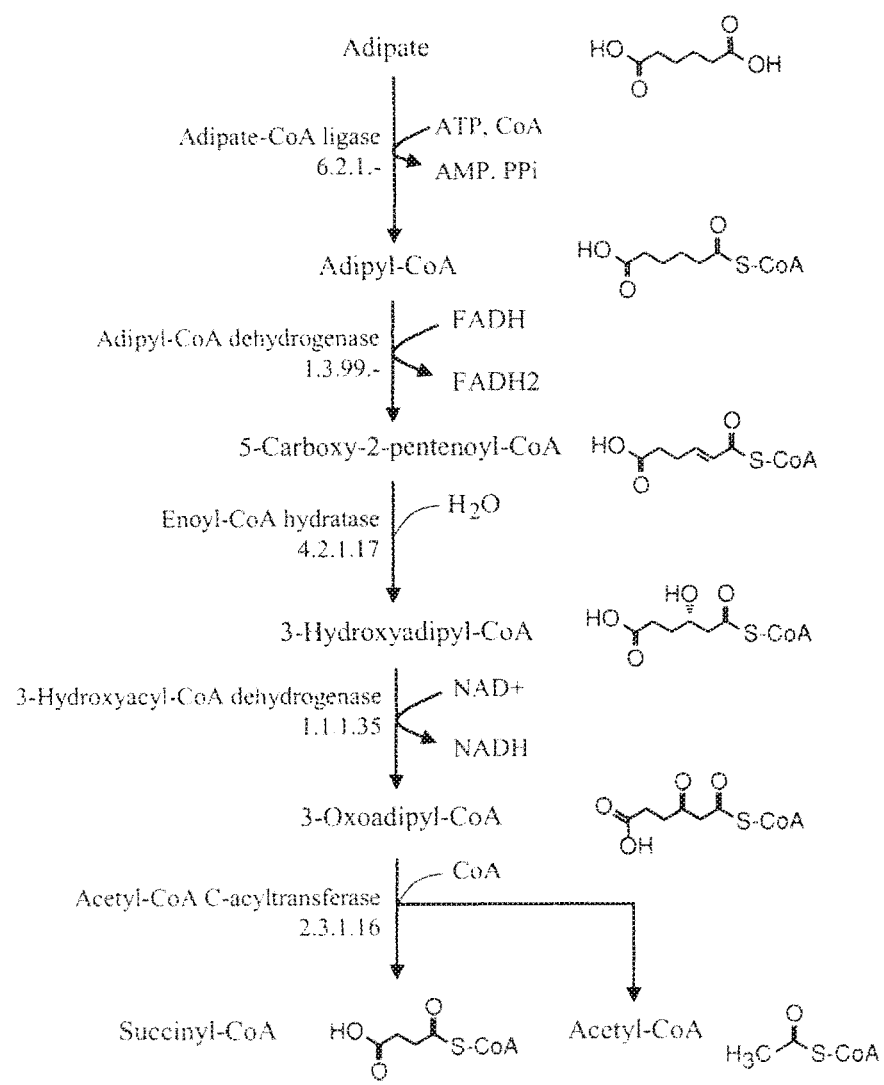
FIG. 1 shows an exemplary pathway for adipate degradation in the peroxisome of *Penicillium chrysogenum*.

The present invention is directed to the design and production of cells and organisms having biosynthetic production capabilities for adipate, 6-aminocaproic acid or caprolactam. The results described herein indicate that metabolic pathways can be designed and recombinantly engineered to achieve the biosynthesis of adipate, 6-aminocaproic acid or caprolactam in *Escherichia coli* and other cells or organisms. Biosynthetic production of adipate, 6-aminocaproic acid and caprolactam can be confirmed by construction of strains having the designed metabolic genotype. These metabolically engineered cells or organisms also can be subjected to adaptive evolution to further augment adipate, 6-aminocaproic acid or caprolactam biosynthesis, including under conditions approaching theoretical maximum growth.

As disclosed herein, a number of metabolic pathways for the production of adipate, 6-aminocaproate, and caprolactam are described. Two routes, the reverse adipate degradation pathway and the 3-oxoadipate pathway, were found to be beneficial with respect to (i) the adipate yields (92% molar yield on glucose), (ii) the lack of oxygen requirement for adipate synthesis, (iii) the associated energetics, and (iv) the theoretical capability to produce adipate as the sole fermentation product. Metabolic pathways for adipate production that pass through α-ketoadipate or lysine are also described but are lower yielding and require aeration for maximum production. A pathway for producing either or both of 6-aminocaproate and caprolactam from adipyl-CoA, a precursor in the reverse degradation pathway, is also disclosed herein.

As disclosed herein, a number of exemplary pathways for biosynthesis of adipate are described. One exemplary pathway involves adipate synthesis via a route that relies on the reversibility of adipate degradation as described in organisms such as *P. chrysogenum* (see Examples I and II). A second exemplary pathway entails the formation of 3-oxoadipate followed by its reduction, dehydration and again reduction to form adipate (see Examples III and IV). The adipate yield using either of these two pathways is 0.92 moles per mole glucose consumed. The uptake of oxygen is not required for attaining these theoretical maximum yields, and the energetics under anaerobic conditions are favorable for growth and product secretion. A method for producing adipate from glucose-derived cis,cis-muconic acid was described previously (Frost et al., U.S. Pat. No. 5,487,987, issued Jan. 30, 1996) (see Example V). Advantages of the embodiments disclosed herein over this previously described method are discussed. Metabolic pathways for adipate production that pass through α-ketoadipate (Example VI) or lysine (Example VII) precursors are lower yielding and require aeration for maximum production. A pathway for producing either or both of 6-aminocaproate and caprolactam from adipyl-CoA, a precursor in the reverse degradation pathway, is described (see Example VIII and IX). Additional pathways for producing adipate are described in Examples X and XI. Exemplary genes and enzymes required for constructing microbes with these capabilities are described as well as methods for cloning and transformation, monitoring product formation, and using the engineered microorganisms for production.

As disclosed herein, six different pathways for adipic acid synthesis using glucose/sucrose as a carbon substrate are described. For all maximum yield calculations, the missing reactions in a given pathway were added to the *E. coli* stoichiometric network in SimPheny that is similar to the one described previously (Reed et al., *Genome Biol.* 4:R54 (2003)). Adipate is a charged molecule under physiological conditions and was assumed to require energy in the form of a proton-based symport system to be secreted out of the network. Such a transport system is thermodynamically feasible if the fermentations are carried out at neutral or near-neutral pH. Low pH adipic acid formation would require an ATP-dependant export mechanism, for example, the ABC system as opposed to proton symport. The reactions in the pathways and methods of implementation of these pathways are described in Examples I-XI.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes within an adipate, 6-aminocaproic acid or caprolactam biosynthetic pathway.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, "adipate," having the chemical formula —OOC—$(CH_2)_4$—COO— (see FIG. 2) (IUPAC name hexanedioate), is the ionized form of adipic acid (IUPAC name hexanedioic acid), and it is understood that adipate and adipic acid can be used interchangeably throughout to refer to the compound in any of its neutral or ionized forms, including any salt forms thereof. It is understood by those skilled understand that the specific form will depend on the pH.

As used herein, "6-aminocaproate," having the chemical formula —OOC—$(CH_2)_5$—$NH_2$ (see FIG. 8), is the ionized form of 6-aminocaproic acid (IUPAC name 6-aminohexanoic acid), and it is understood that 6-aminocaproate and 6-aminocaproic acid can be used interchangeably throughout to refer to the compound in any of its neutral or ionized forms, including any salt forms thereof. It is understood by those skilled understand that the specific form will depend on the pH.

Figure 8:
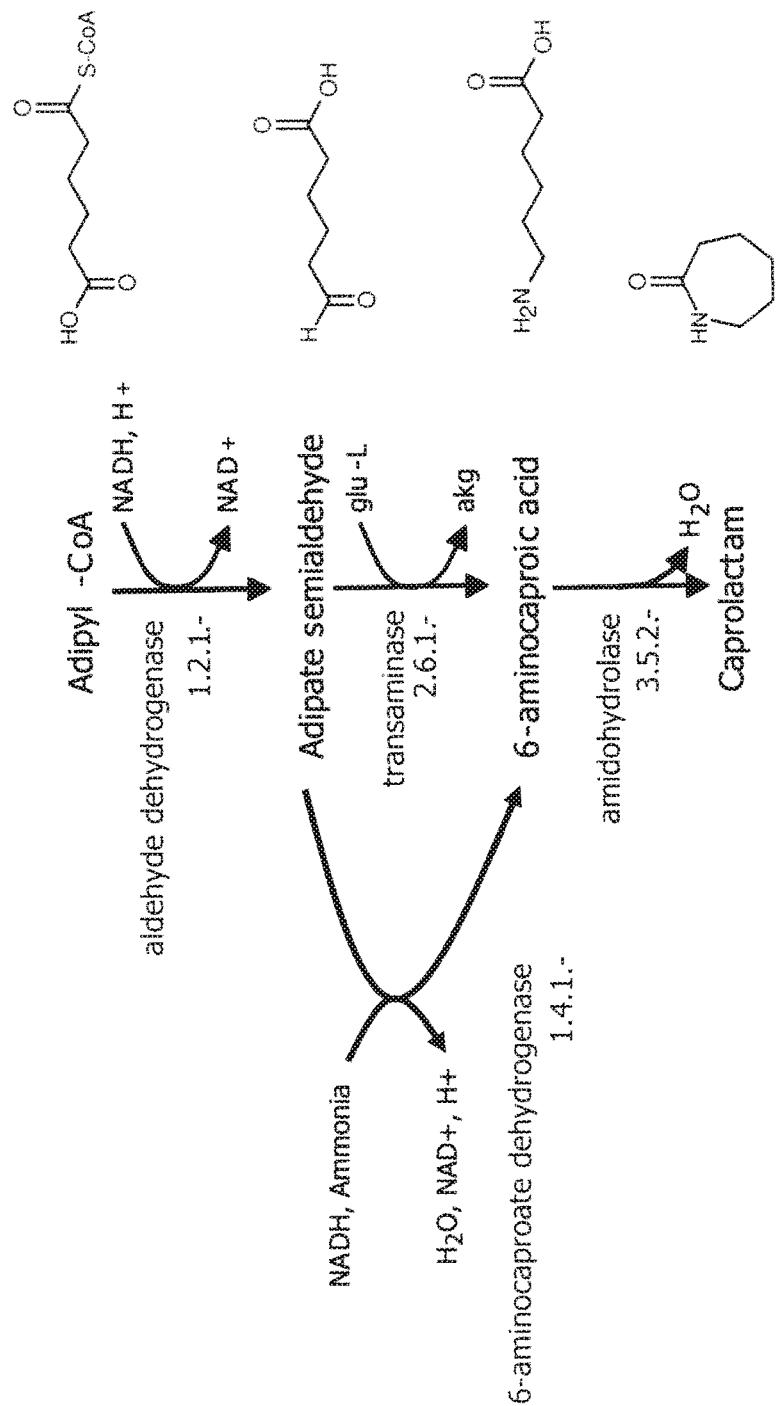
FIG. 8 shows an exemplary caprolactam synthesis pathway using adipyl-CoA as a starting point.

As used herein, "caprolactam" (IUPAC name azepan-2-one) is a lactam of 6-aminohexanoic acid (see FIG. 8).

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of *mycoplasma* 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having adipate, 6-aminocaproic acid or caprolactam biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

The invention provides non-naturally occurring microbial organisms capable of producing adipate, 6-aminocaproic acid or caprolactam. For example, an adipate pathway can be a reverse adipate degradation pathway (see Examples I and II). In one embodiment, the invention provides a non-naturally occurring microbial organism having an adipate pathway comprising at least one exogenous nucleic acid encoding an adipate pathway enzyme expressed in a sufficient amount to produce adipate, the adipate pathway comprising succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA synthetase or phosphotransadipylase/adipate kinase or adipyl-CoA:acetyl-CoA transferase or adipyl-CoA hydrolase. In addition, an adipate pathway can be through a 3-oxoadipate pathway (see Examples III and IV). In another embodiment, the invention provides a non-naturally occurring microbial organism having an adipate pathway comprising at least one exogenous nucleic acid encoding an adipate pathway enzyme expressed in a sufficient amount to produce adipate, the adipate pathway comprising succinyl-CoA:acetyl-CoA acyl transferase, 3-oxoadipyl-CoA transferase, 3-oxoadipate reductase, 3-hydroxyadipate dehydratase, and 2-enoate reductase.

In still another embodiment, the invention provides a non-naturally occurring microbial organism having a 6-aminocaproic acid pathway comprising at least one exogenous nucleic acid encoding a 6-aminocaproic acid pathway enzyme expressed in a sufficient amount to produce 6-aminocaproic acid, the 6-aminocaproic acid pathway comprising CoA-dependent aldehyde dehydrogenase and transaminase (see Examples VIII and IX). Alternatively, 6-aminocaproate dehydrogenase can be used to convert adipate semialdehyde to form 6-aminocaproate (see FIG. 8). In a further embodiment, the invention provides a non-naturally occurring microbial organism having a caprolactam pathway comprising at least one exogenous nucleic acid encoding a caprolactam pathway enzyme expressed in a sufficient amount to produce caprolactam, the caprolactam pathway comprising CoA-dependent aldehyde dehydrogenase, transaminase or 6-aminocaproate dehydrogenase, and amidohydrolase (see Examples VIII and IX).

As disclosed herein, a 6-aminocaproic acid or caprolactam producing microbial organism of the invention can produce 6-aminocaproic acid and/or caprolactam from an adipyl-CoA precursor (see FIG. 8 and Examples VIII and IX). Therefore, it is understood that a 6-aminocaproic acid or caprolactam producing microbial organism can further include a pathway to produce adipyl-CoA. For example an adipyl-CoA pathway can include the enzymes of FIG. 2 that utilize succinyl-CoA and acetyl-CoA as precursors through the production of adipyl-CoA, that is, lacking an enzyme for the final step of converting adipyl-CoA to adipate. Thus, one exemplary adipyl-CoA pathway can include succinyl-CoA: acetyl-CoA acyl transferase, 3-hydroxyacyl-CoA dehydrogenase, 3-hydroxyadipyl-CoA dehydratase and 5-carboxy-2-pentenoyl-CoA reductase.

In addition, as shown in FIG. 1, an adipate degradation pathway includes the step of converting adipate to adipyl-CoA by an adipate CoA ligase. Therefore, an adipyl-CoA pathway can be an adipate pathway that further includes an enzyme activity that converts adipate to adipyl-CoA, including, for example, adipate-CoA ligase activity as in the first step of FIG. 1 or any of the enzymes in the final step of FIG.

2 carried out in the reverse direction, for example, any of adipyl-CoA synthetase (also referred to as adipate Co-A ligase), phosphotransadipylase/adipate kinase, adipyl-CoA: acetyl-CoA transferase or adipyl-CoA hydrolase. An enzyme having adipate to adipyl-CoA activity can be an endogenous activity or can be provided as an exogenous nucleic acid encoding the enzyme, as disclosed herein. Thus, it is understood that any adipate pathway can be utilized with an adipate to adipyl-CoA enzymatic activity to generate an adipyl-CoA pathway. Such a pathway can be included in a 6-aminocaproic acid or caprolactam producing microbial organism to provide an adipyl-CoA precursor for 6-aminocaproic acid and/or caprolactam production.

Figure 6:
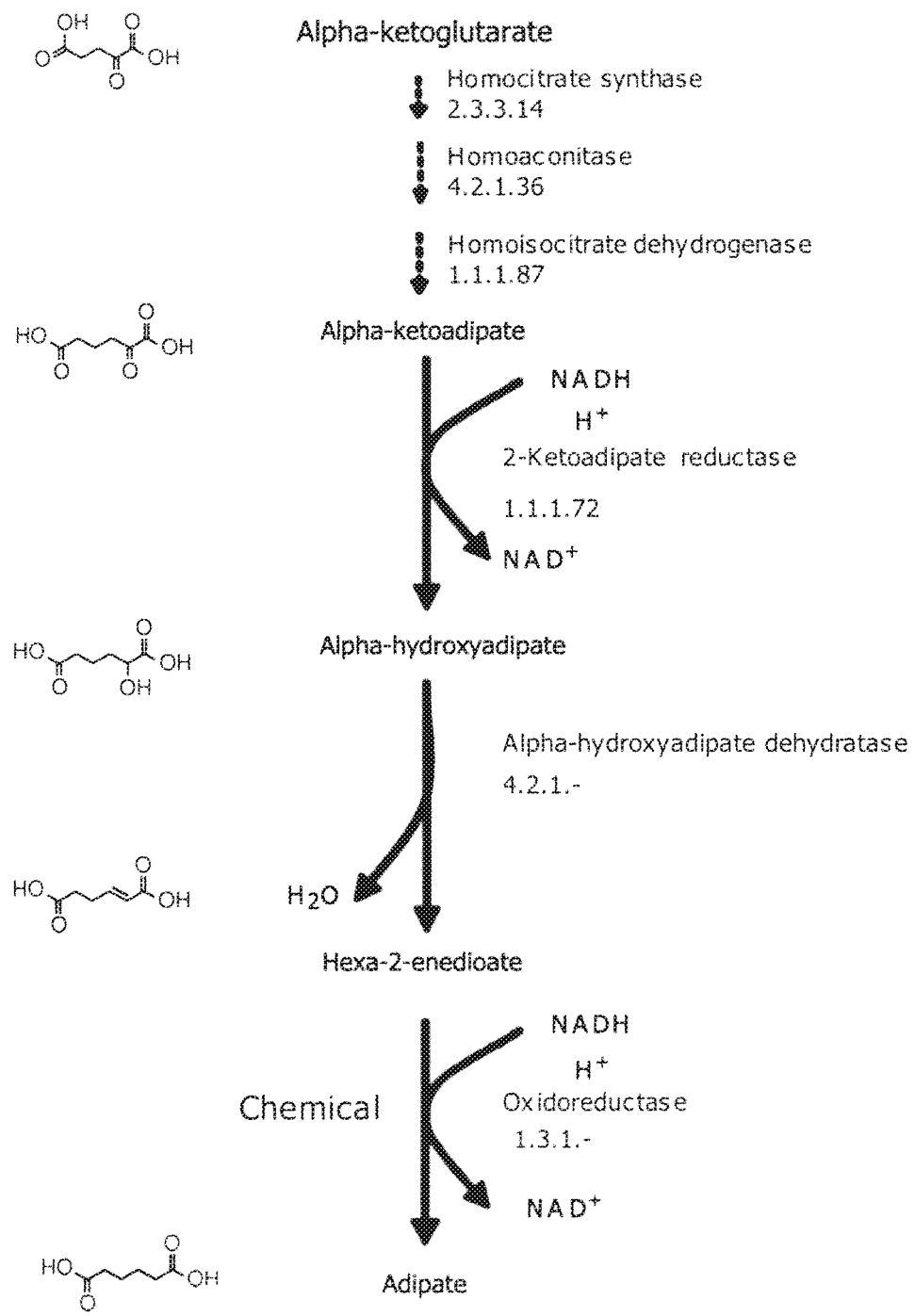
FIG. 6 shows an exemplary pathway for adipate synthesis via alpha-ketoadipate using alpha-ketoglutarate as a starting point.

An additional exemplary adipate pathway utilizes alpha-ketoadipate as a precursor (see FIG. 6 and Example VI). In yet another embodiment, the invention provides a non-naturally occurring microbial organism having an adipate pathway comprising at least one exogenous nucleic acid encoding an adipate pathway enzyme expressed in a sufficient amount to produce adipate, the adipate pathway comprising homocitrate synthase, homoaconitase, homoisocitrate dehydrogenase, 2-ketoadipate reductase, alpha-hydroxyadipate dehydratase and oxidoreductase. A further exemplary adipate pathway utilizes a lysine dedgradation pathway (see FIG. 7 and Example VII). Another embodiment of the invention provides a non-naturally occurring microbial organism having an adipate pathway comprising at least one exogenous nucleic acid encoding an adipate pathway enzyme expressed in a sufficient amount to produce adipate, the adipate pathway comprising carbon nitrogen lyase, oxidoreductase, transaminase and oxidoreductase.

Figure 9:
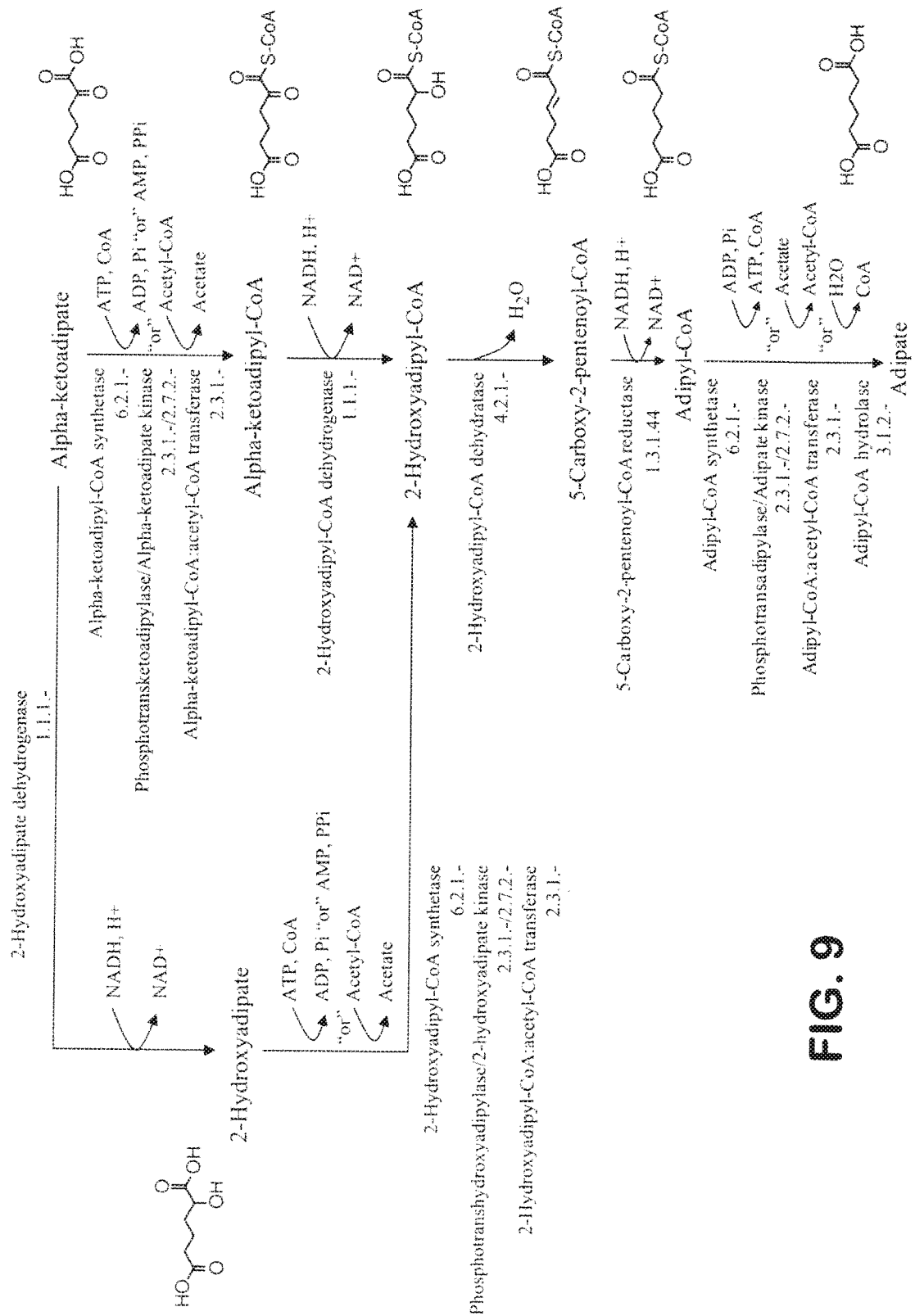
FIG. 9 shows exemplary adipate synthesis pathways using alpha-ketoadipate as a starting point.

Yet another exemplary adipate pathway utilizes alpha-ketoadipate as a precursor (see FIG. 9 and Examples X and XI). Thus, the invention additionally provides a non-naturally occurring microbial organism having an adipate pathway comprising at least one exogenous nucleic acid encoding an adipate pathway enzyme expressed in a sufficient amount to produce adipate, the adipate pathway comprising alpha-ketoadipyl-CoA synthetase, phosphotransketoadipylase/alpha-ketoadipate kinase or alpha-ketoadipyl-CoA: acetyl-CoA transferase; 2-hydroxyadipyl-CoA dehydrogenase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase. In still another embodiment, the invention provides a non-naturally occurring microbial organism having an adipate pathway comprising at least one exogenous nucleic acid encoding an adipate pathway enzyme expressed in a sufficient amount to produce adipate, the adipate pathway comprising 2-hydroxyadipate dehydrogenase; 2-hydroxyadipyl-CoA synthetase, phosphotranshydroxyadipylase/2-hydroxyadipate kinase or 2-hydroxyadipyl-CoA:acetyl-CoA transferase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase.

In an additional embodiment, the invention provides a non-naturally occurring microbial organism having an adipate, 6-aminocaproic acid or caprolactam pathway, wherein the non-naturally occurring microbial organism comprises at least one exogenous nucleic acid encoding a polypeptide that converts a substrate to a product, as disclosed herein. Thus, the invention provides a non-naturally occurring microbial organism containing at least one exogenous nucleic acid encoding a polypeptide, where the polypeptide is an enzyme or protein that converts the substrates and products of an adipate, 6-aminocaproic acid or caprolactam pathway, such as that shown in FIGS. 2, 3, 8 and 9.

Figure 2:
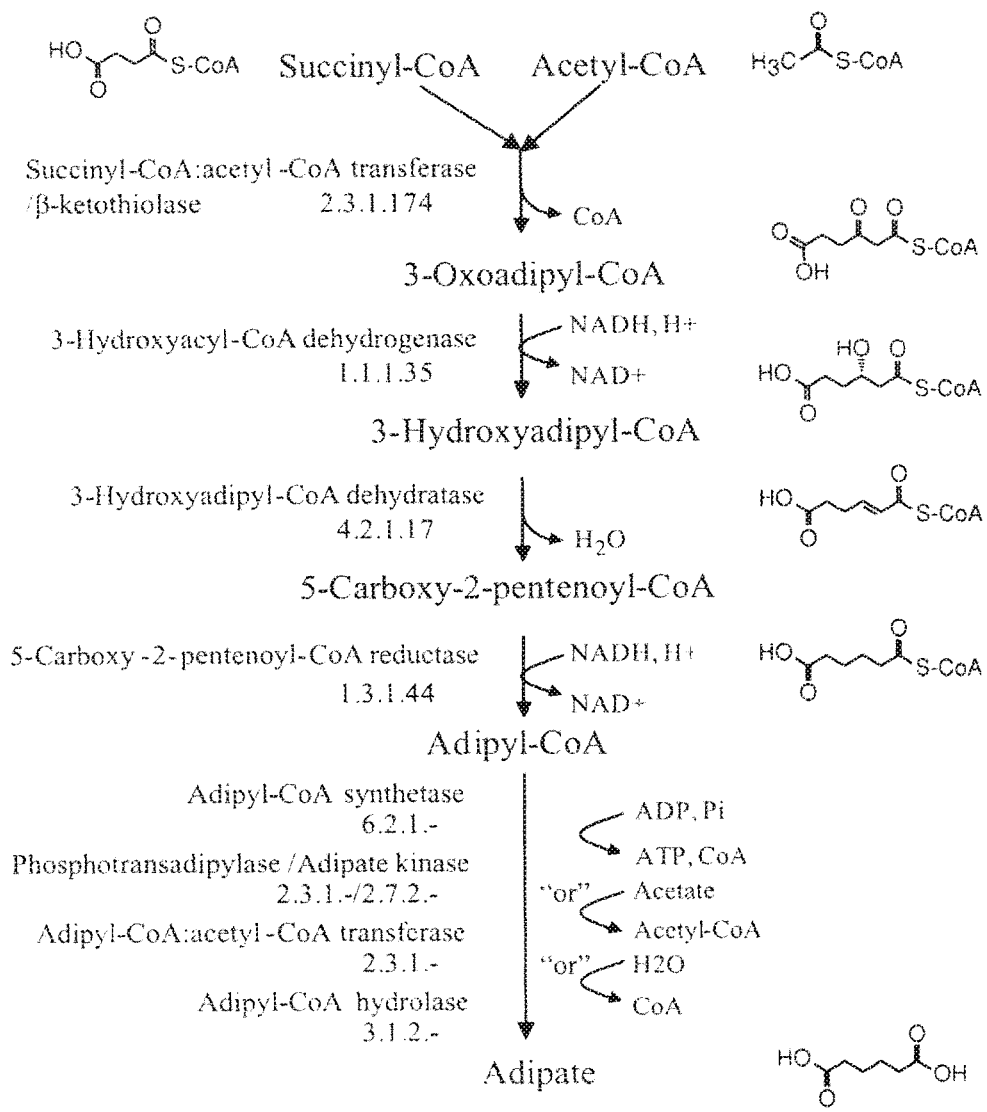
FIG. 2 shows an exemplary pathway for adipate formation via a reverse degradation pathway. Several options are provided for the final conversion of adipyl-CoA to adipate.

In one embodiment, the invention provides a non-naturally occurring microbial organism having an adipate pathway, wherein the microbial organism contains at least one exogenous nucleic acid encoding a polypeptide that converts a substrate to a product selected from succinyl-CoA and acetyl-CoA to 3-oxoadipyl-CoA; 3-oxoadipyl-CoA to 3-hydroxyadipyl-CoA; 3-hydroxyadipyl-CoA to 5-carboxy-2-pentenoyl-CoA; 5-carboxy-2-pentenoyl-CoA to adipyl-CoA; adipyl-CoA to adipate (see FIG. 2). In another embodiment, the invention provides a non-naturally occurring microbial organism having an adipate pathway, wherein the microbial organism contains at least one exogenous nucleic acid encoding a polypeptide that converts a substrate to a product selected from succinyl-CoA and acetyl-CoA to 3-oxoadipyl-CoA; 3-oxoadipyl-CoA to 3-oxoadipate; 3-oxoadipate to 3-hydroxyadipate; 3-hydroxyadipate to hexa-2-enedioate; hexa-2-enedioate to adipate (see FIG. 3).

In an additional embodiment, the invention provides a non-naturally occurring microbial organism having a 6-aminocaproic acid pathway, wherein the microbial organism contains at least one exogenous nucleic acid encoding a polypeptide that converts a substrate to a product selected from adipyl-CoA to adipate semialdehyde; and adipate semialdehyde to 6-aminocaproate (see FIG. 8). In still another embodiment, the invention provides a non-naturally occurring microbial organism having a caprolactam pathway, wherein the microbial organism contains at least one exogenous nucleic acid encoding a polypeptide that converts a substrate to a product selected from adipyl-CoA to adipate semialdehyde; adipate semialdehyde to 6-aminocaproate; and 6-aminocaproate to caprolactam.

In still another embodiment, the invention provides a non-naturally occurring microbial organism having an adipate pathway, wherein the microbial organism contains at least one exogenous nucleic acid encoding a polypeptide that converts a substrate to a product selected from alpha-ketoadipate to alpha-ketoadipyl-CoA; alpha-ketoadipyl-CoA to 2-hydroxyadipyl-CoA; 2-hydroxyadipyl-CoA to 5-carboxy-2-pentenoyl-CoA; 5-carboxy-2-pentenoyl-CoA to adipyl-CoA; and adipyl-CoA to adipate (see FIG. 9). Additionally, the invention provides a non-naturally occurring microbial organism having an adipate pathway, wherein the microbial organism contains at least one exogenous nucleic acid encoding a polypeptide that converts a substrate to a product selected from alpha-ketoadipate to 2-hydroxyadipate; 2-hydroxyadipate to 2-hydroxyadipyl-CoA; 2-hydroxyadipyl-CoA to 5-carboxy-2-pentenoyl-CoA; 5-carboxy-2-pentenoyl-CoA to adipyl-CoA; and adipyl-CoA to adipate (FIG. 9).

The invention is described herein with general reference to the metabolic reaction, reactant or product thereof, or with specific reference to one or more nucleic acids or genes encoding an enzyme associated with or catalyzing the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes as well as the reactants and products of the reaction.

The non-naturally occurring microbial organisms of the invention can be produced by introducing expressible nucleic acids encoding one or more of the enzymes participating in one or more adipate, 6-aminocaproic acid or caprolactam biosynthetic pathways. Depending on the host microbial organism chosen for biosynthesis, nucleic acids for some or all of a particular adipate, 6-aminocaproic acid or caprolactam biosynthetic pathway can be expressed. For example, if a chosen host is deficient in one or more enzymes for a desired biosynthetic pathway, then expressible nucleic acids for the deficient enzyme(s) are introduced into the host for subsequent exogenous expression. Alternatively, if the chosen host exhibits endogenous expression of some pathway genes, but is deficient in others, then an encoding nucleic acid is needed for the deficient enzyme(s) to achieve adipate, 6-aminocaproic acid or caprolactam biosynthesis. Thus, a non-naturally occurring microbial organism of the invention can be produced by introducing exogenous enzyme activities to obtain a desired biosynthetic pathway or a desired biosynthetic pathway can be obtained by introducing one or more exogenous enzyme activities that, together with one or more endogenous enzymes, produces a desired product such as adipate, 6-aminocaproic acid or caprolactam.

Depending on the adipate, 6-aminocaproic acid or caprolactam biosynthetic pathway constituents of a selected host microbial organism, the non-naturally occurring microbial organisms of the invention will include at least one exogenously expressed adipate, 6-aminocaproic acid or caprolactam pathway-encoding nucleic acid and up to all encoding nucleic acids for one or more adipate, 6-aminocaproic acid or caprolactam biosynthetic pathways. For example, adipate, 6-aminocaproic acid or caprolactam biosynthesis can be established in a host deficient in a pathway enzyme through exogenous expression of the corresponding encoding nucleic acid. In a host deficient in all enzymes of a adipate, 6-aminocaproic acid or caprolactam pathway, exogenous expression of all enzyme in the pathway can be included, although it is understood that all enzymes of a pathway can be expressed even if the host contains at least one of the pathway enzymes.

For example, exogenous expression of all enzymes in a pathway for production of adipate can be included in a host organism, such as succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA synthetase or phosphotransadipylase/adipate kinase or adipyl-CoA:acetyl-CoA transferase or adipyl-CoA hydrolase. In particular, a host organism can contain the adipate pathway enzymes succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA synthetase. Alternatively, a host organism can contain the adipate pathway enzymes succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and phosphotransadipylase/adipate kinase. In addition, a host organism can contain the adipate pathway enzymes succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA:acetyl-CoA transferase. Further, a host organism can contain the adipate pathway enzymes succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA hydrolase.

In the case of a 6-aminocaproic acid producing microbial organism, exogenous expression of all enzymes in a pathway for production of 6-aminocaproic acid can be included in a host organism, such as CoA-dependent aldehyde dehydrogenase and transaminase or CoA-dependent aldehyde dehdrogenase and 6-aminocaproate dehydrogenase. For a caprolactam producing microbial organism, exogenous expression of all enzymes in a pathway for production of caprolactam can be included in a host organism, such as CoA-dependent aldehyde dehydrogenase, transaminase or 6-aminocaproate dehydrogenase, and amidohydrolase.

Given the teachings and guidance provided herein, those skilled in the art will understand that the number of encoding nucleic acids to introduce in an expressible form will, at least, parallel the adipate, 6-aminocaproic acid or caprolactam pathway deficiencies of the selected host microbial organism. Therefore, a non-naturally occurring microbial organism of the invention can have one, two, three, four, or five, up to all nucleic acids encoding the above enzymes constituting a adipate, 6-aminocaproic acid or caprolactam biosynthetic pathway. In some embodiments, the non-naturally occurring microbial organisms also can include other genetic modifications that facilitate or optimize adipate, 6-aminocaproic acid or caprolactam biosynthesis or that confer other useful functions onto the host microbial organism. One such other functionality can include, for example, augmentation of the synthesis of one or more of the adipate, 6-aminocaproic acid or caprolactam pathway precursors such as succinyl-CoA and/or acetyl-CoA in the case of adipate synthesis, or adipyl-CoA in the case of 6-aminocaproic acid or caprolactam synthesis, including the adipate pathway enzymes disclosed herein.

In some embodiments, a non-naturally occurring microbial organism of the invention is generated from a host that contains the enzymatic capability to synthesize adipate, 6-aminocaproic acid or caprolactam. In this specific embodiment it can be useful to increase the synthesis or accumulation of an adipate, 6-aminocaproic acid or caprolactam pathway product to, for example, drive adipate, 6-aminocaproic acid or caprolactam pathway reactions toward adipate, 6-aminocaproic acid or caprolactam production. Increased synthesis or accumulation can be accomplished by, for example, overexpression of nucleic acids encoding one or more of the above-described adipate, 6-aminocaproic acid or caprolactam pathway enzymes. Over expression of the adipate, 6-aminocaproic acid or caprolactam pathway enzyme or enzymes can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing adipate, 6-aminocaproic acid or caprolactam, through overexpression of one, two, three, four, five, that is, up to all nucleic acids encoding adipate, 6-aminocaproic acid or caprolactam biosynthetic pathway enzymes. In addition, a non-naturally occurring organism can be generated by mutagenesis of an endogenous gene that results in an increase in activity of an enzyme in the adipate, 6-aminocaproic acid or caprolactam biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, an adipate, 6-aminocaproic acid or caprolactam biosynthetic pathway onto the microbial organism. Alternatively, encoding nucleic acids can be introduced to produce an intermediate microbial organism having the biosynthetic capability to catalyze some of the required reactions to confer adipate, 6-aminocaproic acid or caprolactam biosynthetic capability. For example, a non-naturally occurring microbial organism having an adipate, 6-aminocaproic acid or caprolactam biosynthetic pathway can comprise at least two exogenous nucleic acids encoding desired enzymes. In the case of adipate production, the at least two exogenous nucleic acids can encode the enzymes such as the combination of succinyl-CoA:acetyl-CoA acyl transferase and 3-hydroxyacyl-CoA dehydrogenase, or succinyl-CoA:acetyl-CoA acyl transferase and 3-hydroxyadipyl-CoA dehydratase, or 3-hydroxyadipyl-CoA and 5-carboxy-2-pentenoyl-CoA reductase, or 3-hydroxyacyl-CoA and adipyl-CoA synthetase, and the like. In the case of caprolactam production, the at least two exogenous nucleic acids can encode the enzymes such as the combination of CoA-dependent aldehyde dehydrogenase and transaminase, or CoA-dependent aldehyde dehydrogenase and amidohydrolase, or transaminase and amidohydrolase. Thus, it is understood that any combination of two or more enzymes of a biosynthetic pathway can be included in a non-naturally occurring microbial organism of the invention.

Similarly, it is understood that any combination of three or more enzymes of a biosynthetic pathway can be included in a non-naturally occurring microbial organism of the invention, for example, in the case of adipate production, the combination of enzymes succinyl-CoA:acetyl-CoA acyl transferase, 3-hydroxyacyl-CoA dehydrogenase, and 3-hydroxyadipyl-CoA dehydratase; or succinyl-CoA:acetyl-CoA acyl transferase, 3-hydroxyacyl-CoA dehydrogenase and 5-carboxy-2-pentenoyl-CoA reductase; or succinyl-CoA:acetyl-CoA acyl transferase, 3-hydroxyacyl-CoA dehydrogenase and adipyl-CoA synthetase; or 3-hydroxyacyl-CoA dehydrogenase, 3-hydroxyadipyl-CoA dehydratase and adipyl-CoA:acetyl-CoA transferase, and so forth, as desired, so long as the combination of enzymes of the desired biosynthetic pathway results in production of the corresponding desired product. Similarly, any combination of four or more enzymes of a biosynthetic pathway as disclosed herein can be included in a non-naturally occurring microbial organism of the invention, as desired, so long as the combination of enzymes of the desired biosynthetic pathway results in production of the corresponding desired product.

In addition to the biosynthesis of adipate, 6-aminocaproic acid or caprolactam as described herein, the non-naturally occurring microbial organisms and methods of the invention also can be utilized in various combinations with each other and with other microbial organisms and methods well known in the art to achieve product biosynthesis by other routes. For example, one alternative to produce adipate, 6-aminocaproic acid or caprolactam other than use of the adipate, 6-aminocaproic acid or caprolactam producers is through addition of another microbial organism capable of converting an adipate, 6-aminocaproic acid or caprolactam pathway intermediate to adipate, 6-aminocaproic acid or caprolactam. One such procedure includes, for example, the fermentation of a microbial organism that produces an adipate, 6-aminocaproic acid or caprolactam pathway intermediate. The adipate, 6-aminocaproic acid or caprolactam pathway intermediate can then be used as a substrate for a second microbial organism that converts the adipate, 6-aminocaproic acid or caprolactam pathway intermediate to adipate, 6-aminocaproic acid or caprolactam. The adipate, 6-aminocaproic acid or caprolactam pathway intermediate can be added directly to another culture of the second organism or the original culture of the adipate, 6-aminocaproic acid or caprolactam pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, adipate, 6-aminocaproic acid or caprolactam. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of adipate, 6-aminocaproic acid or caprolactam can be accomplished by constructing a microbial organism that contains biosynthetic pathways for conversion of one pathway intermediate to another pathway intermediate or the product. Alternatively, adipate, 6-aminocaproic acid or caprolactam also can be biosynthetically produced from microbial organisms through co-culture or co-fermentation using two organisms in the same vessel, where the first microbial organism produces a adipate, 6-aminocaproic acid or caprolactam intermediate and the second microbial organism converts the intermediate to adipate, 6-aminocaproic acid or caprolactam.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce adipate, 6-aminocaproic acid or caprolactam.

Sources of encoding nucleic acids for an adipate, 6-aminocaproic acid or caprolactam pathway enzyme can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Pseudomonas knackmussii, Pseudomonas putida, Pseudomonas fluorescens, Klebsiella pneumoniae, Serratia proteamaculans, Streptomyces* sp. 2065, *Pseudomonas aeruginosa, Ralstonia eutropha, Clostridium acetobutylicum, Euglena gracilis, Treponema denticola, Clostridium kluyveri, Homo sapiens, Rattus norvegicus, Acinetobacter* sp. ADP 1, *Streptomyces coelicolor, Eubacterium barkeri, Peptostreptococcus asaccharolyticus, Clostridium botulinum, Clostridium tyrobutyricum, Clostridium thermoaceticum* (*Moorella thermoaceticum*), *Acinetobacter calcoaceticus, Mus musculus, Sus scrofa, Flavobacterium* sp, *Arthrobacter aurescens, Penicillium chrysogenum, Aspergillus niger, Aspergillus nidulans, Bacillus subtilis, Saccharomyces cerevisiae, Zymomonas mobilis, Mannheimia succiniciproducens, Clostridium ljungdahlii, Clostridium carboxydivorans, Geobacillus stearothermophilus, Agrobacterium tumefaciens, Achromobacter* denitrificans, *Arabidopsis thaliana, Haemophilus influenzae, Acidaminococcus fermentans, Clostridium* sp. M62/1, *Fusobacterium nucleatum*, as well as other exemplary species disclosed herein or available as source organisms for corresponding genes (see Examples). However, with the complete genome sequence available for now more than 550 species (with more than half of these available on public databases such as the NCBI), including 395 microorganism genomes and a variety of yeast, fungi, plant, and mammalian genomes, the identification of genes encoding the requisite adipate, 6-aminocaproic acid or caprolactam biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of adipate, 6-aminocaproic acid or caprolactam described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative adipate, 6-aminocaproic acid or caprolactam biosynthetic pathway exists in an unrelated species, adipate, 6-aminocaproic acid or caprolactam biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize adipate, 6-aminocaproic acid or caprolactam.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris.* For example, *E. coli* is a particularly useful host organisms since it is a well characterized microbial organism suitable for genetic engineering. Other particularly useful host organisms include yeast such as *Saccharomyces cerevisiae.*

Methods for constructing and testing the expression levels of a non-naturally occurring adipate-, 6-aminocaproic acid- or caprolactam-producing host can be performed, for example, by recombinant and detection methods well known in the art. Such methods can be found described in, for example, Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, Md. (1999).

Exogenous nucleic acid sequences involved in a pathway for production of adipate, 6-aminocaproic acid or caprolactam can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more adipate, 6-aminocaproic acid or caprolactam biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The invention additionally provides methods for producing a desired product such as adipate, 6-aminocaproic acid or caprolactam. In one embodiment, the invention provides a method for producing adipate, comprising culturing a non-naturally occurring microbial organism having an adipate pathway, the pathway comprising at least one exogenous nucleic acid encoding an adipate pathway enzyme expressed in a sufficient amount to produce adipate, under conditions and for a sufficient period of time to produce adipate, the adipate pathway comprising succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA synthetase or phosphotransadipylase/adipate kinase or adipyl-CoA:acetyl-CoA transferase or adipyl-CoA hydrolase. In another embodiment, the invention provides a method for producing adipate, comprising culturing a non-naturally occurring microbial organism having an adipate pathway, the pathway comprising at least one exogenous nucleic acid encoding an adipate pathway enzyme expressed in a sufficient amount to produce adipate, under conditions and for a sufficient period of time to produce adipate, the adipate pathway comprising succinyl-CoA:acetyl-CoA acyl transferase, 3-oxoadipyl-CoA transferase, 3-oxoadipate reductase, 3-hydroxyadipate dehydratase, and 2-enoate reductase.

In yet another embodiment, the invention provides a method for producing 6-aminocaproic acid, comprising culturing a non-naturally occurring microbial organism having a 6-aminocaproic acid pathway, the pathway comprising at least one exogenous nucleic acid encoding a 6-aminocaproic acid pathway enzyme expressed in a sufficient amount to produce 6-aminocaproic acid, under conditions and for a sufficient period of time to produce 6-aminocaproic acid, the 6-aminocaproic acid pathway comprising CoA-dependent aldehyde dehydrogenase and transaminase or 6-aminocaproate dehydrogenase. In a further embodiment, the invention provides a method for producing caprolactam, comprising culturing a non-naturally occurring microbial organism having a caprolactam pathway, the pathway comprising at least one exogenous nucleic acid encoding a caprolactam pathway enzyme expressed in a sufficient amount to produce caprolactam, under conditions and for a sufficient period of time to produce caprolactam, the caprolactam pathway comprising CoA-dependent aldehyde dehydrogenase, transaminase or 6-aminocaproate dehydrogenase, and amidohydrolase.

The invention additionally provides a method for producing adipate, comprising culturing a non-naturally occurring microbial organism having an adipate pathway, the pathway comprising at least one exogenous nucleic acid encoding an adipate pathway enzyme expressed in a sufficient amount to produce adipate, under conditions and for a sufficient period of time to produce adipate, the adipate pathway comprising alpha-ketoadipyl-CoA synthetase, phosphotransketoadipylase/alpha-ketoadipate kinase or alpha-ketoadipyl-CoA: acetyl-CoA transferase; 2-hydroxyadipyl-CoA dehydrogenase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase.

In still another embodiment, the invention provides a method for producing adipate, comprising culturing a non-naturally occurring microbial organism having an adipate pathway, the pathway comprising at least one exogenous nucleic acid encoding an adipate pathway enzyme expressed in a sufficient amount to produce adipate, under conditions and for a sufficient period of time to produce adipate, the adipate pathway comprising 2-hydroxyadipate dehydrogenase; 2-hydroxyadipyl-CoA synthetase, phosphotranshydroxyadipylase/2-hydroxyadipate kinase or 2-hydroxyadipyl-CoA:acetyl-CoA transferase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase.

Suitable purification and/or assays to test for the production of adipate, 6-aminocaproic acid or caprolactam can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme activities from the exogenous DNA sequences can also be assayed using methods well known in the art.

The adipate, 6-aminocaproic acid or caprolactam can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the adipate, 6-aminocaproic acid or caprolactam producers can be cultured for the biosynthetic production of adipate, 6-aminocaproic acid or caprolactam.

For the production of adipate, 6-aminocaproic acid or caprolactam, the recombinant strains are cultured in a medium with carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in U.S. patent application Ser. No. 11/891,602, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can be, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of adipate, 6-aminocaproic acid or caprolactam.

In addition to renewable feedstocks such as those exemplified above, the adipate, 6-aminocaproic acid or caprolactam microbial organisms of the invention also can be modified for growth on syngas as its source of carbon. In this specific embodiment, one or more proteins or enzymes are expressed in the adipate, 6-aminocaproic acid or caprolactam producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

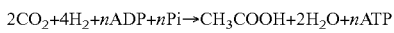

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes: cobalamide corrinoid/iron-sulfur protein, methyltransferase, carbon monoxide dehydrogenase, acetyl-CoA synthase, acetyl-CoA synthase disulfide reductase and hydrogenase. Following the teachings and guidance provided herein for introducing a sufficient number of encoding nucleic acids to generate an adipate, 6-aminocaproic acid or caprolactam pathway, those skilled in the art will understand that the same engineering design also can be performed with respect to introducing at least the nucleic acids encoding the Wood-Ljungdahl enzymes absent in the host organism. Therefore, introduction of one or more encoding nucleic acids into the microbial organisms of the invention such that the modified organism contains the complete Wood-Ljungdahl pathway will confer syngas utilization ability.

Given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, adipate, 6-aminocaproic acid or caprolactam and any of the intermediate metabolites in the adipate, 6-aminocaproic acid or caprolactam pathway. All that is required is to engineer in one or more of the required enzyme activities to achieve biosynthesis of the desired compound or intermediate including, for example, inclusion of some or all of the adipate, 6-aminocaproic acid or caprolactam biosynthetic pathways. Accordingly, the invention provides a non-naturally occurring microbial organism that produces and/or secretes adipate, 6-aminocaproic acid or caprolactam when grown on a carbohydrate and produces and/or secretes any of the intermediate metabolites shown in the adipate, 6-aminocaproic acid or caprolactam pathway when grown on a carbohydrate. For example, the adipate producing microbial organisms of the invention can initiate synthesis from an intermediate, for example, 3-oxoadipyl-CoA, 3-hydroxyadipyl-CoA, 5-carboxy-2-pentenoyl-CoA, or adipyl-CoA (see FIG. 2), as desired. In addition, an adipate producing microbial organism can initiate synthesis from an intermediate, for example, 3-oxoadipyl-CoA, 3-oxoadipate, 3-hydroxyadipate, or hexa-2-enedioate (see FIG. 3). The 6-aminocaproic acid producing microbial organism of the invention can initiate synthesis from an intermediate, for example, adipate semialdehyde (see FIG. 8). The caprolactam producing microbial organism of the invention can initiate synthesis from an intermediate, for example, adipate semialdehyde or 6-aminocaproic acid (see FIG. 8), as desired.

The non-naturally occurring microbial organisms of the invention are constructed using methods well known in the art as exemplified herein to exogenously express at least one nucleic acid encoding an adipate, 6-aminocaproic acid or caprolactam pathway enzyme in sufficient amounts to produce adipate, 6-aminocaproic acid or caprolactam. It is understood that the microbial organisms of the invention are cultured under conditions sufficient to produce adipate, 6-aminocaproic acid or caprolactam. Following the teachings and guidance provided herein, the non-naturally occurring microbial organisms of the invention can achieve biosynthesis of adipate, 6-aminocaproic acid or caprolactam resulting in intracellular concentrations between about 0.1-200 mM or more. Generally, the intracellular concentration of adipate, 6-aminocaproic acid or caprolactam is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. patent application Ser. No. 11/891,602, filed Aug. 10, 2007. Any of these conditions can be employed with the non-naturally occurring microbial organisms as well as other anaerobic conditions well known in the art. Under such anaerobic conditions, the adipate, 6-aminocaproic acid or caprolactam producers can synthesize adipate, 6-aminocaproic acid or caprolactam at intracellular concentrations of 5-10 mM or more as well as all other concentrations exemplified herein. It is understood that, even though the above description refers to intracellular concentrations, adipate, 6-aminocaproic acid or caprolactam producing microbial organisms can produce adipate, 6-aminocaproic acid or caprolactam intracellularly and/or secrete the product into the culture medium.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of adipate, 6-aminocaproic acid or caprolactam includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of adipate, 6-aminocaproic acid or caprolactam. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of adipate, 6-aminocaproic acid or caprolactam. Generally, and as with non-continuous culture procedures, the continuous and/or near-continuous production of adipate, 6-aminocaproic acid or caprolactam will include culturing a non-naturally occurring adipate, 6-aminocaproic acid or caprolactam producing organism of the invention in sufficient nutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of adipate, 6-aminocaproic acid or caprolactam can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the adipate, 6-aminocaproic acid or caprolactam producers of the invention for continuous production of substantial quantities of adipate, 6-aminocaproic acid or caprolactam, the adipate, 6-aminocaproic acid or caprolactam producers also can be, for example, simultaneously subjected to chemical synthesis procedures to convert the product to other compounds or the product can be separated from the fermentation culture and sequentially subjected to chemical conversion to convert the product to other compounds, if desired. As described herein, an intermediate in the adipate pathway utilizing 3-oxoadipate, hexa-2-enedioate, can be converted to adipate, for example, by chemical hydrogenation over a platinum catalyst (see Example III).

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of adipate, 6-aminocaproic acid or caprolactam.

One computational method for identifying and designing metabolic alterations favoring biosynthesis of a desired product is the OptKnock computational framework, Burgard et al., *Biotechnol. Bioeng.* 84:647-657 (2003). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. patent application Ser. No. 11/891,602, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

It is understood that modifications which do not substantially affect the activity of the various embodiments of this invention are also provided within the definition of the invention provided herein. Accordingly, the following examples are intended to illustrate but not limit the present invention.

Example I

Reverse Adipate Degradation Pathway

This example describes an exemplary adipate synthesis pathway via a reverse adipate degradation pathway.

Organisms such as *Penicillium chrysogenum* have the ability to naturally degrade adipate (Thykaer et al., *Metab. Eng.* 4:151-158. (2002)). The mechanism is similar to the oxidation of fatty acids (see FIG. 1). The first step in adipate degradation is an ATP-dependent reaction that activates adipate with CoA. The second reaction is catalyzed by a dehydrogenase that forms 5-carboxy-2-pentenoyl-CoA from adipyl-CoA. During peroxisomal adipate degradation, the dehydrogenase enzyme contains FAD, which accepts the electrons and then transfers them directly to oxygen. A catalase enzyme dissipates the $H_2O_2$ formed by the reduction of oxygen. In mitochondrial fatty acid oxidation, the FAD from the dehydrogenase transfers electrons directly to the electron transport chain. A multi-functional fatty acid oxidation protein in eukaryotes such as *S. cerevisiae* and *P. chrysogenum* carries out the following hydratase and dehydrogenase steps. The final step is an acyl transferase that splits 3-oxoadipyl CoA into acetyl-CoA and succinyl-CoA.

A highly efficient pathway for the production of adipate is achieved through genetically altering a microorganism such that similar enzymatic reactions are employed for adipate synthesis from succinyl-CoA and acetyl-CoA (see FIG. 2). Successful implementation of this entails expressing the appropriate genes, tailoring their expression, and altering culture conditions so that high acetyl-CoA, succinyl-CoA, and/or redox (for example, NADH/NAD+) ratios will drive the metabolic flux through this pathway in the direction of adipate synthesis rather than degradation. Strong parallels to butyrate formation in *Clostridia* (Kanehisa and Goto, *Nucl. Acids Res.* 28:27-30 (2000)) support that each step in the adipate synthesis pathway is thermodynamically feasible with reaction directionality governed by the concentrations of the participating metabolites. The final step, which forms adipate from adipyl-CoA, can take place either via a synthetase, phosphotransadipylase/kinase, transferase, or hydrolase mechanism.

The maximum theoretical yields of adipate using this pathway were calculated both in the presence and absence of an external electron acceptor such as oxygen. These calculations show that the pathway can efficiently transform glucose into adipate and $CO_2$ under anaerobic conditions with a 92% molar yield (Table I). The production of adipate using this pathway does not require the uptake of oxygen as NAD+ can be regenerated in the two hydrogenase steps that form 3-hydroxyadipyl-CoA and adipyl-CoA (see FIG. 2). Further, the pathway is favorable energetically as up to 1.55 moles of ATP are formed per mole of glucose consumed at the maximum theoretical yield of adipate assuming either a synthetase, phosphotransadipylase/kinase, or transferase mechanism for the final conversion step. The ATP yield can be further improved to 2.47 moles of ATP produced per mole of glucose if phosphoenolpyruvate carboxykinase (PPCK) is assumed to function in the ATP-generating direction towards oxaloacetate formation. Maximum ATP yield calculations were then performed assuming that the adipyl-CoA to adipate transformation is a hydrolysis step. This reduces the maximum ATP yields at maximum adipate production to 0.85 and 1.77 mole ATP per mole glucose consumed if PPCK is assumed irreversible and reversible, respectively. Nevertheless, these ATP yields are sufficient for cell growth, maintenance, and production.

TABLE 1

The maximum theoretical yields of adipate and the associated ATP yields per mole of glucose using the reverse degradation pathway assuming the final step in the pathway is a synthetase, phosphotransadipylase/kinase, or transferase.

|  | Aerobic | Anaerobic |
|---|---|---|
| Adipate Yield | 0.92 | 0.92 |
| Max ATP yield @ max adipate yield | 1.55 | 1.55 |
| Max ATP yield @ max adipate yield PPCK assumed | 2.47 | 2.47 |

Successfully engineering this pathway involves identifying an appropriate set of enzymes with sufficient activity and specificity. This entails identifying an appropriate set of enzymes, cloning their corresponding genes into a production host, optimizing fermentation conditions, and assaying for product formation following fermentation. To engineer a production host for the production of adipate, one or more exogenous DNA sequence(s) are expressed in a suitable host microorganism. In addition, the microorganisms can have endogenous gene(s) functionally deleted. These modifications allow the production of adipate using renewable feedstock.

Below is described a number of biochemically characterized candidate genes that encode enzymes that catalyze each step of the reverse adipate degradation pathway in a production host. Although described using E. coli as a host organism to engineer the pathway, essentially any suitable host organism can be used. Specifically listed are genes that are native to E. coli as well as genes in other organisms that can be applied to catalyze the appropriate transformations when properly cloned and expressed.

Referring to FIG. 2, step 1 involves succinyl CoA:acetyl CoA acyl transferase (β-ketothiolase). The first step in the pathway combines acetyl-CoA and succinyl-CoA to form 3-oxoadipyl-CoA. The gene products encoded by pcaF in Pseudomonas strain B13 (Kaschabek et al., J. Bacteriol. 184:207-215 (2002)), phaD in Pseudomonas putida U (Olivera et al., Proc. Natl. Acad. Sci. USA 95:6419-6424 (1998)), paaE in Pseudomonas fluorescens ST (Di Gennaro et al., Arch. Microbiol. 188:117-125 (2007)), and paaJ from E. coli (Nogales et al., Microbiol. 153:357-365 (2007)) catalyze the conversion of 3-oxoadipyl-CoA into succinyl-CoA and acetyl-CoA during the degradation of aromatic compounds such as phenylacetate or styrene. Since β-ketothiolase enzymes catalyze reversible transformations, these enzymes can be employed for the first step in adipate synthesis shown in FIG. 2. For example, the ketothiolase phaA from R. eutropha combines two molecules of acetyl-CoA to form acetoacetyl-CoA (Sato et al., J. Biosci. Bioengineer. 103:38-44 (2007)). Similarly, a β-keto thiolase (bktB) has been reported to catalyze the condensation of acetyl-CoA and propionyl-CoA to form β-ketovaleryl-CoA (Slater et al., J. Bacteriol. 180: 1979-1987 (1998)) in R. eutropha. The protein sequences for the above-mentioned gene products are well known in the art and can be accessed in the public databases such as GenBank using the following accession numbers.

| Gene name | GenBank Accession # | Organism |
|---|---|---|
| paaJ | NP_415915.1 | Escherichia coli |
| pcaF | AAL02407 | Pseudomonas knackmussii (B13) |
| phaD | AAC24332.1 | Pseudomonas putida |
| paaE | ABF82237.1 | Pseudomonas fluorescens |

These exemplary sequences can be used to identify homologue proteins in GenBank or other databases through sequence similarity searches (for example, BLASTp). The resulting homologue proteins and their corresponding gene sequences provide additional exogenous DNA sequences for transformation into E. coli or other suitable host microorganisms to generate production hosts.

For example, orthologs of paaJ from Escherichia coli K12 can be found using the following GenBank accession numbers:

| YP_001335140.1 | Klebsiella pneumoniae |
|---|---|
| YP_001479310.1 | Serratia proteamaculans |
| AAC24332.1 | Pseudomonas putida |

Example orthologs of pcaF from Pseudomonas knackmussii can be found using the following GenBank accession numbers:

| AAD22035.1 | Streptomyces sp. 2065 |
|---|---|
| AAN67000.1 | Pseudomonas putida |
| ABJ15177.1 | Pseudomonas aeruginosa |

Additional native candidate genes for the ketothiolase step include atoB, which can catalyze the reversible condensation of 2 acetyl-CoA molecules (Sato et al., J. Biosci. Bioengineer. 103:38-44 (2007)), and its homolog yqeF. Non-native gene candidates include phaA (Sato et al., supra, 2007) and bktB (Slater et al., J. Bacteriol. 180:1979-1987 (1998)) from R. eutropha, and the two ketothiolases, thiA and thiB, from Clostridium acetobutylicum (Winzer et al., J. Mol. Microbiol. Biotechnol. 2:531-541 (2000)). The protein sequences for each of these exemplary gene products can be found using the following GenBank accession numbers:

| atoB | NP_416728.1 | Escherichia coli |
|---|---|---|
| yqeF | NP_417321.2 | Escherichia coli |
| phaA | YP_725902 | Ralstonia eutropha |
| bktB | AAC38322.1 | Ralstonia eutropha |
| thiA | NP_349476.1 | Clostridium acetobutylicum |
| thiB | NP_149242.1 | Clostridium acetobutylicum |

Referring to FIG. 2, step 2 involves 3-hydroxyacyl-CoA dehydrogenase. The second step in the pathway involves the reduction of 3-oxoadipyl-CoA to 3-hydroxyadipyl-CoA. The gene products encoded by phaC in Pseudomonas putida U (Olivera et al., Proc. Natl. Acad. Sci. USA 95:6419-6424 (1998)) and paaC in Pseudomonas fluorescens ST (Di Gennaro et al., Arch. Microbiol. 188:117-125 (2007)) catalyze the reverse reaction, that is, the oxidation of 3-hydroxyadipyl-CoA to form 3-oxoadipyl-CoA, during the catabolism of phenylacetate or styrene. The reactions catalyzed by such dehydrogenases are reversible and accordingly these genes represent candidates to carry out the second step of adipate synthesis as shown in FIG. 2. A similar transformation is also carried out by the gene product of hbd in Clostridium acetobutylicum (Atsumi et al., Metab.

Eng. (epub Sep. 14, 2007); Boynton et al., *J. Bacteriol.* 178:3015-3024 (1996)). This enzyme converts acetoacetyl-CoA to 3-hydroxybutyryl-CoA. Lastly, given the proximity in *E. coli* of paaH to other genes in the phenylacetate degradation operon (Nogales et al., *Microbiol.* 153:357-365 (2007)) and the fact that paaH mutants cannot grow on phenylacetate (Ismail et al., *Eur. J. Biochem.* 270:3047-3054 (2003)), it is expected that the *E. coli* paaH gene encodes a 3-hydroxyacyl-CoA dehydrogenase. The protein sequences for each of these exemplary gene products can be found using the following GenBank accession numbers:

| paaH | NP_415913.1 | *Escherichia coli* |
| phaC | NP_745425.1 | *Pseudomonas putida* |
| paaC | ABF82235.1 | *Pseudomonas fluorescens* |
| hbd | NP_349314.1 | *Clostridium acetobutylicum* |

Referring to FIG. 2, step 3 involves 3-hydroxyadipyl-CoA dehydratase. The gene product of crt from *C. acetobutylicum* catalyzes the dehydration of 3-hydroxybutyryl-CoA to crotonyl-CoA (see FIG. 2) (Atsumi et al., supra, 2007; Boynton et al., *J. Bacteriol.* 178:3015-3024 (1996)). Homologs of this gene are strong candidates for carrying out the third step in the adipate synthesis pathway exemplified in FIG. 2. In addition, genes known to catalyze the hydroxylation of double bonds in enoyl-CoA compounds represent additional candidates given the reversibility of such enzymatic transformations. For example, the enoyl-CoA hydratases, phaA and phaB, of *P. putida* are believed to carry out the hydroxylation of double bonds during phenylacetate catabolism (Olivera et al., *Proc. Natl. Acad. Sci. USA* 95:6419-6424 (1998)) and thus represent additional candidates for incorporation into *E. coli*. The deletion of these genes precludes phenylacetate degradation in *P. putida*. The paaA and paaB from *P. fluorescens* catalyze analogous transformations (Olivera et al., supra, 1998). Lastly, a number of *Escherichia coli* genes have been shown to demonstrate enoyl-CoA hydratase functionality including maoC (Park and Lee, *J. Bacteriol.* 185:5391-5397 (2003)), paaF (Ismail et al., *Eur. J. Biochem.* 270:3047-3054 (2003); Park and Lee, *Biotechnol. Bioeng.* 86:681-686 (2004); Park and Lee, *Appl. Biochem. Biotechnol.* 113-116:335-346 (2004)), and paaG (Ismail et al., supra, 2003; Park and Lee, supra, 2004; Park and Lee, supra, 2004). The protein sequences for each of these exemplary gene products can be found using the following GenBank accession numbers:

| maoC | NP_415905.1 | *Escherichia coli* |
| paaF | NP_415911.1 | *Escherichia coli* |
| paaG | NP_415912.1 | *Escherichia coli* |
| crt | NP_349318.1 | *Clostridium acetobutylicum* |
| paaA | NP_745427.1 | *Pseudomonas putida* |
| paaB | NP_745426.1 | *Pseudomonas putida* |
| phaA | ABF82233.1 | *Pseudomonas fluorescens* |
| phaB | ABF82234.1 | *Pseudomonas fluorescens* |

Alternatively, β-oxidation genes are candidates for the first three steps in adipate synthesis. Candidate genes for the proposed adipate synthesis pathway also include the native fatty acid oxidation genes of *E. coli* and their homologs in other organisms. The *E. coli* genes fadA and fadB encode a multienzyme complex that exhibits ketoacyl-CoA thiolase, 3-hydroxyacyl-CoA dehydrogenase, and enoyl-CoA hydratase activities (Yang et al., *Biochem.* 30:6788-6795 (1991); Yang et al., *Biol. Chem.* 265:10424-10429 (1990); Yang et al., *Biol. Chem.* 266:16255 (1991); Nakahigashi and Inokuchi, *Nucl. Acids Res.* 18: 4937 (1990)). These activities are mechanistically similar to the first three transformations shown in FIG. 2. The fadI and fadJ genes encode similar functions and are naturally expressed only anaerobically (Campbell et al., *Mol. Microbiol.* 47:793-805 (2003)). These gene products naturally operate to degrade short, medium, and long chain fatty-acyl-CoA compounds to acetyl-CoA, rather than to convert succinyl-CoA and acetyl-CoA into 5-carboxy-2-pentenoyl-CoA as proposed in FIG. 2. However, it is well known that the ketoacyl-CoA thiolase, 3-hydroxyacyl-CoA dehydrogenase, and enoyl-CoA hydratase enzymes catalyze reversible transformations. Furthermore, directed evolution and related approaches can be applied to tailor the substrate specificities of the native β-oxidation machinery of *E. coli*. Thus these enzymes or homologues thereof can be applied for adipate production. If the native genes operate to degrade adipate or its precursors in vivo, the appropriate genetic modifications are made to attenuate or eliminate these functions. However, it may not be necessary since a method for producing poly[(R)-3-hydroxybutyrate] in *E. coli* that involves activating fadB, by knocking out a negative regulator, fadR, and co-expressing a non-native ketothiolase, phaA from *Ralstonia eutropha*, has been described (Sato et al., *J. Biosci. Bioeng.* 103:38-44 (2007)). This work clearly demonstrated that a β-oxidation enzyme, in particular the gene product of fadB which encodes both 3-hydroxyacyl-CoA dehydrogenase and enoyl-CoA hydratase activities, can function as part of a pathway to produce longer chain molecules from acetyl-CoA precursors. The protein sequences for each of these exemplary gene products can be found using the following GenBank accession numbers:

| fadA | YP_026272.1 | *Escherichia coli* |
| fadB | NP_418288.1 | *Escherichia coli* |
| fadI | NP_416844.1 | *Escherichia coli* |
| fadJ | NP_416843.1 | *Escherichia coli* |
| fadR | NP_415705.1 | *Escherichia coli* |

Referring to FIG. 2, step 4 involves 5-carboxy-2-pentenoyl-CoA reductase. Whereas the ketothiolase, dehydrogenase, and enoyl-CoA hydratase steps are generally reversible, the enoyl-CoA reductase step is almost always oxidative and irreversible under physiological conditions (Hoffmeister et al., *J. Biol. Chem.* 280:4329-4338 (2005)). FadE catalyzes this likely irreversible transformation in *E. coli* (Campbell and Cronan, *J. Bacteriol.* 184:3759-3764 (2002)). The pathway requires an enzyme that can reduce a 2-enoyl-CoA intermediate, not one such as FadE that will only oxidize an acyl-CoA to a 2-enoyl-CoA compound. Furthermore, although it has been suggested that *E. coli* naturally possesses enzymes for enoyl-CoA reduction (Mizugaki et al., *J. Biochem.* 92:1649-1654 (1982); Nishimaki et al., *J. Biochem.* 95:1315-1321 (1984)), no *E. coli* gene possessing this function has been biochemically characterized.

One candidate gene for the enoyl-CoA reductase step is the gene product of bcd from *C. acetobutylicum* (Atsumi et al., supra, 2007; Boynton et al., *J. Bacteriol.* 178:3015-3024 (1996)), which naturally catalyzes the reduction of crotonyl-CoA to butyryl-CoA, a reaction similar in mechanism to the desired reduction of 5-carboxy-2-pentenoyl-CoA to adipyl-CoA in the adipate synthesis pathway. Activity of this enzyme can be enhanced by expressing bcd in conjunction with expression of the *C. acetobutylicum* etfAB genes, which encode an electron transfer flavoprotein. An additional candidate for the enoyl-CoA reductase step is the mitochondrial enoyl-CoA reductase from *E. gracilis* (Hoffmeister et al., *J. Biol. Chem.* 280:4329-4338 (2005)). A construct derived from this sequence following the removal of its mitochondrial targeting leader sequence was cloned in *E. coli*, resulting in an active enzyme (Hoffmeister et al., supra, 2005). This approach is well known to those skilled in the art of expressing eukaryotic genes, particularly those with leader sequences that may target the gene product to a specific intracellular compartment, in prokaryotic organisms. A close homolog of this gene, TDE0597, from the prokaryote *Treponema denticola* represents a third enoyl-CoA reductase which has been cloned and expressed in *E. coli* (Tucci and Martin, *FEBS Lett.* 581:1561-1566 (2007)). The protein sequences for each of these exemplary gene products can be found using the following GenBank accession numbers:

| bcd | NP_349317.1 | *Clostridium acetobutylicum* |
|---|---|---|
| etfA | NP_349315.1 | *Clostridium acetobutylicum* |
| etfB | NP_349316.1 | *Clostridium acetobutylicum* |
| TER | Q5EU90.1 | *Euglena gracilis* |
| TDE0597 | NP_971211.1 | *Treponema denticola* |

Referring to FIG. 2, step 5 involves adipyl-CoA synthetase (also referred to as adipate-CoA ligase), phosphotransadipylase/adipate kinase, adipyl-CoA:acetyl-CoA transferase, or adipyl-CoA hydrolase. From an energetic standpoint, it is desirable for the final step in the adipate synthesis pathway to be catalyzed by an enzyme or enzyme pair that can conserve the ATP equivalent stored in the thioester bond of adipyl-CoA. The product of the sucC and sucD genes of *E. coli*, or homologs thereof, can potentially catalyze the final transformation shown in FIG. 2 should they exhibit activity on adipyl-CoA. The sucCD genes naturally form a succinyl-CoA synthetase complex that catalyzes the formation of succinyl-CoA from succinate with the concomitant consumption of one ATP, a reaction which is reversible in vivo (Buck et al., *Biochem.* 24:6245-6252 (1985)). Given the structural similarity between succinate and adipate, that is, both are straight chain dicarboxylic acids, it is reasonable to expect some activity of the sucCD enzyme on adipyl-CoA. An enzyme exhibiting adipyl-CoA ligase activity can equivalently carry out the ATP-generating production of adipate from adipyl-CoA, here using AMP and PPi as cofactors, when operating in the opposite physiological direction as depicted in FIG. 1. Exemplary CoA-ligases include the rat dicarboxylate-CoA ligase for which the sequence is yet uncharacterized (Vamecq et al., *Biochem. J.* 230:683-693 (1985)), either of the two characterized phenylacetate-CoA ligases from *P. chrysogenum* (Lamas-Maceiras et al., *Biochem. J.* 395, 147-155 (2005); Wang et al., *Biochem. Biophy. Res. Commun.* 360:453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacillus subtilis* (Bower et al., *J. Bacteriol.* 178:4122-4130 (1996)). The protein sequences for each of these exemplary gene products can be found using the following GenBank accession numbers:

| sucC | NP_415256.1 | *Escherichia coli* |
|---|---|---|
| sucD | AAC73823.1 | *Escherichia coli* |

Another option, using phosphotransadipylase/adipate kinase, is catalyzed by the gene products of buk1, buk2, and ptb from *C. acetobutylicum* (Walter et al., *Gene* 134:107-111 (1993); Huang et al., *J. Mol. Microbiol. Biotechnol.* 2:33-38 (2000)), or homologs thereof. The ptb gene encodes an enzyme that can convert butyryl-CoA into butyryl-phosphate, which is then converted to butyrate via either of the buk gene products with the concomitant generation of ATP. The analogous set of transformations, that is, conversion of adipyl-CoA to adipyl-phosphate followed by conversion of adipyl-phosphate to adipate, can be carried out by the buk1, buk2, and ptb gene products. The protein sequences for each of these exemplary gene products can be found using the following GenBank accession numbers:

| ptb | NP_349676 | *Clostridium acetobutylicum* |
|---|---|---|
| buk1 | NP_349675 | *Clostridium acetobutylicum* |
| buk2 | Q97II1 | *Clostridium acetobutylicum* |

Alternatively, an acetyltransferase capable of transferring the CoA group from adipyl-CoA to acetate can be applied. Similar transformations are catalyzed by the gene products of cat1, cat2, and cat3 of *Clostridium kluyveri* which have been shown to exhibit succinyl-CoA, 4-hydroxybutyryl-CoA, and butyryl-CoA acetyltransferase activity, respectively (Sohling and Gottschalk, *J. Bacteriol.* 178:871-880 (1996); Seedorf et al., *Proc. Natl. Acad. Sci. USA* 105:2128-2133 (2008)). The protein sequences for each of these exemplary gene products can be found using the following GenBank accession numbers:

| cat1 | P38946.1 | *Clostridium kluyveri* |
|---|---|---|
| cat2 | P38942.2 | *Clostridium kluyveri* |
| cat3 | EDK35586.1 | *Clostridium kluyveri* |

Finally, though not as desirable from an energetic standpoint, the conversion of adipyl-CoA to adipate can also be carried out by an acyl-CoA hydrolase or equivalently a thioesterase. The top *E. coli* gene candidate is tesB (Naggert et al., *J. Biol. Chem.* 266:11044-11050 (1991)), which shows high similarity to the human acot8, which is a dicarboxylic acid acetyltransferase with activity on adipyl-CoA (Westin et al., *J. Biol. Chem.* 280:38125-38132 (2005)). This activity has also been characterized in the rat liver (Deana, *Biochem. Int.* 26:767-773 (1992)). The protein sequences for each of these exemplary gene products can be found using the following GenBank accession numbers:

| tesB | NP_414986 | *Escherichia coli* |
|---|---|---|
| acot8 | CAA15502 | *Homo sapiens* |
| acot8 | NP_570112 | *Rattus norvegicus* |

Other native candidate genes include tesA (Bonner and Bloch, *J. Biol. Chem.* 247:3123-3133 (1972)), ybgC (Kuznetsova et al., *FEMS Microbiol. Rev.* 29:263-279 (2005); Zhuang et al., *FEBS Lett.* 516:161-163 (2002)), paaI (Song et al., *J. Biol. Chem.* 281:11028-11038 (2006)), and ybdB (Leduc et al., *J. Bacteriol.* 189:7112-7126 (2007)). The protein sequences for each of these exemplary gene products can be found using the following GenBank accession numbers:

| tesA | NP_415027 | *Escherichia coli* |
| ybgC | NP_415264 | *Escherichia coli* |
| paaI | NP_415914 | *Escherichia coli* |
| ybdB | NP_415129 | *Escherichia coli* |

The above description provides an exemplary adipate synthesis pathway by way of a reverse adipate degradation pathway.

Example II

Preparation of an Adipate Producing Microbial Organism Having a Reverse Degradation Pathway This example describes the generation of a microbial organism capable of producing adipate using the reverse degradation pathway.

*Escherichia coli* is used as a target organism to engineer a reverse adipate degradation pathway as shown in FIG. 2. *E. coli* provides a good host for generating a non-naturally occurring microorganism capable of producing adipate. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce adipate, nucleic acids encoding the enzymes utilized in the reverse degradation pathway are expressed in *E. coli* using well known molecular biology techniques (see, for example, Sambrook, supra, 2001; Ausubel supra, 1999). In particular, the paaJ (NP_415915.1), paaH (NP_415913.1), and maoC (NP_415905.1) genes encoding the succinyl-CoA:acetyl-CoA acyl transferase, 3-hydroxyacyl-CoA dehydrogenase, and 3-hydroxyadipyl-CoA dehydratase activities, respectively, are cloned into the pZE13 vector (Expressys, Ruelzheim, Germany) under the PA1/lacO promoter. In addition, the bcd (NP_349317.1), etfAB (349315.1 and 349316.1), and sucCD (NP_415256.1 and AAC73823.1) genes encoding 5-carboxy-2-pentenoyl-CoA reductase and adipyl-CoA synthetase activities, respectively, are cloned into the pZA33 vector (Expressys, Ruelzheim, Germany) under the PA1/lacO promoter. The two sets of plasmids are transformed into *E. coli* strain MG1655 to express the proteins and enzymes required for adipate synthesis via the reverse degradation pathway.

The resulting genetically engineered organism is cultured in glucose-containing medium following procedures well known in the art (see, for example, Sambrook et al., supra, 2001). The expression of reverse degradation pathway genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce adipate is confirmed using HPLC, gas chromatography-mass spectrometry (GCMS) and/or liquid chromatography-mass spectrometry (LCMS).

Microbial strains engineered to have a functional adipate synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of adipate. One modeling method is the bilevel optimization approach, OptKnock (Burgard et al., *Biotechnol. Bioengineer.* 84:647-657 (2003)), which is applied to select gene knockouts that collectively result in better production of adipate. Adaptive evolution also can be used to generate better producers of, for example, the acetyl-CoA and succinyl-CoA intermediates or the adipate product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the adipate producer to further increase production.

For large-scale production of adipate, the above reverse degradation pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

This example describes the preparation of an adipate producing microbial organism using a reverse degradation pathway.

Example III

Adipate Synthesis Through 3-Oxoadipate

This example describes an exemplary adipate synthesis pathway through 3-oxoadipate.

Figure 3:
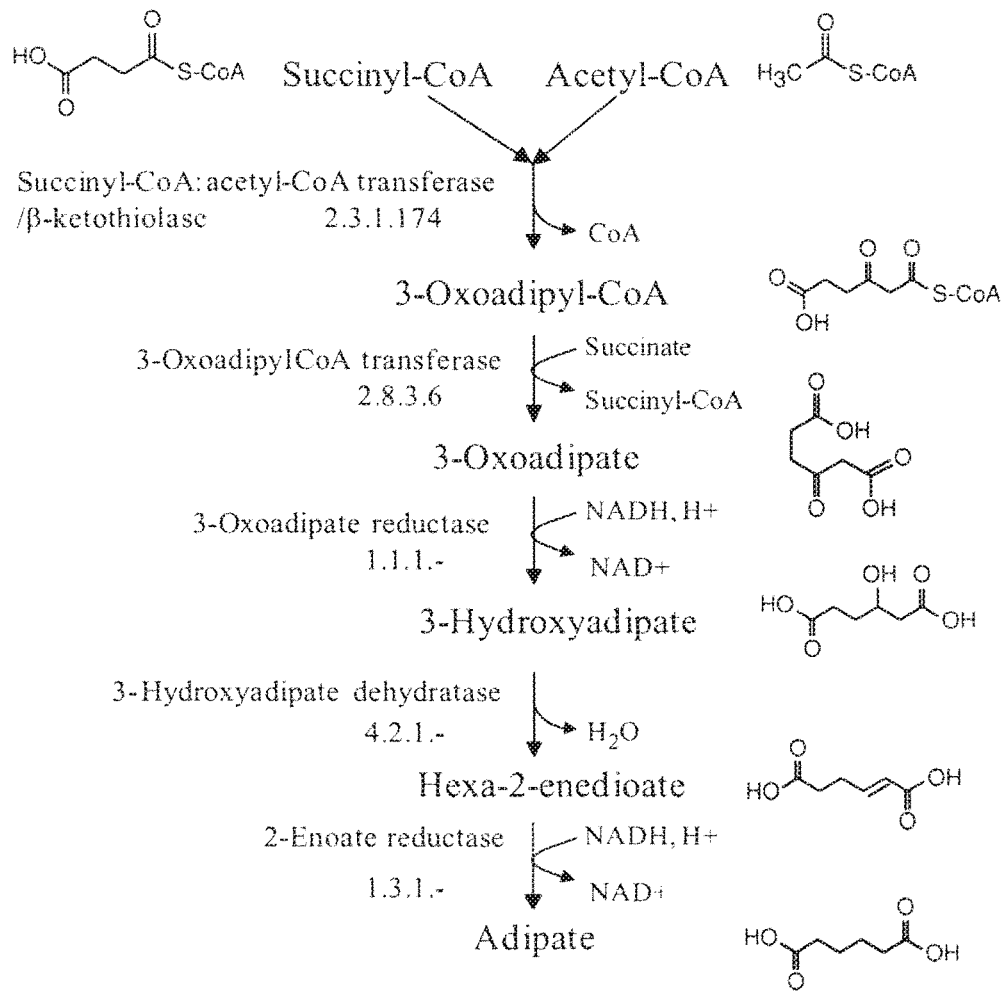
FIG. 3 shows an exemplary pathway for adipate formation via the 3-oxoadipate pathway.

An additional pathway from that described in Examples I and II that uses acetyl-CoA and succinyl-CoA as precursors for adipate formation and passes through the metabolic intermediate, 3-oxoadipate, is shown in FIG. 3. The initial two transformations in this pathway are the two terminal steps of the degradation pathway for aromatic and choloro-aromatic compounds operating in the reverse direction (Kaschabek et al., *J. Bacteriol.* 184:207-215 (2002); Nogales et al., *Microbiol.* 153:357-365 (2007); Ismail et al., *Eur. J. Biochem.* 270:3047-3054 (2003)). Specifically, the first step forms 3-oxoadipyl CoA by the condensation of succinyl- and acetyl-CoA. The second step forms 3-oxoadipate and is reported to be reversible in *Pseudomonas* sp. Strain B13 (Kaschabek et al., *J. Bacteriol.* 184:207-215 (2002)).

Figure 4:
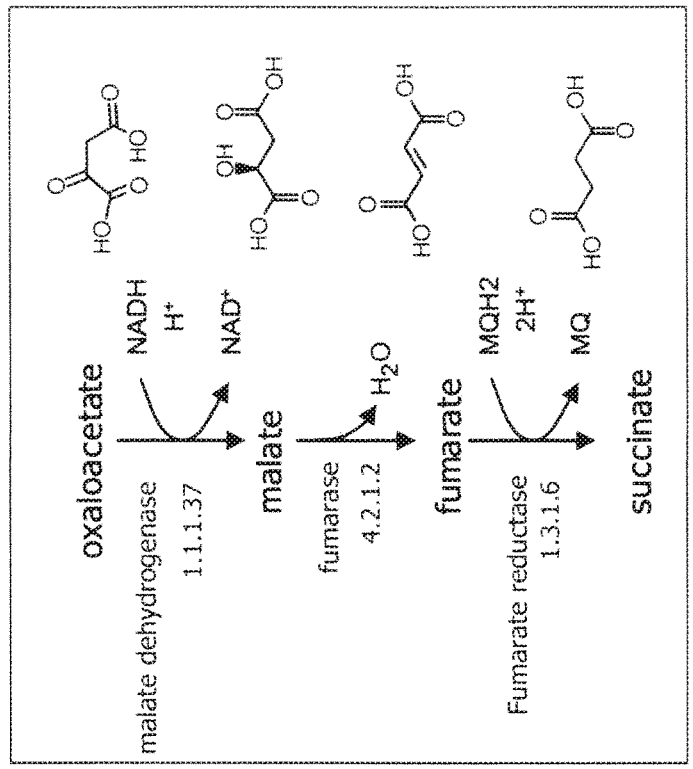
FIG. 4 show the similar enzyme chemistries of the last three steps of the 3-oxoadipate pathway for adipate synthesis and the reductive TCA cycle.
Figure 4:
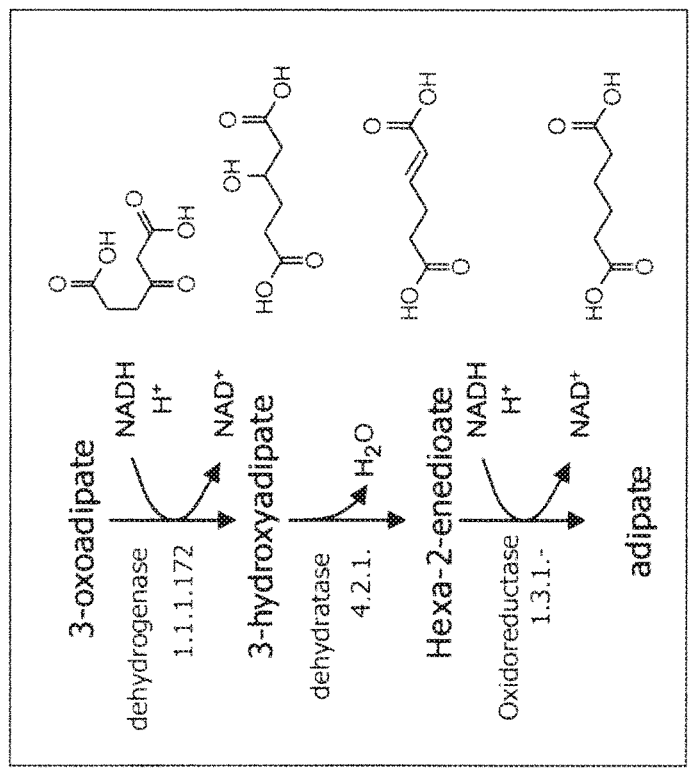

The subsequent steps involve reduction of 3-oxoadipate to 3-hydroxyadipate (conversion of a keto group to hydroxyl group), dehydration of 3-hydroxyadipate to yield hexa-2-enedioate, and reduction of hexa-2-enedioate to form adipate. These steps of the pathway are analogous to the conversion of oxaloacetate into succinate via the reductive TCA cycle (see FIG. 4). This supports the steps in the pathway being thermodynamically favorable subject to the presence of appropriate metabolite concentrations. The final reduction step can be carried out either biochemically or by employing a chemical catalyst to convert hexa-2-enedioate into adipate. Chemical hydrogenation can be performed using Pt catalyst on activated carbon as has been described in (Niu et al., *Biotechnol. Prog.* 18:201-211 (2002)).

The maximum theoretical yield of adipate using this pathway is 0.92 mole per mole glucose consumed, and oxygen is not required for attaining these yields (see Table 2). The associated energetics are identical to those of the reverse adipate pathway. Theoretically, ATP formation of up to 1.55 moles is observed per mole of glucose utilized through this pathway. The ATP yield improves to approximately 2.47 moles if phosphoenolpyruvate kinase (PPCK) is assumed to operate in the direction of ATP generation. Interestingly, the product yield can be increased further to 1 mole adipate per mole of glucose consumed if chemical hydrogenation is used for the last step and a 100% efficiency of catalysis is assumed. In this scenario, up to 1.95 moles of ATP are formed theoretically without assuming the reverse functionality of PPCK.

TABLE 2

The maximum theoretical yields of adipate and the associated ATP yields per mole of glucose using the 3-oxoadipate pathway.

|  | Final step enzymatic | | Final step chemical hydrogenation | |
|---|---|---|---|---|
|  | Aerobic | Anaerobic | Aerobic | Anaerobic |
| Adipate Yield | 0.92 | 0.92 | 1.00 | 1.00 |
| Max ATP yield @ max adipate yield | 1.55 | 1.55 | 1.95 | 1.95 |

Successfully engineering this pathway involves identifying an appropriate set of enzymes with sufficient activity and specificity. This entails identifying an appropriate set of enzymes, cloning their corresponding genes into a production host, optimizing fermentation conditions, and assaying for product formation following fermentation. To engineer a production host for the production of adipate, one or more exogenous DNA sequence(s) can be expressed in a host microorganism. In addition, the host microorganism can have endogenous gene(s) functionally deleted. These modifications allow the production of adipate using renewable feedstock.

Described below are a number of biochemically characterized candidate genes capable of encoding enzymes that catalyze each step of the 3-oxoadipate pathway for adipate synthesis. Although this method is described for *E. coli*, one skilled in the art can apply these teachings to any other suitable host organism. Specifically, listed below are genes that are native to *E. coli* as well as genes in other organisms that can be applied to catalyze the appropriate transformations when properly cloned and expressed.

Referring to FIG. 3, step 1 involves succinyl CoA:acetyl CoA acyl transferase (β-ketothiolase). The first step in the pathway combines acetyl-CoA and succinyl-CoA to form 3-oxoadipyl-CoA. The gene products encoded by pcaF in *Pseudomonas* strain B13 (Kaschabek et al., *J. Bacteriol.* 184:207-215 (2002)), phaD in *Pseudomonas putida* U (Olivera et al., *Proc. Natl. Acad. Sci. USA* 95:6419-6424 (1998)), paaE in *Pseudomonas fluorescens* ST (Di Gennaro et al., *Arch. Microbiol.* 188:117-125 (2007)), and paaJ from *E. coli* (Nogales et al., *Microbiol.* 153:357-365 (2007)) catalyze the conversion of 3-oxoadipyl-CoA into succinyl-CoA and acetyl-CoA during the degradation of aromatic compounds such as phenylacetate or styrene. Since β-ketothiolase enzymes catalyze reversible transformations, these enzymes can be employed for the first step in adipate synthesis shown in FIG. 3. For example, the ketothiolase phaA from *R. eutropha* combines two molecules of acetyl-CoA to form acetoacetyl-CoA (Sato et al., *J. Biosci. Bioengineer.* 103:38-44 (2007)). Similarly, a β-keto thiolase (bktB) has been reported to catalyze the condensation of acetyl-CoA and propionyl-CoA to form β-ketovaleryl-CoA (Slater et al., *J. Bacteriol.* 180:1979-1987 (1998)) in *R. eutropha*. The protein sequences for the above-mentioned gene products are well known in the art and can be accessed in the public databases such as GenBank using the following accession numbers.

| Gene name | GenBank Accession # | Organism |
|---|---|---|
| paaJ | NP_415915.1 | *Escherichia coli* |
| pcaF | AAL02407 | *Pseudomonas knackmussii* (B13) |
| phaD | AAC24332.1 | *Pseudomonas putida* |
| paaE | ABF82237.1 | *Pseudomonas fluorescens* |

These sequences can be used to identify homologue proteins in GenBank or other databases through sequence similarity searches, for example, BLASTp. The resulting homologue proteins and their corresponding gene sequences provide additional exogenous DNA sequences for transformation into *E. coli* or other microorganisms to generate production hosts.

For example, orthologs of paaJ from *Escherichia coli* K12 can be found using the following GenBank accession numbers:

| YP_001335140.1 | *Klebsiella pneumoniae* |
|---|---|
| YP_001479310.1 | *Serratia proteamaculans* |
| AAC24332.1 | *Pseudomonas putida* |

Example orthologs of pcaF from *Pseudomonas knackmussii* can be found using the following GenBank accession numbers:

| AAD22035.1 | *Streptomyces* sp. 2065 |
|---|---|
| AAN67000.1 | *Pseudomonas putida* |
| ABJ15177.1 | *Pseudomonas aeruginosa* |

Additional native candidate genes for the ketothiolase step include atoB which can catalyze the reversible condensation of 2 acetyl-CoA molecules (Sato et al., *J. Biosci. Bioengineer.* 103:38-44 (2007)), and its homolog yqeF. Non-native gene candidates include phaA (Sato et al., supra, 2007) and bktB (Slater et al., *J. Bacteriol.* 180:1979-1987 (1998)) from *R. eutropha*, and the two ketothiolases, thiA and thiB, from *Clostridium acetobutylicum* (Winzer et al., *J.*

Mol. Microbiol. Biotechnol. 2:531-541 (2000)). The protein sequences for each of these exemplary gene products can be found using the following GenBank accession numbers:

| atoB | NP_416728.1 | Escherichia coli |
| --- | --- | --- |
| yqeF | NP_417321.2 | Escherichia coli |
| phaA | YP_725941 | Ralstonia eutropha |
| bktB | AAC38322.1 | Ralstonia eutropha |
| thiA | NP_349476.1 | Clostridium acetobutylicum |
| thiB | NP_149242.1 | Clostridium acetobutylicum |

It is less desirable to use the thiolase-encoding genes fadA and fadB, genes in fatty acid degradation pathway in *E. coli*, in this exemplary pathway. These genes form a complex that encodes for multiple activities, most of which are not desired in this pathway.

Referring to FIG. 3, step 2 involves 3-oxoadipyl-CoA transferase. In this step, 3-oxoadipate is formed by the transfer of the CoA group from 3-oxoadipyl-CoA to succinate. This activity is reported in a two-unit enzyme encoded by pcaI and pcaJ in *Pseudomonas* (Kaschabek et al., *J. Bacteriol.* 184:207-215 (2002)). This enzyme catalyzes a reversible transformation. The protein sequences of exemplary gene products for subunit A of this complex can be found using the following GenBank accession numbers:

| pcaI | AAN69545.1 | Pseudomonas putida |
| --- | --- | --- |
| pcaI | YP_046368.1 | Acinetobacter sp. ADP1 |
| pcaI | NP_630776.1 | Streptomyces coelicolor |

The protein sequences of exemplary gene products for subunit B of this complex can be found using the following GenBank accession numbers:

| pcaJ | NP_746082.1 | Pseudomonas putida |
| --- | --- | --- |
| pcaJ | NP_630775.1 | Streptomyces coelicolor |
| pcaJ | AAC37147.1 | Acinetobacter sp. ADP1 |

Referring to FIG. 3, step 3 involves 3-oxoadipate reductase. *E. coli* has several candidate alcohol dehydrogenases; two that have analogous functions are malate dehydrogenase (mdh) and lactate dehydrogenase (ldhA). While it has not been shown that these two enzymes have broad substrate specificities in *E. coli*, lactate dehydrogenase from *Ralstonia eutropha* has been shown to demonstrate high activities on substrates of various chain lengths such as lactate, 2-oxobutyrate, 2-oxopentanoate and 2-oxoglutarate (Steinbuchel and Schlegel, *Eur. J. Biochem.* 130:329-334 (1983)). An additional non-native enzyme candidate for this step is the mitochondrial 3-hydroxybutyrate dehydrogenase (bdh) from the human heart which has been cloned and characterized (Marks et al., *J. Biol. Chem.* 267:15459-15463 (1992)). This enzyme is particularly interesting in that it is a dehydrogenase that operates on a 3-hydroxyacid. Given that dehydrogenases are typically reversible, it is expected that this gene product, or a homlog thereof, will be capable of reducing a 3-oxoacid, for example, 3-oxoadipate, to the corresponding 3-hydroxyacid, for example, 3-hydroxyadipate. The protein sequences for each of these exemplary gene products can be found using the following GenBank accession numbers:

| mdh | AAC76268.1 | Escherichia coli |
| --- | --- | --- |
| ldhA | NP_415898.1 | Escherichia coli |
| ldh | YP_725182.1 | Ralstonia eutropha |
| bdh | AAA58352.1 | Homo sapiens |

Referring to FIG. 3, step 4 involves 3-hydroxyadipate dehydratase. In this reaction, 3-hydroxyadipate is dehydrated to hexa-2-enedioate. Although no direct evidence for this enzymatic transformation has been identified, most dehydratases catalyze the α,β-elimination of water. This involves activation of the α-hydrogen by an electron-withdrawing carbonyl, carboxylate, or CoA-thiol ester group and removal of the hydroxyl group from the β-position (Martins et al., *Proc. Natl. Acad. Sci. USA* 101:15645-15649 (2004); Buckel and Golding, *FEMS Microbiol. Rev.* 22:523-541 (1998)). The protein sequences for exemplary gene products can be found using the following GenBank accession numbers:

| acnA | P25516.3 | Escherichia coli |
| --- | --- | --- |
| fumB | P14407.2 | Escherichia coli |
| ilvD | AAA24013.1 | Escherichia coli |

Other good candidates for carrying out this function are the serine dehydratases. These enzymes catalyze a very similar transformation in the removal of ammonia from serine as required in this dehydration step. The protein sequence for exemplary gene product can be found using the following GenBank accession number:

| dsdA | P00926 | Escherichia coli |
| --- | --- | --- |

Non-native gene candidates for this transformation have been identified as well. For example, the multi-subunit L-serine dehydratase from *Peptostreptococcus asaccharolyticus* was shown to complement an *E. coli* strain deficient in L-serine dehydratase activity (Hofmeister et al., *J. Bacteriol.* 179:4937-4941 (1997)). Further, a putative 2-(hydroxymethyl)glutarate dehydratase, encoded by the gene hmd in *Eubacterium barkeri* shows similarity to both α- and β-subunits of [4Fe-4S]-containing bacterial serine dehydratases (Alhapel et al., *Proc. Natl. Acad. Sci. USA* 103: 12341-12346 (2006)). The protein sequence for exemplary gene product can be found using the following GenBank accession number:

| hmd | ABC88407.1 | Eubacterium barkeri |
| --- | --- | --- |

Referring to FIG. 3, step 5 involves 2-enoate reductase. The final step in the 3-oxoadipate pathway is reduction of the double bond in hexa-3-enedioate to form adipate. Biochemically, this transformation can be catalyzed by 2-enoate reductase (EC 1.3.1.31) known to catalyze the NADH-dependent reduction of a wide variety of α,β-unsaturated carboxylic acids and aldehydes (Rohdich et al., *J. Biol. Chem.* 276:5779-5787 (2001)). This enzyme is encoded by enr in several species of *Clostridia* (Giesel and Simon, *Arch. Microbiol.* 135:51-57 (1983)) including *C. tyrobutyricum* and *C. thermoaceticum* (now called *Moorella thermoaceticum*) (Rohdich, et al., *J. Biol. Chem.* 276:5779-5787 (2001)). In the recently published genome sequence of *C. kluyveri*, 9 coding sequences for enoate reductases have been reported, out of which one has been characterized (Seedorf et al., *Proc. Natl. Acad. Sci. USA* 105:2128-2133 (2008)). The enr genes from both *C. tyrobutyricum* and *C. thermoaceticum* have been cloned and sequenced and show 59% identity to each other. The former gene is also found to have approximately 75% similarity to the characterized gene in *C. kluyveri* (Giesel and Simon, *Arch. Microbiol.* 135:51-57 (1983)). It has been reported based on these sequence results that enr is very similar to the dienoyl CoA reductase in *E. coli* (fadH) (Rohdich et al., *J. Biol. Chem.* 276:5779-5787 (2001)). Several gene candidates thus exist for catalyzing this last step in the 3-oxoadipate pathway and have been listed below. The *C. thermoaceticum* enr gene has also been expressed in an enzymatically active form in *E. coli* (Rohdich et al., supra, 2001). The protein sequences for exemplary gene products can be found using the following GenBank accession numbers:

| fadH | NP_417552.1 | *Escherichia coli* |
|---|---|---|
| enr | ACA54153.1 | *Clostridium botulinum* A3 str |
| enr | CAA71086.1 | *Clostridium tyrobutyricum* |
| enr | CAA76083.1 | *Clostridium kluyveri* |

The above description provides an exemplary adipate synthesis pathway by way of an 3-oxoadipate pathway.

Example IV

Preparation of an Adipate Producing Microbial Organism Having a 3-Oxoadipate Pathway This example describes the generation of a microbial organism capable of producing adipate using the 3-oxoadipate pathway.

*Escherichia coli* is used as a target organism to engineer the 3-oxoadipate pathway as shown in FIG. 3. *E. coli* provides a good host for generating a non-naturally occurring microorganism capable of producing adipate. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce adipate, nucleic acids encoding the enzymes utilized in the 3-oxoadipate pathway are expressed in *E. coli* using well known molecular biology techniques (see, for example, Sambrook, supra, 2001; Ausubel supra, 1999). In particular, the paaJ (NP_415915.1), pcaIJ (AAN69545.1 and NP_746082.1), and bdh (AAA58352.1) genes encoding the succinyl-CoA:acetyl-CoA acyl transferase, 3-oxoadipyl-CoA transferase, and 3-oxoadipate reductase activities, respectively, are cloned into the pZE13 vector (Expressys, Ruelzheim, Germany) under the PA1/lacO promoter. In addition, the acnA (P25516.3) and enr (ACA54153.1) genes encoding 3-hydroxyadipate dehydratase and 2-enoate reductase activities, respectively, are cloned into the pZA33 vector (Expressys, Ruelzheim, Germany) under the PA1/lacO promoter. The two sets of plasmids are transformed into *E. coli* strain MG1655 to express the proteins and enzymes required for adipate synthesis via the 3-oxoadipate pathway.

The resulting genetically engineered organism is cultured in glucose containing medium following procedures well known in the art (see, for example, Sambrook et al., supra, 2001). The expression of the 3-oxoadipate pathway genes for adipate synthesis is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce adipate is confirmed using HPLC, gas chromatography-mass spectrometry (GCMS) and/or liquid chromatography-mass spectrometry (LCMS).

Microbial strains engineered to have a functional adipate synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of adipate. One modeling method is the bilevel optimization approach, OptKnock (Burgard et al., *Biotechnol. Bioengineer.* 84:647-657 (2003)), which is applied to select gene knockouts that collectively result in better production of adipate. Adaptive evolution also can be used to generate better producers of, for example, the acetyl-CoA and succinyl-CoA intermediates or the adipate product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the adipate producer to further increase production.

For large-scale production of adipate, the 3-oxoadipate pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at around a pH of 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu), for example, using an Aminex® series of HPLC columns (for example, HPX-87 series) (BioRad), using a refractive index detector for glucose and alcohols, and a UV detector for organic acids (Lin et al., *Biotechnol. Bioeng.* 775-779 (2005)).

This example describes the preparation of an adipate-producing microbial organism containing a 3-oxidoadipate pathway.

Example V

Adipate Synthesis Via cis,cis-Muconic Acid

This example describes an adipate synthesis pathway previously described (see Niu et al., *Biotechnol. Prog.* 18(2): p. 201-11. 2002; Frost et al., U.S. Pat. No. 5,487,987, issued Jan. 30, 1996).

Figure 5:
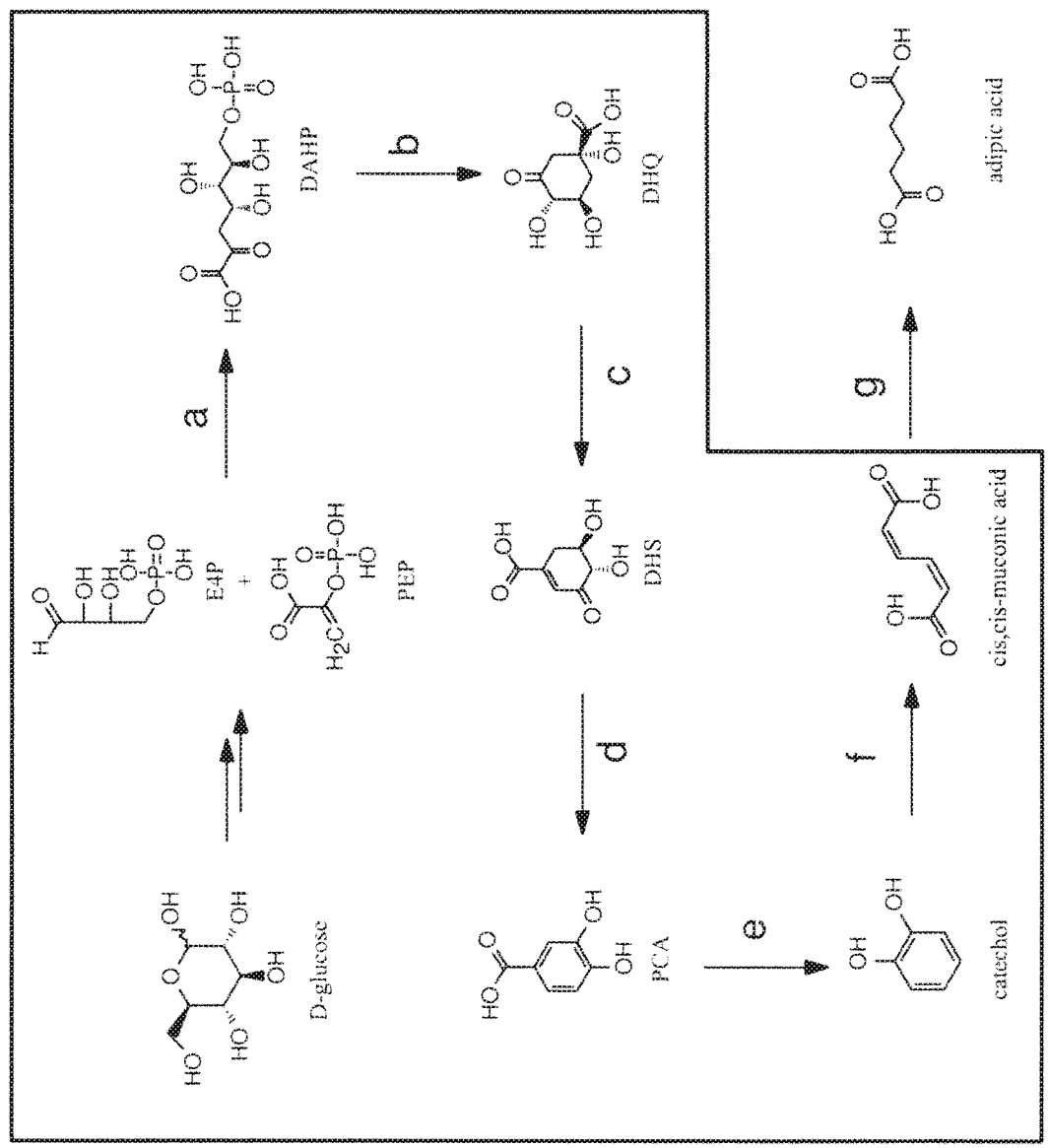
FIG. 5 shows an exemplary pathway for synthesis of adipic acid from glucose via cis,cis-muconic acid. Biosynthetic intermediates (abbreviations): D-erythrose 4-phosphate (E4P), phosphoenolpyruvic acid (PEP), 3-deoxy-D-arabinoheptulosonic acid 7-phosphate (DAHP), 3-dehydroquinic acid (DHQ), 3-dehydroshikimic acid (DHS), protocatechuic acid (PCA). Enzymes (encoding genes) or reaction conditions: (a) DAHP synthase (aroFFBR), (b) 3-dehydroquinate synthase (aroB), (c) 3-dehydroquinate dehydratase (aroD), (d) DHS dehydratase (aroZ), (e) protocatechuate decarboxylase (aroY), (f) catechol 1,2-dioxygenase (catA), (g) 10% Pt/C, $H_2$, 3400 kPa, 25° C. Figure taken from Niu et al., *Biotechnol. Prog.* 18:201-211 (2002)).

Adipate synthesis via a combined biological and chemical conversion process has been previously described. (Niu et al., *Biotechnol. Prog.* 18:201-211 (2002)) and is shown in FIG. 5. This method is further described in U.S. Pat. No. 5,487,987. Adipate synthesis through this route entails introduction of three heterologous genes into *E. coli* that can convert dehydroshikimate into cis,cis-muconic acid (Niu et al., supra, 2002). A final chemical hydrogenation step leads to the formation of adipic acid. In this step, the pretreated fermentation broth that contained 150 mM cis,cis-muconate was mixed with 10% platinum (Pt) on activated carbon. The hydrogenation reaction was carried out at 3400 KPa of hydrogen pressure for two and a half hour at 250° C. with stirring. The calculated adipate yields are shown in Table 3 assuming either an enzymatic or chemical catalysis step is utilized to convert cis,cis-muconate into adipate. Under aerobic conditions, an 85% molar yield of adipate can be obtained if a chemical reaction is employed for hydrogenation and a 75% molar yield is obtained if an NADH-based hydrogenase is used.

TABLE 3

The maximum theoretical yields of adipate per mole of glucose using the using the cis,cis-muconic acid pathway.

| | Final step enzymatic | | Final step chemical hydrogenation | |
|---|---|---|---|---|
| | Aerobic | Anaerobic | Aerobic | Anaerobic |
| Adipate Yield | 0.75 | 0.00 | 0.85 | 0.00 |

Although this is an exemplary method, there are disadvantages of this method compared to others, such as those described in Examples I-IV. For example, the first limitation of this method is the lower theoretical yields compared to the reverse adipate degradation and 3-oxoadipate pathways. The second limitation is that the ATP yields of this pathway are negligible. A third limitation of this pathway is that it involves a dioxygenase, necessitating a supply of oxygen to the bioreactor and precluding the option of anaerobic fermentation.

The above description provides an exemplary adipate synthesis pathway by way of a cis,cis-muconic acid pathway.

Example VI

Adipate Synthesis Via Alpha-Ketoadipate

This example describes an exemplary adipate synthesis pathway via an alpha-ketoadipate pathway.

Alpha-keto adipate is a known intermediate in lysine biosynthesis in *S. cerevisiae*, and this information was used to identify an additional pathway for adipic acid biosynthesis (see FIG. 6). Conversion of alpha-ketoglutarate to alpha-ketoadipate is catalyzed by homocitrate synthase, homoaconitase, and homoisocitrate dehydrogenase as indicated by dashed arrows in FIG. 6. Conversion of alpha-ketoadipate into alpha-hydroxyadipate can be catalyzed by 2-ketoadipate reductase, an enzyme reported to be found in rat and in human placenta (Suda et al., *Arch. Biochem. Biophys.* 176: 610-620 (1976); Suda et al., *Biochem. Biophys. Res. Commun.* 77:586-591 (1977). Subsequent steps involve a dehydratase for the conversion of alpha-hydroxyadipate into hexa-2-enedioate followed by its reduction to adipic acid. This last step can be catalyzed either by an enzyme or can take place through a chemical reaction as described in Example II. Genes encoding the enzymes for the alpha-ketoadipate pathway are identified as described in Examples I-IV.

The adipate yields associated with this pathway are shown in Table 4. Because of the loss of two $CO_2$ molecules during the conversion of acetyl-CoA to adipate, only 67% of the glucose can be converted into adipate. This is reflected in the molar yields for this pathway under aerobic conditions. The yields are further reduced in the absence of oxygen uptake. Also since the maximum ATP yields under anaerobic conditions are negligible, the engineered organism will have to utilize additional substrate to form energy for cell growth and maintenance under such conditions.

TABLE 4

The maximum theoretical yields of adipate and the associated ATP yields per mole of glucose using the using the alpha-ketoadipate pathway.

| | Final step enzymatic | | Final step chemical hydrogenation | |
|---|---|---|---|---|
| | Aerobic | Anaerobic | Aerobic | Anaerobic |
| Adipate Yield | 0.67 | 0.45 | 0.67 | 0.40 |
| Max ATP yield @ max adipate yield | 6.17 | 0.00 | 7.50 | 0.00 |

The above description provides an exemplary adipate synthesis pathway by way of an alpha-ketoadipate pathway.

Example VII

Adipate Synthesis Via Lysine Degradation

This example describes an exemplary adipate synthesis pathway via a lysine degradation pathway.

Figure 7:
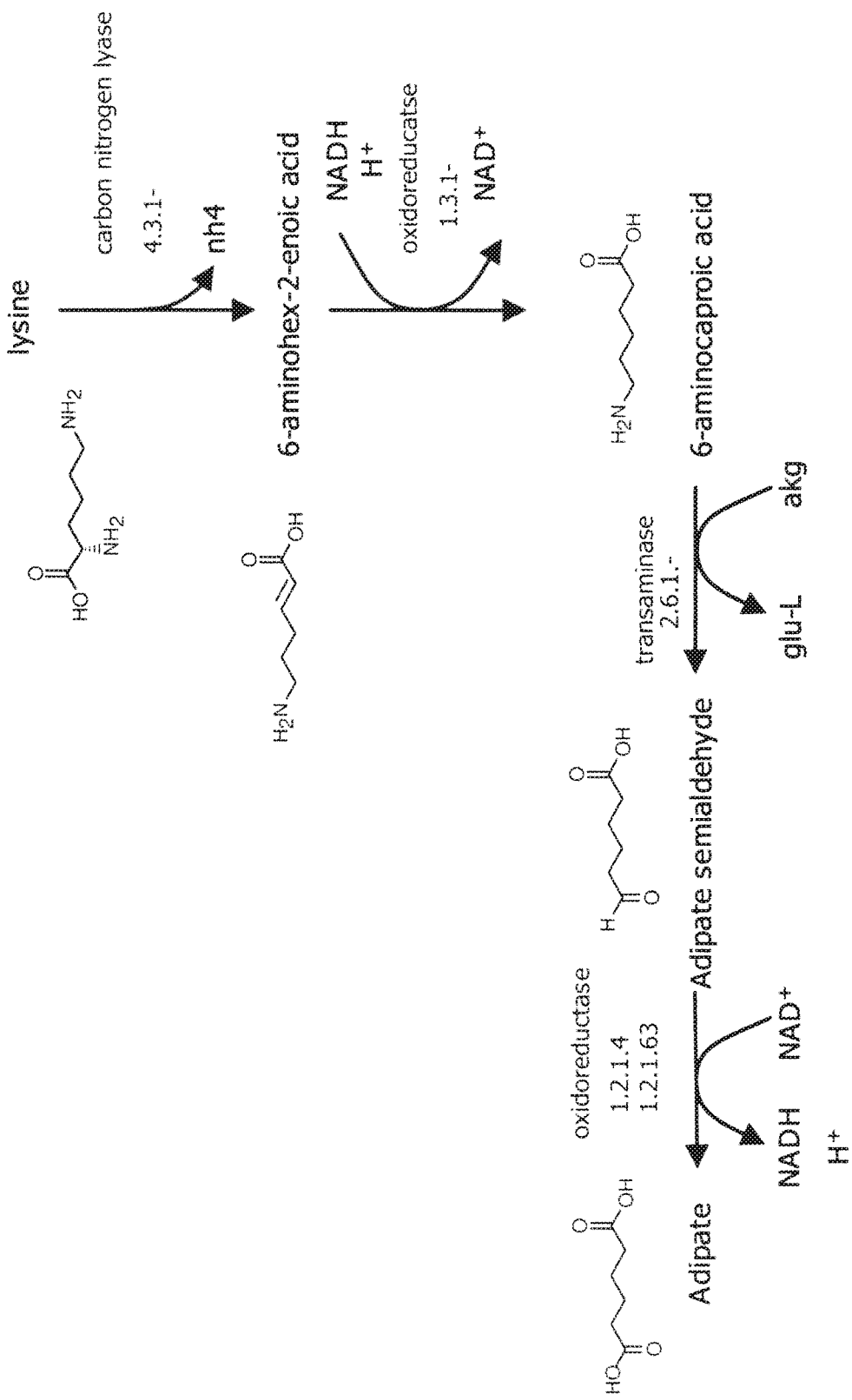
FIG. 7 shows an exemplary pathway for synthesis of adipate using lysine as a starting point.

Two additional pathways for adipate synthesis rely on lysine degradation to form adipate. One pathway starts from alpha-ketoglutarate to form lysine (pathway non-native to *E. coli* and found in *S. cerevisiae*), and the other uses aspartate as a starting point for lysine biosynthesis (pathway native to *E. coli*). FIG. 7 shows adipate formation from lysine. The maximum theoretical yields for adipate, both in the presence and absence of oxygen, using the *E. coli* stoichiometric model are shown in Tables 5 and 6, with alpha-ketoglutarate and aspartate as the respective starting points for lysine. The maximum ATP yields accompanying these theoretical yields were also calculated and are shown in the same tables. These yields are lower in comparison to the other pathways described in Examples I-IV. Genes encoding the enzymes for the alpha-ketoadipate pathway are identified as described in Examples I-IV.

TABLE 5

The maximum theoretical yield of adipate and the accompanying ATP yield per mole of glucose assuming the lysine biosynthesis pathway with alpha-ketoglutarate as a starting point.

|  | Aerobic | Anaerobic |
|---|---|---|
| Adipate Yield | 0.40 | 0.20 |
| Max ATP yield @ max adipate yield | 5.60 | 0.00 |

TABLE 6

The maximum theoretical yield of adipate and the accompanying ATP yield per mole of glucose assuming the lysine biosynthesis pathway with aspartate as a starting point.

|  | Aerobic | Anaerobic |
|---|---|---|
| Adipate Yield | 0.50 | 0.34 |
| Max ATP yield @ max adipate yield | 0.50 | 0.04 |

The above description provides an exemplary adipate synthesis pathway by way of a lysine degradation pathway.

Example VIII

Production of Caprolactam and 6-Aminocaproic Acid Via Adipyl-CoA

This example describes an exemplary caprolactam and/or 6-aminocaproic acid synthesis pathway via an adipyl-CoA pathway.

An exemplary pathway for forming caprolactam and/or 6-aminocaproic acid using adipyl-CoA as the precursor is shown in FIG. 8. The pathway involves a CoA-dependant aldehyde dehydrogenase that can reduce adipyl-CoA to adipate semialdehyde and a transaminase or 6-aminocaproate dehydrogenase that can transform this molecule into 6-aminocaproic acid. The terminal step that converts 6-aminocaproate into caprolactam can be accomplished either via an amidohydrolase or via chemical conversion (Guit and Buij s, U.S. Pat. No. 6,353,100, issued Mar. 7, 2002; Wolters et al., U.S. Pat. No. 5,700,934, issued Dec. 23, 1997; Agterberg et al., U.S. Pat. No. 6,660,857, issued Dec. 9, 2003). The maximum theoretical yield of caprolactam was calculated to be 0.8 mole per mole glucose consumed (see Table 7) assuming that the reverse adipate degradation pathway was complemented with the reaction scheme shown in FIG. 8. The pathway is favorable energetically as up to 0.78 moles of ATP are formed per mole of glucose consumed at the maximum theoretical yield of caprolactam. The ATP yield can be further improved to 1.63 moles of ATP produced per mole of glucose if phosphoenolpyruvate carboxykinase (PPCK) is assumed to function in the ATP-generating direction towards oxaloacetate formation.

The final amidohydrolase step is energetically and redox neutral, and thus the product and ATP molar yields associated with 6-aminocaproic acid production are equivalent to those associated with caprolactam production. Thus one can alternatively envision a microorganism and associated fermentation process that forms 6-aminocaproic acid instead of caprolactam followed by an additional unit operation to dehydrate/cyclize 6-aminocaproic acid to caprolactam.

TABLE 7

The maximum theoretical yield of caprolactam and the accompanying ATP yield per mole of glucose assuming that the reverse fatty acid degradation pathway is complemented with the reaction scheme from FIG. 8.

|  | Aerobic | Anaerobic |
|---|---|---|
| Caprolactam Yield | 0.80 | 0.80 |
| Max ATP yield @ max Caprolactam yield | 0.78 | 0.78 |
| Max ATP yield @ max Caprolactam yield PPCK assumed | 1.63 | 1.63 |

Successfully engineering this pathway involves identifying an appropriate set of enzymes with sufficient activity and specificity. This entails identifying an appropriate set of enzymes, cloning their corresponding genes into a production host, optimizing fermentation conditions, and assaying for product formation following fermentation. To engineer a production host for the production of 6-aminocaproic acid or caprolactam, one or more exogenous DNA sequence(s) can be expressed in a host microorganism. In addition, the microorganism can have endogenous gene(s) functionally deleted. These modifications will allow the production of 6-aminocaproate or caprolactam using renewable feedstock.

Below is described a number of biochemically characterized candidate genes capable of encoding enzymes that catalyze each step of the caprolactam formation pathway described in FIG. 8. Although described for *E. coli*, one skilled in the art can apply these teachings to any other suitable host organism. Specifically, the genes listed are native to *E. coli* or are genes in other organisms that can be applied to catalyze the appropriate transformations when properly cloned and expressed.

Referring to FIG. 8, step 1 involves CoA-dependant aldehyde dehydrogenase. Exemplary genes that encode enzymes for catalyzing the reduction of an acyl-coA to its corresponding aldehyde include the *Acinetobacter calcoaceticus* acr1 encoding a fatty acyl-CoA reductase (Reiser and Somerville, *J. Bacteriol.* 179:2969-2975 (1997)), the *Acinetobacter* sp. M-1 fatty acyl-CoA reductase (Ishige et al., *Appl. Environ. Microbiol.* 68:1192-1195 (2002)) and the sucD gene from *Clostridium kluyveri* (Sohling and Gottschalk, *J. Bacteriol.* 178:871-880 (1996)), which can convert succinyl-CoA to succinate semialdehyde.

| Gene name | GenBank Accession # | Organism |
|---|---|---|
| acr1 | YP_047869.1 | *Acinetobacter calcoaceticus* |
|  | BAB85476.1 | *Acinetobacter* sp. Strain M-1 |
| sucD | P38947.1 | *Clostridium kluyveri* |

Referring to FIG. 8, step 2 involves transaminase. The second step in the pathway is conversion of the 6-aldehyde to an amine. This transformation can likely be accomplished by gamma-aminobutyrate transaminase (GABA transaminase), a native enzyme encoded by gabT that transfers an amino group from glutamate to the terminal aldehyde of succinyl semialdehyde (Bartsch et al., *J. Bacteriol.* 172: 7035-7042 (1990)). GABA transaminases in *Mus musculus*, *Pseudomonas fluorescens*, and *Sus scrofa* have been shown to react with 6-aminocaproic acid (Cooper, *Methods Enzymol.* 113:80-82 (1985); Scott and Jakoby, *J. Biol. Chem.* 234:932-936 (1959)). The protein sequences for exemplary gene products can be found using the following GenBank accession numbers:

| | | |
|---|---|---|
| gabT | NP_417148.1 | *Escherichia coli* |
| abat | NP_766549.2 | *Mus musculus* |
| gabT | YP_257332.1 | *Pseudomonas fluorescens* |
| abat | NP_999428.1 | *Sus scrofa* |

Referring to FIG. 8, step 2 can alternatively involve 6-aminocaproate dehydrogenase which comprises the reductive amination of adipate semialdehyde to form 6-aminocaproate. This transformation can be accomplished by lysine-6-dehydrogenase, which naturally converts L-lysine to 2-aminoadipate-6-semialdehyde. Exemplary enzymes can be found in *Geobacillus stearothermophilus* (Heydari et al., *Appl. Environ. Microbiol.* 70(2):937-942 (2004)), *Agrobacterium tumefaciens* (Hashimoto et al., *J. Biochem.* (Tokyo), 106(1):76-80 (1989); Misono et al., *J. Biochem.* (Tokyo), 105(6):1002-1008 (1989)), and *Achromobacter denitrificans* (Ruldeekulthamrong et al., *BMB Reports* 790-795 (2008)).

| | | |
|---|---|---|
| lysDH | BAB39707 | *Geobacillus stearothermophilus* |
| lysDH | NP_353966 | *Agrobacterium tumefaciens* |
| lysDH | AAZ94428 | *Achromobacter denitrificans* |

Referring to FIG. 8, step 3 involves amidohydrolase. The final step of caprolactam synthesis is cyclization of 6-aminocaproic acid. This transformation has not been characterized enzymatically but it is very similar to the cyclization of lysine by D-lysine lactamase (EC 3.5.2.11) from *Cryptococcus laurentii* (Fukumura et al., *FEBS Lett.* 89:298-300 (1978)). However, the protein and nucleotide sequences of this enzyme are not currently known and, so far, lysine lactamase activity has not been demonstrated in other organisms.

Plasmids contained in several strains of *Pseudomonas* sp. isolated from soil have been shown to confer ability to grow on caprolactam as a sole carbon source (Boronin et al., *FEMS Microbiol. Lett.* 22:167-170 (1984)); however, associated gene or protein sequences have not been associated with this function to date.

The most closely related candidate enzyme with available sequence information is 6-aminohexanoate-cyclic dimer hydrolase, which has been characterized in *Pseudomonas* sp. and *Flavobacterium* sp. The nylB gene product from *Pseudomonas* sp NK87 was cloned and expressed in *E. coli* (Kanagawa et al., *J. Gen. Microbiol.* 139:787-795 (1993)). The substrate specificity of the enzyme was tested in *Flavobacterium* sp K172 and was shown to react with higher-order oligomers of 6-aminohexanoate but not caprolactam (Kinoshita et al., *Eur. J. Biochem.* 116:547-551 (1981)). The reversibility and ability of 6-aminohexanoate dimer hydrolases in other organisms to react with the desired substrate in the direction of interest can be further tested. The protein sequences for exemplary gene products can be found using the following GenBank accession numbers:

| | | |
|---|---|---|
| nylB | AAA24929.1 | *Pseudomonas* sp NK87 |
| nylB | P13397 | *Flavobacterium* sp K172 |
| nylB | YP_949627.1 | *Arthrobacter aurescens* TC1 |

The above description provides an exemplary pathway to produce caprolactam and/or 6-aminocaproic acid by way of an adipyl-CoA pathway.

Example IX

Preparation of a 6-Aminocaproate or Caprolactam Producing Microbial Organism Having a 3-Oxoadipate Pathway This example describes the generation of a microbial organism capable of producing adipate using the reverse degradation pathway and converting the intracellular adipate to 6-aminocaproate and/or caprolactam.

*Escherichia coli* is used as a target organism to engineer the necessary genes for adipate, 6-aminocaproate, and/or caprolactam synthesis (see FIG. 2 and FIG. 8). *E. coli* provides a good host for generating a non-naturally occurring microorganism capable of producing adipate, 6-aminocaproate, and/or caprolactam. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce 6-aminocaproate and/or caprolactam, nucleic acids encoding the enzymes utilized in the reverse adipate degradation pathway and 6-aminocaproate or caprolactam synthesis pathways are expressed in *E. coli* using well known molecular biology techniques (see, for example, Sambrook, supra, 2001; Ausubel, supra, 1999). In particular, the paaJ (NP_415915.1), paaH (NP_415913.1), and maoC (NP_415905.1) genes encoding the succinyl-CoA:acetyl-CoA acyl transferase, 3-hydroxyacyl-CoA dehydrogenase, and 3-hydroxyadipyl-CoA dehydratase activities, respectively, are cloned into the pZE13 vector (Expressys, Ruelzheim, Germany) under the PA1/lacO promoter. In addition, the bcd (NP_349317.1), etfAB (349315.1 and 349316.1), and sucCD (NP_415256.1 and AAC73823.1) genes encoding 5-carboxy-2-pentenoyl-CoA reductase and adipyl-CoA synthetase activities, respectively, are cloned into the pZA33 vector (Expressys, Ruelzheim, Germany) under the PA1/lacO promoter. Lastly, the acr1 (YP_047869.1), gabT (NP_417148.1), and nylB (AAA24929.1) genes encoding CoA-dependent aldehyde dehydrogenase, transaminase, and amidohydrolase activities are cloned into a third compatible plasmid, pZS23, under the PA1/lacO promoter. pZS23 is obtained by replacing the ampicillin resistance module of the pZS13 vector (Expressys, Ruelzheim, Germany) with a kanamycin resistance module by well-known molecular biology techniques. The three sets of plasmids are transformed into *E. coli* strain MG1655 to express the proteins and enzymes required for 6-aminocaproate and/or caprolactam synthesis.

The resulting genetically engineered organism is cultured in glucose containing medium following procedures well known in the art (see, for example, Sambrook et al., supra, 2001). The expression of the 6-aminocaproate and caprolactam synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce 6-aminocaproate and/or caprolactam is confirmed using HPLC, gas chromatography-mass spectrometry (GCMS) and/or liquid chromatography-mass spectrometry (LCMS).

Microbial strains engineered to have a functional pathway for the synthesis of 6-aminocaproate and/or caprolactam are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 6-aminocaproate and/or caprolactam. One modeling method is the bilevel optimization approach, OptKnock (Burgard et al., *Biotechnol. Bioengineer.* 84:647-657 (2003)), which is applied to select gene knockouts that collectively result in better production of 6-aminocaproate and/or caprolactam. Adaptive evolution also can be used to generate better producers of, for example, the acetyl-CoA and succinyl-CoA intermediates of the products. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the 6-aminocaproate and/or caprolactam producer to further increase production.

For large-scale production of 6-aminocaproate and/or caprolactam, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at around a pH of 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu), for example, using an Aminex® series of HPLC columns (for example, HPX-87 series) (BioRad), using a refractive index detector for glucose and alcohols, and a UV detector for organic acids (Lin et al., *Biotechnol. Bioeng.* 775-779 (2005)).

Example X

Adipate Synthesis Via 2-Hydroxyadipyl-CoA

This example describes two exemplary adipate synthesis pathways proceeding from alpha-ketoadipate and passing through a 2-hydroxyadipyl-CoA intermediate.

As described in example VI, alpha-ketoadipate is a known intermediate in lysine biosynthesis that can be formed from alpha-ketoglutarate via homocitrate synthase, homoaconitase, and homoisocitrate dehydrogenase. Alpha-ketoadipate can be converted to 2-hydroxyadipyl-CoA by the two routes depicted in FIG. 9. 2-hydroxyadipyl-CoA can be subsequently dehydrated and reduced to adipyl-CoA which can then be converted to adipate as shown in FIG. 9. The maximum yield of adipate from glucose via these pathways is 0.67 mol/mol.

Conversion of alpha-ketoadipate into 2-hydroxyadipate can be catalyzed by 2-ketoadipate reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977)). Alternatively, enzymes capable of reducing alpha-ketoglutarate to 2-hydroxyglutarate may also show activity on alpha-ketoadipate, which is only one carbon atom longer. One such enzyme possessing alpha-ketoglutarate reductase activity is serA of *Escherichia coli* (Zhao and Winkler, *J. Bacteriol.* 178(1):232-9 (1996)). Additional exemplary enzymes can be found in *Arabidopsis thaliana* (Ho, et al., *J. Biol. Chem.* 274(1):397-402 (1999)) and *Haemophilus influenzae*.

| serA | NP_417388.1 | *Escherichia coli* |
| PGDH | NP_564034 | *Arabidopsis thaliana* |
| serA | P43885 | *Haemophilus influenzae* |

Referring to FIG. 9, 2-hydroxyadipate can likely be converted to 2-hydroxyadipyl-CoA by the synthetases, transferases, phosphotransadipylases and kinases described in example I. Alternatively, enzymes with 2-hydroxyglutarate CoA-transferase or glutaconate CoA-transferase activity are likely suitable to transfer a CoA moiety to 2-hydroxyadipate. One example of such an enzyme is encoded by the gctA and gctB genes of *Acidaminococcus fermentans* (Buckel, et al., *Eur. J. Biochem.* 118(2):315-321 (1981); Mack, et al., *Eur. J. Biochem.* 226(1):41-51 (1994)). Similarly, synthetase, transferase, or phosphotransadipylase and kinase activities would be required to convert alpha-ketoadipate into alpha-ketoadipyl-CoA, as depicted in FIG. 9. Conversion of alpha-ketoadipyl-CoA to 2-hydroxyadipyl-CoA can be carried out by an alpha-hydroxyacyl-CoA dehydrogenase enzyme. A similar activity was reported in propionate-adapted *E. coli* cells whose extracts catalyzed the oxidation of lactyl-CoA to form pyruvyl-CoA (Megraw et al., *J. Bacteriol.* 90(4): 984-988 (1965)). Additional hydroxyacyl-CoA dehydrogenases were described in example I.

| gctA | Q59111 | *Acidaminococcus fermentans* |
| gctB | Q59112 | *Acidaminococcus fermentans* |

The dehydration of 2-hydroxyadipyl-CoA to form 5-carboxy-2-pentenoyl-CoA can be carried out by a 2-hydroxyacyl-CoA dehydratase. A 2-hydroxyglutaryl-CoA dehydratase system has been characterized in *Acidaminococcus fermentans* and requires both the hgdA and hgdB subunits and the activator protein, hgdC, for optimal activity (Dutscho et al., *Eur. J. Biochem.* 181(3):741-746 (1989); Locher et al. *J. Mol. Biol.* 307(1):297-308; Muller and Buckel, *Eur. J. Biochem.* 230(2):698-704 (2001); Schweiger et al. *Eur. J. Biochem.* 169(2):441-448 (1987)). This enzyme system is similar in mechanism to the lactoyl-CoA dehydratase from *Clostridium propionicum* (Hofmeister and Buckel, *Eur. J. Biochem.* 206(2):547-552 (1992); Kuchta and Abeles, *J. Biol. Chem.* 260(24):13181-13189 (1985)). Homologs to hgdA, hgdB, and hgdC exist in several organisms.

| | | |
|---|---|---|
| hgdA | P11569 | *Acidaminococcus fermentans* |
| hgdB | P11570 | *Acidaminococcus fermentans* |
| hgdC | P11568 | *Acidaminococcus fermentans* |
| hgdA | ZP_03731126.1 | *Clostridium* sp. M62/1 |
| hgdB | ZP_03731125.1 | *Clostridium* sp. M62/1 |
| hgdC | ZP_03731127.1 | *Clostridium* sp. M62/1 |
| hgdA | NP_603114.1 | *Fusobacterium nucleatum* ATCC 25586 |
| hgdB | NP_603115.1 | *Fusobacterium nucleatum* ATCC 25586 |
| hgdC | NP_603113.1 | *Fusobacterium nucleatum* ATCC 25586 |

Conversion of 5-carboxy-2-pentenoyl-CoA to adipate is carried out by the enzymes described in Example I.

The above description provides an exemplary adipate synthesis pathway by way of a 2-hydroxyadipyl-CoA pathway.

Example XI

Preparation of an Adipate Producing Microbial Organism Having a 2-Hydroxyadipyl-CoA Pathway This example describes the generation of a microbial organism capable of producing adipate using a 2-hydroxyadipyl-CoA pathway.

*Escherichia coli* is used as a target organism to engineer the necessary genes for adipate synthesis (see FIG. 9). *E. coli* provides a good host for generating a non-naturally occurring microorganism capable of producing adipate. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce adipate, nucleic acids encoding the enzymes utilized in a 2-hydroxyadipyl-CoA to adipate pathway are expressed in *E. coli* using well known molecular biology techniques (see, for example, Sambrook, supra, 2001; Ausubel, supra, 1999). In particular, the serA (NP_417388.1), gctA (Q59111), and gctB (Q59112) genes encoding the 2-hydroxyadipate dehydrogenase and 2-hydroxyadipyl-CoA:acetyl-CoA transferase activities, respectively, are cloned into the pZE13 vector (Expressys, Ruelzheim, Germany) under the PA1/lacO promoter. In addition, the hgdA (P11569), hgdB (P11570), and hgdC (P11568) genes encoding 2-hydroxyadipyl-CoA dehydratase activity, respectively, are cloned into the pZA33 vector (Expressys, Ruelzheim, Germany) under the PA1/lacO promoter. Further, the bcd (NP_349317.1), etfAB (349315.1 and 349316.1), and sucCD (NP_415256.1 and AAC73823.1) genes encoding 5-carboxy-2-pentenoyl-CoA reductase and adipyl-CoA synthetase activities are cloned into a third compatible plasmid, pZS23, under the PA1/lacO promoter. pZS23 is obtained by replacing the ampicillin resistance module of the pZS13 vector (Expressys, Ruelzheim, Germany) with a kanamycin resistance module by well-known molecular biology techniques. The three sets of plasmids are transformed into *E. coli* strain MG1655 to express the proteins and enzymes required for adipate synthesis.

The resulting genetically engineered organism is cultured in glucose containing medium following procedures well known in the art (see, for example, Sambrook et al., supra, 2001). The expression of the 2-hydroxyadipyl-CoA pathway genes for adipate synthesis is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce adipate is confirmed using HPLC, gas chromatography-mass spectrometry (GCMS) and/or liquid chromatography-mass spectrometry (LCMS).

Microbial strains engineered to have a functional adipate synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of adipate. One modeling method is the bilevel optimization approach, OptKnock (Burgard et al., *Biotechnol. Bioengineer.* 84:647-657 (2003)), which is applied to select gene knockouts that collectively result in better production of adipate. Adaptive evolution also can be used to generate better producers of, for example, the alpha-ketoadipate intermediate or the adipate product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the adipate producer to further increase production.

For large-scale production of adipate, the 2-hydroxyadipyl-CoA pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at around a pH of 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu), for example, using an Aminex® series of HPLC columns (for example, HPX-87 series) (BioRad), using a refractive index detector for glucose and alcohols, and a UV detector for organic acids (Lin et al., *Biotechnol. Bioeng.* 775-779 (2005)).

This example describes the preparation of an adipate-producing microbial organism containing a 2-hydroxyadipyl-CoA pathway.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism, comprising a microbial organism having an adipate pathway comprising at least one exogenous nucleic acid encoding an adipate pathway enzyme expressed in a sufficient amount to produce adipate, said adipate pathway comprising alpha-ketoadipyl-CoA synthetase, phosphotransketoadipylase/alpha-ketoadipate kinase or alpha-ketoadipyl-CoA:acetyl-CoA transferase; 2-hydroxyadipyl-CoA dehydrogenase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase.

2. The non-naturally occurring microbial organism of claim 1, wherein said microbial organism comprises two exogenous nucleic acids each encoding an adipate pathway enzyme.

3. The non-naturally occurring microbial organism of claim 1, wherein said microbial organism comprises three exogenous nucleic acids each encoding an adipate pathway enzyme.

4. The non-naturally occurring microbial organism of claim 1, wherein said microbial organism comprises four exogenous nucleic acids each encoding an adipate pathway enzyme.

5. The non-naturally occurring microbial organism of claim 1, wherein said microbial organism comprises five exogenous nucleic acids each encoding an adipate pathway enzyme.

6. The non-naturally occurring microbial organism of claim 5, wherein said five exogenous nucleic acids encode alpha-ketoadipyl-CoA synthetase, phosphotransketoadipylase/alpha-ketoadipate kinase or alpha-ketoadipyl-CoA:acetyl-CoA transferase; 2-hydroxyadipyl-CoA dehydrogenase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase.

7. The non-naturally occurring microbial organism of claim 1, wherein said at least one exogenous nucleic acid is a heterologous nucleic acid.

8. The non-naturally occurring microbial organism of claim 1, wherein said non-naturally occurring microbial organism is in a substantially anaerobic culture medium.

9. The non-naturally occurring microbial organism of claim 1, wherein said microbial organism is a species of bacteria, yeast or fungus.

10. The non-naturally occurring microbial organism of claim 1, wherein said microbial organism is a species of bacteria selected from the group consisting of *Escherichia coli, Klebsiella oxytoca, Anaerobiospirillum succiniciproducens, Actinobacillus succinogenes, Mannheimia succiniproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens* and *Pseudomonas putida*.

11. The non-naturally occurring microbial organism of claim 1, wherein said microbial organism is a species of yeast or fungus selected from the group consisting of *Saccharomyces cerevisiae, Schizosaccharomyces pombe, Kluyveromyces lactis, Kluyveromyces marxianus, Aspergillus terreus, Aspergillus niger* and *Pichia pastoris*.

12. The non-naturally occurring microbial organism of claim 11, wherein said microbial organism is a species of *Saccharomyces cerevisiae*.

13. A method for producing adipate, comprising culturing the non-naturally occurring microbial organism of claim 1 under conditions and for a sufficient period of time to produce adipate.

14. The method of claim 13, wherein said non-naturally occurring microbial organism is in a substantially anaerobic culture medium.

15. The method of claim 13, wherein said method further comprises separating the adipate from other components in the culture.

16. The method of claim 15, wherein said separating comprises extraction, continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, absorption chromatography or ultrafiltration.

* * * * *